(12) United States Patent
Palermo et al.

(10) Patent No.: US 8,207,183 B2
(45) Date of Patent: Jun. 26, 2012

(54) INHIBITORS OF IAP

(75) Inventors: Mark G. Palermo, Cambridge, MA (US); Sushil Kumar Sharma, East Hanover, NJ (US); Christopher Sean Straub, Cambridge, MA (US); Run-Ming Wang, Cambridge, MA (US); Leigh Zawel, Cambridge, MA (US); Yanling Zhang, Shanghai (CN); Zhuoliang Chen, Cambridge, MA (US); Yaping Wang, Cambridge, MA (US); Fan Yang, Cambridge, MA (US); Wojciech Wrona, Cambridge, MA (US); Gang Liu, Cambridge, MA (US); Mark G. Charest, Cambridge, MA (US); Feng He, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/178,946

(22) Filed: Jul. 8, 2011

(65) Prior Publication Data

US 2011/0281875 A1    Nov. 17, 2011

Related U.S. Application Data

(63) Continuation of application No. 10/594,413, filed as application No. PCT/EP2005/003619 on Apr. 6, 2005, now abandoned.

(60) Provisional application No. 60/560,186, filed on Apr. 7, 2004.

(51) Int. Cl.
*A61K 31/427* (2006.01)
*A61K 31/4245* (2006.01)
*A61K 31/422* (2006.01)
*A61K 31/435* (2006.01)
*A61K 31/40* (2006.01)
*A61K 31/506* (2006.01)
*A61K 31/41* (2006.01)
*C07D 277/20* (2006.01)
*C07D 271/06* (2006.01)
*C07D 263/30* (2006.01)
*C07D 401/02* (2006.01)
*C07D 239/02* (2006.01)
*C07D 403/02* (2006.01)

(52) U.S. Cl. ........ 514/275; 514/277; 514/364; 514/365; 514/374; 514/381; 514/408; 544/322; 546/276.4; 548/131; 548/200; 548/234; 548/254; 548/540

(58) Field of Classification Search .................. 514/275, 514/277, 364, 365, 374, 381, 408; 544/322; 546/276.4; 548/131, 200, 234, 254, 540
See application file for complete search history.

(56) References Cited

U.S. PATENT DOCUMENTS

| 4,278,793 | A | 7/1981 | Durckheimer et al. |
| 4,720,484 | A | 1/1988 | Vincent et al. |
| 5,411,942 | A | 5/1995 | Widmer et al. |
| 5,559,209 | A | 9/1996 | Nishimoto et al. |
| 6,472,172 | B1 | 10/2002 | Deng et al. |
| 6,608,026 | B1 | 8/2003 | Wang et al. |
| 7,419,975 | B2 | 9/2008 | Palermo et al. |
| 2003/0157522 | A1 | 8/2003 | Boudreault et al. |
| 2004/0171554 | A1 | 9/2004 | Deshayes et al. |
| 2005/0197403 | A1 | 9/2005 | Harran et al. |
| 2005/0214802 | A1 | 9/2005 | Fairbrother et al. |
| 2006/0167066 | A1 | 7/2006 | Cohen et al. |

FOREIGN PATENT DOCUMENTS

| WO | WO 01/90070 A2 | 11/2001 |
| WO | WO 2004/007529 A2 | 1/2004 |
| WO | WO 2005/069888 A2 | 8/2005 |
| WO | WO 2005/097791 A1 | 10/2005 |
| WO | WO 2006/014361 A1 | 2/2006 |
| WO | WO 2006/069063 A1 | 6/2006 |
| WO | WO 2008/016893 A1 | 2/2008 |

OTHER PUBLICATIONS

EP File History for EP Application Serial No. 05 854 815.7-2101, Applicant: Genentech, Inc., (Feb. 20, 2008-Feb. 15, 2010).
Arnt et al., "Synthetic SMAC/Diablo peptides enhance the effects of chemotherapeutic agents by binding XIAP and CIAP1 in situ", Journal of Biological Chemistry, vol. 277 (46), pp. 44236-44243, (2002).
Kipp et al., "Molecular targeting of inhibitor of apoptosis based on small molecule mimics of natural binding partners", Biochemistry, vol. 41 (23), pp. 7344-7349, (2002).
Wu et al., "Structural analysis of a functional DJAP1 fragment bound to grim and hid peptides", Molecular Cell, vol. 8 (1), pp. 95-104, (2001).
Deal et al., "Conformationally constrained tachykinin analogues: potent and highly selective neurokinin NK-2-receptor antagonists", Journal of Medicincal Chemistry, vol. 35 (22), pp. 4195-4204, (1992).
Deng et al., "Kinetic Control of Proline Amide Rotamers: Total Synthesis of trans,transand cis,cis-Ceratospongamide", J. Am. Chem. Soc., 2002 vol. 124 No. 6 pp. 916-917.

(Continued)

*Primary Examiner* — Rebecca Anderson
*Assistant Examiner* — Samantha Shterengarts
(74) *Attorney, Agent, or Firm* — Arlene K. Musser

(57) ABSTRACT

Novel compounds that inhibit the binding of the Smac protein to Inhibitor of Apoptosis Proteins (IAPs) of the formula (I).

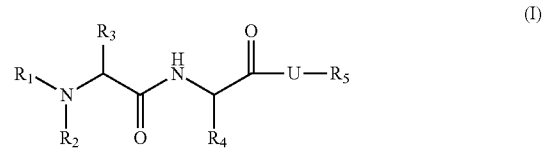

(I)

15 Claims, No Drawings

OTHER PUBLICATIONS

Klein et al., "Lyngbyapeptin A, a modified tetrapeptide from Lyngbya bouillonii (Cyanophyceae)", Tetrahedron Letters, 1999 vol. 40 pp. 695-696.

Pichon-Pesme et al., "On Building a Data Bank of Transferable Experimental Electron Density Parameters: Application of Polypeptides", J. Phys. Chem., 1995 vol. 99 pp. 6242-6250.

Yokokawa et al., "Total Synthesis of cis,cis-Ceratospongamide, a Bioactive Thiazole-Containing Cyclic Peptide from Marine Origin", Synlett, 2001 Special Issue pp. 986-988.

Yokokawa et al., "Total synthesis and conformational studies of ceratospongamide, a bioactive cyclic heptapeptide from marine origin", Tetrahedron, 2002 vol. 58 pp. 8127-8143.

Lawton et al., "A Bioactive Modified Peptide, Aeruginosamide, Isolated from the Cyanobacterium Microcystis aeruginosa" The Journal of Organic Chemistry, 1999 vol. 64 pp. 5329-5332.

Li et al., "A Small Molecule Smac Mimic Potentiates TRAIL- and TNFα-Mediated Cell Death", Science, 2004 vol. 305 pp. 1471-1474.

Stables et al., "A Novel Peptidic Tachykinin Antagonist Which is Potent at NK3 Receptors", Neuropeptides, 1994 vol. 27 pp. 333-341.

Gordon, Tom et al. "Peptide Azoles: A New Class of Biologically-Active Dipeptide Mimetics", Bioorganic & Medicinal Chemistry Letters, 1993, vol. 3, No. 5, pp. 915-920, Pergamon Press Ltd., Great Britain.

Liu, Zhihong et al. "Structural Basis for Binding of Smac/DIABLO to the XIAP BIR3 Domain", Nature, 2000, vol. 408, pp. 1004-1008.

Thompson, Scott K. et al. "Synthesis and Antiviral Activity of a Novel Class of HIV-1 Protease Inhibitors Containing a Heterocyclic P1'-P2' Amide Bond Isostere", Bioorganic & Medicinal Chemistry Letters, 1994, vol. 4, No. 20, pp. 2441-2446, Elsevier Science Ltd., Great Britain.

Thompson, Scott K. et al. "Rational Design, Synthesis, and Crystallographic Analysis of a Hydroxyethylene-Based HIV-1 Protease Inhibitor Containing a Heterocyclic P1'-P2' Amide Bond Isostere", J. Med. Chem., 1994, vol. 37, pp. 3100-3107.

Thompson, Scott K. et al. "Design of Potent and Selective Human Cathepsin K Inhibitors that Span the Active Site", Proc. Natl. Acad. Sci. USA, Dec. 1997, vol. 94, pp. 14249-14254.

Wu, Geng et al. "Structural Basis of IAP Recognition by Smac/Diablo", Nature, 2000, vol. 408, pp. 1008-1012.

INHIBITORS OF IAP

This application is a Continuation of U.S. National Phase application Ser. No. 10/594,413 filed Apr. 21, 2008 now abandoned which is a 371 of International Application Serial No. PCT/EP2005/003619 filed Apr. 6, 2005 which claims priority to U.S. Provisional Application Ser. No. 60/560,186 filed Apr. 7, 2004, the contents of which are incorporated herein by reference in their entirety.

The present invention relates generally to novel compounds that inhibit the binding of the Smac protein to Inhibitor of Apoptosis Proteins (IAPs). The present invention includes novel compounds, novel compositions, methods of their use and methods of their manufacture, where such compounds are generally pharmacologically useful as agents in therapies whose mechanism of action rely on the inhibition of the Smac/IAP interaction, and more particularly useful in therapies for the treatment of proliferative diseases, including cancer.

BACKGROUND

Programmed cell death plays a critical role in regulating cell number and in eliminating stressed or damaged cells from normal tissues. Indeed, the network of apoptotic signaling mechanisms inherent in most cell types provides a major barrier to the development and progression of human cancer. Since most commonly used radiation and chemo-therapies rely on activation of apoptotic pathways to kill cancer cells, tumor cells which are capable of evading programmed cell death often become resistant to treatment.

Apoptosis signaling networks are classified as either intrinsic when mediated by death receptor-ligand interactions or extrinsic when mediated by cellular stress and mitochondrial permeabilization. Both pathways ultimately converge on individual Caspases. Once activated, Caspases cleave a number of cell death-related substrates, effecting destruction of the cell.

Tumor cells have devised a number of strategies to circumvent apoptosis. One recently reported molecular mechanism involves the overexpression of members of the IAP (Inhibitor of Apoptosis) protein family. IAPs sabotage apoptosis by directly interacting with and neutralizing Caspases. The prototype IAPs, XIAP and cIAP have three functional domains referred to as BIR 1, 2 & 3 domains. BIR3 domain interacts directly with Caspase 9 and inhibits its ability to bind and cleave its natural substrate, Procaspase 3.

It has been reported that a proapoptotic mitochondrial protein, Smac (also known as DIABLO), is capable of neutralizing XIAP and/or cIAP by binding to a peptide binding pocket (Smac binding site) on the surface of BIR3 thereby precluding interaction between XIAP and/or cIAP and Caspase 9. The present invention relates to therapeutic molecules that bind to the Smac binding pocket thereby promoting apoptosis in rapidly dividing cells. Such therapeutic molecules are useful for the treatment of proliferative diseases, including cancer. In other words, Smac analogs would bind to BIR3 domain of IAPs and will remove the IAP's inhibition of activated Caspase 9 which would then go on to induce apoptosis.

SUMMARY OF THE INVENTION

The present invention relates generally to novel compounds that inhibit the binding of the Smac protein to Inhibitor of Apoptosis Proteins (IAPs). The present invention includes novel compounds, novel compositions, methods of their use and methods of their manufacture, where such compounds are generally pharmacologically useful as agents in therapies whose mechanism of action rely on the inhibition of the Smac/IAP interaction, and more particularly useful in therapies for the treatment of proliferative diseases, including cancer.

DETAILED DESCRIPTION

The present invention relates to compounds of the formula (I)

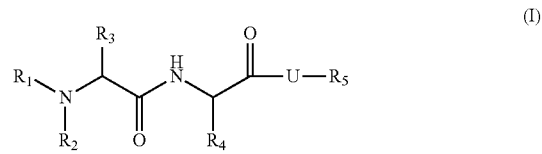

wherein
$R_1$ is H; $C_1$-$C_4$ alkyl; $C_1$-$C_4$ alkenyl; $C_1$-$C_4$ alkynyl or $C_3$-$C_{10}$cycloalkyl which are unsubstituted or substituted;
$R_2$ is H; $C_1$-$C_4$ alkyl; $C_1$-$C_4$ alkenyl; $C_1$-$C_4$ alkynyl or $C_3$-$C_{10}$cycloalkyl which are unsubstituted or substituted;
$R_3$ is H; —$CF_3$; —$C_2F_5$; $C_1$-$C_4$ alkyl; $C_1$-$C_4$ alkenyl; $C_1$-$C_4$ alkynyl; —$CH_2$—Z or $R_2$ and $R_3$ together with the nitrogen form a het ring;
Z is H; —OH; F; Cl; —$CH_3$; —$CF_3$; —$CH_2$Cl; —$CH_2$F or —$CH_2$OH;
$R_4$ is $C_1$-$C_{16}$ straight or branched alkyl; $C_1$-$C_{16}$ alkenyl; $C_1$-$C_{16}$ alkynyl; or —$C_3$-$C_{10}$cycloalkyl; —$(CH_2)_{1-6}$—$Z_1$; —$(CH_2)_{0-6}$-aryl; and —$(CH_2)_{0-6}$-het; wherein alkyl, cycloalkyl and phenyl are unsubstituted or substituted;
$Z_1$ is —N($R_8$)—C(O)—$C_1$-$C_{10}$alkyl; —N($R_8$)—C(O)—$(CH_2)_{1-6}$—$C_3$-$C_7$cycloalkyl; —N($R_8$)—C(O)—$(CH_2)_{0-6}$-phenyl; —N($R_8$)—C(O)—$(CH_2)_{1-6}$-het; —C(O)—N($R_9$)($R_{10}$); —C(O)—O—$C_1$-$C_{10}$alkyl; —C(O)—O—$(CH_2)_{1-6}$—$C_3$-$C_7$cycloalkyl; —C(O)—O—$(CH_2)_{0-6}$-phenyl; —C(O)—O—$(CH_2)_{1-6}$-het; —O—C(O)—$C_1$-$C_{10}$alkyl; —O—C(O)—$(CH_2)_{1-6}$—$C_3$-$C_7$cycloalkyl; —O—C(O)—$(CH_2)_{0-6}$-phenyl; —O—C(O)—$(CH_2)_{1-6}$-het; wherein alkyl, cycloalkyl and phenyl are unsubstituted or substituted;
het is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S, which heterocyclic ring or fused ring system is unsubstituted or substituted on a carbon or nitrogen atom;
$R_8$ is H; —$CH_3$; —$CF_3$; —$CH_2$OH or —$CH_2$Cl;
$R_9$ and $R_{10}$ are each independently H; $C_1$-$C_4$ alkyl; $C_3$-$C_7$cycloalkyl; —$(CH_2)_{1-6}$—$C_3$-$C_7$cycloalkyl; —$(CH_2)_{0-6}$-phenyl; wherein alkyl, cycloalkyl and phenyl are unsubstituted or substituted, or $R_9$ and $R_{10}$ together with the nitrogen form het;
$R_5$ is H; $C_1$-$C_{10}$-alkyl; aryl; phenyl; $C_3$-$C_7$cycloalkyl; —$(CH_2)_{1-6}$—$C_3$-$C_7$cycloalkyl; —$C_1$-$C_{10}$alkyl-aryl; —$(CH_2)_{0-6}$—$C_3$-$C_7$cycloalkyl-$(CH_2)_{0-6}$-phenyl; —$(CH_2)_{0-4}$CH—(($CH_2)_{1-4}$-phenyl)$_2$; —$(CH_2)_{0-6}$—CH(phenyl)$_2$; -indanyl; —C(O)—$C_1$-$C_{10}$alkyl; —C(O)—$(CH_2)_{1-6}$—$C_3$-$C_7$-cycloalkyl; —C(O)—$(CH_2)_{0-6}$-phenyl; —$(CH_2)_{0-6}$—C(O)-phenyl; —$(CH_2)_{0-6}$-het; —C(O)—$(CH_2)_{1-6}$-het; or $R_5$ is a residue of an amino acid, wherein the alkyl, cycloalkyl, phenyl and aryl substituents are unsubstituted or substituted;
U is as shown in structure II:

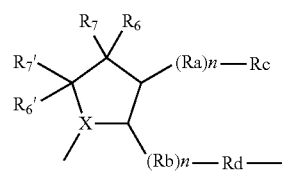

wherein n=0-5;

X is —CH or N;

Ra and Rb are independently an O, S, or N atom or $C_{0-8}$ alkyl wherein one or more of the carbon atoms in the alkyl chain may be replaced by a heteroatom selected from O, S or N, and where the alkyl may be unsubstituted or substituted;

Rd is selected from:
  (a) -Re-Q-(Rf)$_p$(Rg)$_q$; or
  (b) Ar$_1$-D-Ar$_2$;

Rc is H or Rc and Rd may together form a cycloalkyl or het; where if Rd and Rc form a cycloalkyl or het, $R_5$ is attached to the formed ring at a C or N atom;

p and q are independently 0 or 1;

Re is $C_{1-6}$alkyl or alkylidene, and Re which may be unsubstituted or substituted;

Q is N, O, S, S(O), or S(O)$_2$;

Ar$_1$ and Ar$_2$ are substituted or unsubstituted aryl or het;

Rf and Rg are each independently H; —$C_1$-$C_{10}$alkyl; $C_1$-$C_{10}$alkylaryl; —OH; —O—$C_1$-$C_{10}$alkyl; —(CH$_2$)$_{0-6}$—$C_3$-$C_7$cycloalkyl; —O—(CH$_2$)$_{0-6}$-aryl; phenyl; aryl; phenylphenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$; S—$C_1$-$C_{10}$alkyl; aryl-$C_1$-$C_4$ alkyl; het-$C_1$-$C_4$-alkyl wherein alkyl, cycloalkyl, het and aryl are unsubstituted or substituted; —SO$_2$—$C_1$-$C_2$alkyl; —SO$_2$—$C_1$-$C_2$ alkylphenyl; —O—$C_1$-$C_4$alkyl; or $R_g$ and $R_f$ form a ring selected from het or aryl;

D is —CO—; —C(O)—CO$_{1-7}$ alkylene or arylene; —CF$_2$—; —O—; —S(O)$_r$ where r is 0-2; 1,3dioxolane; or $C_{1-7}$ alkyl-OH; where alkyl, alkylene or arylene may be unsubstituted or substituted with one or more halogens, OH, —O—$C_1$-$C_6$alkyl, —S—$C_1$-$C_6$alkyl or —CF$_3$; or D is —N(Rh) wherein Rh is H; $C_{1-7}$ alkyl (unsub or substituted); aryl; —O($C_{1-7}$cycloalkyl) (unsub or substituted); C(O)—$C_1$-$C_{10}$alkyl; C(O)—$C_o$-$C_{10}$alkyl-aryl; C—O—$C_1$-$C_{10}$alkyl; C—O—$C_o$-$C_{10}$alkyl-aryl or SO$_2$—$C_1$-$C_{10}$-alkyl; SO$_2$—($C_o$-$C_{10}$-alkylaryl);

$R_6$, $R_7$, $R'_6$ and $R'_7$ are each independently H; —$C_1$-$C_{10}$alkyl; —$C_1$-$C_{10}$ alkoxy; aryl-$C_1$-$C_{10}$ alkoxy; —OH; —O—$C_1$-$C_{10}$alkyl; —(CH$_2$)$_{0-6}$—$C_3$-$C_7$cycloalkyl; —O—(CH$_2$)$_{0-6}$-aryl; phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$; wherein alkyl, cycloalkyl and aryl are unsubstituted or substituted; and $R_6$, $R_7$, $R'_6$ and $R'_7$ can be united to form a ring system;

$R_{11}$ and $R_{12}$ are independently H; $C_1$-$C_{10}$ alkyl; —(CH$_2$)$_{0-6}$—$C_3$-$C_7$cycloalkyl; —(CH$_2$)$_{0-6}$—(CH)$_{0-1}$(aryl)$_{1-2}$; —C(O)—$C_1$-$C_{10}$alkyl; —C(O)—(CH$_2$)$_{1-6}$—$C_3$-$C_7$cycloalkyl; —C(O)—O—(CH$_2$)$_{0-6}$-aryl; —C(O)—(CH$_2$)$_{0-6}$—O-fluorenyl; —C(O)—NH—(CH$_2$)$_{0-6}$-aryl; —C(O)—(CH$_2$)$_{0-6}$-aryl; —C(O)—(CH$_2$)$_{1-6}$-het; —C(S)—$C_1$-$C_{10}$alkyl; —C(S)—(CH$_2$)$_{1-6}$—$C_3$-$C_7$cycloalkyl; —C(S)—O—(CH$_2$)$_{0-6}$-aryl; —C(S)—(CH$_2$)$_{0-6}$—O-fluorenyl; —C(S)—NH—(CH$_2$)$_{0-6}$-aryl; —C(S)—(CH$_2$)$_{0-6}$-aryl; —C(S)—(CH$_2$)$_{1-6}$-het; wherein alkyl, cycloalkyl and aryl are unsubstituted or substituted; or $R_{11}$ and $R_{12}$ are a substituent that facilitates transport of the molecule across a cell membrane; or $R_{11}$ and $R_{12}$ together with the nitrogen atom form het;

wherein the alkyl substituents of $R_{11}$ and $R_{12}$ may be unsubstituted or substituted by one or more substituents selected from $C_1$-$C_{10}$alkyl, halogen, OH, —O—$C_1$-$C_6$alkyl, —S—$C_1$-$C_6$alkyl or —CF$_3$;

substituted cycloalkyl substituents of $R_{11}$ and $R_{12}$ are substituted by one or more substituents selected from a $C_1$-$C_{10}$ alkene; $C_1$-$C_6$alkyl; halogen; OH; —O—$C_1$-$C_6$alkyl; —S—$C_1$-$C_6$alkyl or —CF$_3$; and substituted phenyl or aryl of $R_{11}$ and $R_{12}$ are substituted by one or more substituents selected from halogen; hydroxy; $C_1$-$C_4$ alkyl; $C_1$-$C_4$ alkoxy; nitro; —CN; —O—C(O)—$C_1$-$C_4$alkyl and —C(O)—O—$C_1$-$C_4$-aryl, or pharmaceutically acceptable salts thereof.

The present invention also related to the use of compound of formula I in the treatment of proliferative diseases, especially those dependent on the binding of the Smac protein to Inhibitor of Apoptosis Proteins (IAPs), or for the manufacture of pharmaceutical compositions for use in the treatment of said diseases, methods of use of compounds of formula (I) in the treatment of said diseases, pharmaceutical preparations comprising compounds of formula (I) for the treatment of said diseases, compounds of formula (I) for use in the treatment of said diseases.

The general terms used hereinbefore and hereinafter preferably have within the context of this disclosure the following meanings, unless otherwise indicated:

"Aryl" is an aromatic radical having 6 to 14 carbon atoms, which may be fused or unfused, and which is unsubstituted or substituted by one or more, preferably one or two substituents, wherein the substituents are as described below. Preferred "aryl" is phenyl, naphthyl or indanyl.

"Het" refers to heteroaryl and heterocyclic rings and fused rings containing aromatic and non-aromatic heterocyclic rings. "Het" is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S. Suitable het substituents include unsubstituted and substituted pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, 1,4-oxathiapane, furyl, thienyl, pyrrole, pyrazole, triazole, 1,2,3-triazole, tetrazolyl, oxadiazole, thiophene, imidazol, pyrrolidine, pyrrolidone, thiazole, oxazole, pyridine, pyrimidine, isoxazolyl, pyrazine, quinoline, isoquinoline, pyridopyrazine, pyrrolopyridine, furopyridine, indole, benzofuran, benzothiofuran, benzindole, benzoxazole, pyrroloquinoline, and the like. The het substituents are unsubstituted or substituted on a carbon atom by halogen, especially fluorine or chlorine, hydroxy, $C_1$-$C_4$ alkyl, such as methyl and ethyl, $C_1$-$C_4$ alkoxy, especially methoxy and ethoxy, nitro, —O—C(O)—$C_1$-$C_4$alkyl or —C(O)—O—$C_1$-$C_4$alkyl or on a nitrogen by $C_1$-$C_4$ alkyl, especially methyl or ethyl, —O—C(O)—$C_1$-$C_4$alkyl or —C(O)—O—$C_1$-$C_4$alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazolyl, and the like.

Halogen is fluorine, chlorine, bromine or iodine, especially fluorine and chlorine.

Unless otherwise specified "alkyl" includes straight or branched chain alkyl, such as methyl, ethyl, n-propyl, isopropyl, n-butyl, sec-butyl, tert-butyl, n-pentyl and branched pentyl, n-hexyl and branched hexyl, and the like.

A "cycloalkyl" group means $C_3$ to $C_{10}$cycloalkyl having 3 to 8 ring carbon atoms and may be, for example, cyclopropyl, cyclobutyl, cyclopentyl, cyclohexyl, cycloheptyl or cyclooctyl. Preferably, cycloalkyl is cycloheptyl. The cycloalkyl group may be unsubstituted or substituted with any of the substituents defined below, preferably halo, hydroxy or $C_1$-$C_4$ alkyl such as methyl.

The amino acid residues include a residue of a standard amino acid, such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The amino acid residues also include the side chains of uncommon and modified amino acids. Uncommon and modified amino acids are known to those of skill in the art (see for example G. B. Fields, Z. Tiam and G Barany; Synthetic Peptides A Users Guide, University of Wisconsin Biochemistry Center, Chapter 3, (1992)) and include amino acids such as 4-hydroxyproline, 5-hydroxylysine, desmosine, beta-alanine, alpha, gamma- and beta-aminobutric acid, homocysteine, homoserine, citrulline, ornithine, 2- or 3-amino adipic acid, 6-aminocaproic acid, 2- or 3-aminoisobutric acid, 2,3-diaminopropionic acid, diphenylalanine, hydroxyproline and the like. If the side chain of the amino acid residue contains a derivatizable group, such as COOH, —OH or amino, the side chain may be derivatized by a substituent that reacts with the derivatizable group. For example, acidic amino acids, like aspartic and glutamic acid, or hydroxy substituted side chains, like those of serine or threonine, may be derivatized to form an ester, or amino side chains may form amide or alkylamino derivatives. In particular, the derivative may be a substituent that facilitates transport across a cell membrane. In addition, any carboxylic acid group in the amino acid residue, for example, an alpha carboxylic acid group, may be derivatized as discussed above to form an ester or amide.

Substituents that facilitate transport of the molecule across a cell membrane are known to those of skill in the medicinal chemistry arts (see, for example, Gangewar S., Pauletti G. M., Wang B., Siahaan T. J., Stella V. J., Borchardt R. T., *Drug Discovery Today*, vol. 2. p 148-155 (1997) and Bundgaard H. and Moss J., *Pharmaceutical Research*, vol. 7, p 885 (1990)). Generally, such substituents are lipophilic substituents. Such lipophilic substituents include a $C_6$-$C_{30}$ alkyl which is saturated, monounsaturated, polyunsaturated, including methylene-interrupted polyene, phenyl, phenyl which substituted by one or two $C_1$-$C_8$ alkyl groups, $C_5$-$C_9$ cycloalkyl, $C_5$-$C_9$ cycloalkyl which is substituted by one or two $C_1$-$C_8$ alkyl groups, —$X_1$-phenyl, —$X_1$-phenyl which is substituted in the phenyl ring by one or two $C_1$-$C_8$ alkyl groups, $X_1$—$C_5$-$C_9$ cycloalkyl or $X_1$—$C_5$-$C_9$ cycloalkyl which is substituted by one or two $C_1$-$C_8$ alkyl groups; where $X_1$ is $C_1$-$C_{24}$ alkyl which is saturated, monounsaturated or polyunsaturated and straight or branched chain.

Unsubstituted is intended to mean that hydrogen is the only substituent.

Any of the above defined aryl, het, alkyl, cycloalkyl, or heterocyclic groups may be unsubstituted or independently substituted by up to four, preferably one, two or three substituents, selected from the group consisting of: halo (such as Cl or Br); hydroxy; lower alkyl (such as $C_1$-$C_3$ lower alkyl); lower alkyl which may be substituted with any of the substituents defined herein; lower alkenyl; lower alkynyl; lower alkanoyl; alkoxy (such as methoxy); aryl (such as phenyl or benzyl); substituted aryl (such as fluoro phenyl or methoxy phenyl); amino; mono- or disubstituted amino; amino lower alkyl (such as dimethylamino); acetyl amino; amino lower alkoxy (such as ethoxyamine); nitro; cyano; cyano lower alkyl; carboxy; esterified carboxy (such as lower alkoxy carbonyl e.g. methoxy carbonyl); n-propoxy carbonyl or iso-propoxy carbonyl; alkanoyl; benzoyl; carbamoyl; N-mono- or N,N-disubstituted carbamoyl; carbamates; alkyl carbamic acid esters; amidino; guanidine; urea; ureido; mercapto; sulfo; lower alkylthio; sulfoamino; sulfonamide; benzosulfonamide; sulfonate; sulfanyl lower alkyl (such as methyl sulfanyl); sulfoamino; substituted or unsubstituted sulfonamide (such as benzo sulfonamide); substituted or unsubstituted sulfonate (such as chloro-phenyl sulfonate); lower alkylsulfinyl; phenylsulfinyl; phenyl-lower alkylsulfinyl; alkylphenylsulfinyl; lower alkanesulfonyl; phenylsulfonyl; phenyl-lower alkylsulfonyl; alkylphenylsulfonyl; halogen-lower alkylmercapto; halogen-lower alkylsulfonyl; such as especially trifluoromethane sulfonyl; phosphono (—P(=O)(OH)$_2$); hydroxy-lower alkoxy phosphoryl or di-lower alkoxyphosphoryl; substituted urea (such as 3-trifluoro-methyl-phenyl urea); alkyl carbamic acid ester or carbamates (such as ethyl-N-phenyl-carbamate) or —NR$_4$R$_5$, wherein R$_4$ and R$_5$ can be the same or different and are independently H; lower alkyl (e.g. methyl, ethyl or propyl); or R$_4$ and R$_5$ together with the N atom form a 3- to 8-membered heterocyclic ring containing 1-4 nitrogen, oxygen or sulfur atoms (e.g. piperazinyl, pyrazinyl, lower alkyl-piperazinyl, pyridyl, indolyl, thiophenyl, thiazolyl, n-methyl piperazinyl, benzothiophenyl, pyrrolidinyl, piperidino or imidazolinyl) where the heterocyclic ring may be substituted with any of the substituents defined herein.

Preferably the above mentioned alkyl, cycloalkyl, aryl or het groups may be substituted by halogen, carbonyl, thiol, S(O), S(O$_2$), —OH, —SH, —OCH$_3$, —SCH$_3$, —CN, —SCN or nitro.

Where the plural form is used for compounds, salts, pharmaceutical preparations, diseases and the like, this is intended to mean also a single compound, salt, or the like.

It will be apparent to one of skill in the art when a compound of the invention can exist as a salt form, especially as an acid addition salt or a base addition salt. When a compound can exist in a salt form, such salt forms are included within the scope of the invention. Although any salt form may be useful in chemical manipulations, such as purification procedures, only pharmaceutically acceptable salts are useful for pharmaceutically products.

Pharmaceutically acceptable salts include, when appropriate, pharmaceutically acceptable base addition salts and acid addition salts, for example, metal salts, such as alkali and alkaline earth metal salts, ammonium salts, organic amine addition salts, and amino acid addition salts, and sulfonate salts. Acid addition salts include inorganic acid addition salts such as hydrochloride, sulfate and phosphate, and organic acid addition salts such as alkyl sulfonate, arylsulfonate, acetate, maleate, fumarate, tartrate, citrate and lactate. Examples of metal salts are alkali metal salts, such as lithium salt, sodium salt and potassium salt, alkaline earth metal salts such as magnesium salt and calcium salt, aluminum salt, and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

In view of the close relationship between the compounds in free form and those in the form of their salts, including those salts that can be used as intermediates, for example in the purification or identification of the compounds, tautomers or tautomeric mixtures and their salts, any reference to the compounds hereinbefore and hereinafter especially the compounds of the formula I, is to be understood as referring also to the corresponding tautomers of these compounds, especially of compounds of the formula I, tautomeric mixtures of these compounds, especially of compounds of the formula I, or salts of any of these, as appropriate and expedient and if not mentioned otherwise.

Any asymmetric carbon atom may be present in the (R)-, (S)- or (R,S)-configuration, preferably in the (R)- or (S)-configuration. Substituents at a ring at atoms with saturated bonds may, if possible, be present in cis- (=Z-) or trans (=E-) form. The compounds may thus be present as mixtures of isomers or preferably as pure isomers, preferably as enantiomer-pure diastereomers or pure enantiomers.

Preferred embodiments according to the invention:

In the following preferred embodiments, general expression can be replaced by the corresponding more specific definitions provided above and below, thus yielding stronger preferred embodiments of the invention.

Preferred is the USE of compounds of the formula I or pharmaceutically acceptable salts thereof, where the disease to be treated is a proliferative disease depending on binding of the Smac protein to inhibitor of Apoptosis Proteins (IAPS).

An embodiment of the present invention relates to compounds of the formula (I)

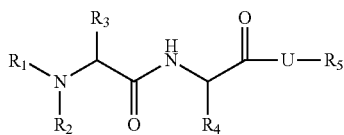

(I)

wherein
$R_1$ is H; $C_1$-$C_4$ alkyl; $C_1$-$C_4$ alkenyl; $C_1$-$C_4$ alkynyl or cycloalkyl which are unsubstituted or substituted by one or more substituents selected from halogen, —OH, —SH, —OCH$_3$, —SCH$_3$, —CN, —SCN and nitro;
$R_2$ is H; $C_1$-$C_4$alkyl; $C_1$-$C_4$ alkenyl; $C_1$-$C_4$ alkynyl or cycloalkyl which are unsubstituted or substituted by one or more substituents selected from halogen, —OH, —SH, —OCH$_3$, —SCH$_3$, —CN, —SCN and nitro;
$R_3$ is H; —CF$_3$; —C$_2$F$_5$; $C_1$-$C_4$ alkyl; $C_1$-$C_4$ alkenyl; $C_1$-$C_4$ alkynyl; —CH$_2$—Z or $R_2$ and $R_3$ together with the nitrogen form a het;
Z is H; —OH; F; Cl; —CH$_3$; —CF$_3$; —CH$_2$Cl; —CH$_2$F or —CH$_2$OH;
$R_4$ is $C_1$-$C_{16}$ straight or branched alkyl; $C_1$-$C_{16}$ alkenyl; $C_1$-$C_{16}$ alkynyl; or —$C_3$-$C_{16}$ cycloalkyl; —(CH$_2$)$_{1-6}$—Z$_1$; —(CH$_2$)$_{0-6}$-phenyl; and —(CH$_2$)$_{0-6}$-het, wherein alkyl, cycloalkyl and phenyl are unsubstituted or substituted;
$Z_1$ is —N(R$_8$)—C(O)—C$_1$-C$_{10}$alkyl; —N(R$_8$)—C(O)—(CH$_2$)$_{1-6}$—C$_3$-C$_7$cycloalkyl; —N(R$_8$)—C(O)—(CH$_2$)$_{0-6}$-phenyl; —N(R$_8$)—C(O)—(CH$_2$)$_{1-6}$-het; —C(O)—N(R$_9$)(R$_{10}$); —C(O)—O—C$_1$-C$_{10}$alkyl; —C(O)—O—(CH$_2$)$_{1-6}$—C$_3$-C$_7$cycloalkyl; —C(O)—O—(CH$_2$)$_{0-6}$-phenyl; —C(O)—O—(CH$_2$)$_{1-6}$-het; —O—C(O)—C$_1$-C$_{10}$alkyl; —O—C(O)—(CH$_2$)$_{1-6}$—C$_3$-C$_7$cycloalkyl; —O—C(O)—(CH$_2$)$_{0-6}$-phenyl; —O—C(O)—(CH$_2$)$_{1-6}$-het, wherein alkyl, cycloalkyl and phenyl are unsubstituted or substituted;
het is a 5-7 membered heterocyclic ring containing 1-4 heteroatoms selected from N, O and S, or an 8-12 membered fused ring system including at least one 5-7 membered heterocyclic ring containing 1, 2 or 3 heteroatoms selected from N, O, and S, which heterocyclic ring or fused ring system is unsubstituted or substituted on a carbon atom by halogen, hydroxy, $C_1$-$C_4$alkyl, $C_1$-$C_4$ alkoxy, nitro, —O—C(O)—C$_1$-C$_4$alkyl or —C(O)—O—C$_1$-C$_4$-alkyl or on a nitrogen by $C_1$-$C_4$ alkyl, —O—C(O)—C$_1$-$C_4$alkyl or —C(O)—O—C$_1$-$C_4$alkyl;
$R_8$ is H, —CH$_3$, —CF$_3$, —CH$_2$OH or —CH$_2$Cl;
$R_9$ and $R_{10}$ are each independently H; $C_1$-$C_4$ alkyl; $C_3$-$C_7$cycloalkyl; —(CH$_2$)$_{1-6}$—C$_3$-C$_7$cycloalkyl; —(CH$_2$)$_{0-6}$-phenyl; wherein alkyl, cycloalkyl and phenyl are unsubstituted or substituted, or $R_9$ and $R_{10}$ together with the nitrogen form het;
$R_5$ is H; $C_1$-$C_{10}$-alkyl; $C_3$-$C_7$cycloalkyl; —(CH$_2$)$_{1-6}$—C$_3$-C$_7$cycloalkyl; —C$_1$-C$_{10}$alkyl-aryl; —(CH$_2$)$_{0-6}$—C$_3$-C$_7$cycloalkyl-(CH$_2$)$_{0-6}$-phenyl; —(CH$_2$)$_{0-4}$CH—((CH$_2$)$_{1-4}$-phenyl)$_2$; —(CH$_2$)$_{0-6}$—CH(phenyl)$_2$; —(CH$_2$)$_{0-6}$—C(O)phenyl-indanyl; aryl —C(O)—C$_1$-C$_{10}$alkyl; —C(O)—(CH$_2$)$_{1-6}$—C$_3$-C$_7$cycloalkyl; —C(O)—(CH$_2$)$_{0-6}$-phenyl; —(CH$_2$)$_{0-6}$-het; —C(O)—(CH$_2$)$_{1-6}$-het; or $R_5$ is a residue of an amino acid, wherein alkyl, cycloalkyl, phenyl and aryl are unsubstituted or substituted;
U is a as shown in structure II:

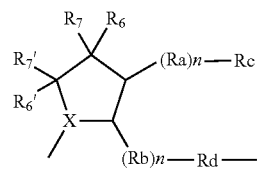

II wherein
n=0-5;
X is —CH or N;
Ra and Rb are independently an O, S, or N atom or $C_{0-8}$ alkyl wherein one or more of the carbon atoms in the alkyl chain may be replaced by a heteroatom selected from O, S or N, and where the alkyl may be unsubstituted or substituted;
Rd is selected from:
(a) -Re-Q-(Rf)$_p$(Rg)$_q$; or
(b) Ar$_1$-D-Ar$_2$;
Rc is H or Rd and Rc together form cycloalkyl or het; where if Rd and Rc form a cycloalkyl or heteroring, $R_5$ is attached to the formed ring at a C or N atom;
p and q are independently 0 or 1;
Re is C$_{1-8}$alkyl, or alkylidene, preferably methylidene, and Re may be unsubstituted or substituted;
Q is N, O, S, S(O), or S(O)$_2$;
Ar$_1$ and Ar$_2$ are substituted or unsubstituted aryl or het;
Rf and Rg are each independently H; —C$_1$-C$_{10}$ alkyl; C$_1$-C$_{10}$alkylaryl; —OH; —O—C$_1$-C$_{10}$alkyl; —(CH$_2$)$_{0-6}$—C$_3$-C$_7$cycloalkyl; —O—(CH$_2$)$_{0-6}$-aryl; phenyl; aryl; phenyl-phenyl; —(CH$_2$)$_{1-6}$-het; —O—(CH$_2$)$_{1-6}$-het; —OR$_{11}$; —C(O)—R$_{11}$; —C(O)—N(R$_{11}$)(R$_{12}$); —N(R$_{11}$)(R$_{12}$); —S—R$_{11}$; —S(O)—R$_{11}$; —S(O)$_2$—R$_{11}$; —S(O)$_2$—NR$_{11}$R$_{12}$; —NR$_{11}$—S(O)$_2$—R$_{12}$; S—C$_1$-C$_1$-alkyl; aryl-C$_1$-C$_4$ alkyl; het-C$_1$-C$_4$ alkyl wherein alkyl, cycloalkyl, het and aryl are unsubstituted or substituted; —SO$_2$—C$_1$-C$_2$ alkyl; —SO$_2$—C$_1$-C$_2$ alkylphenyl; —O—C$_1$-C$_4$ alkyl; or R$_g$ and R$_f$ form a ring selected from het or aryl;
D is —CO—; —C(O)—C$_{1-7}$ alkylene or arylene; —CF$_2$—; —O—; —S(O)$_r$ where r is 0-2; 1,3dioaxolane; or C$_{1-7}$ alkyl-OH; where alkyl, alkylene or arylene may be unsubstituted or substituted with one or more halogens, OH, —O—C$_1$-C$_6$alkyl, —S—C$_1$-C$_6$alkyl or —CF$_3$; or D is —N(Rh) wherein Rh is H; C$_{1-7}$ alkyl (unsub or substituted); aryl; —O(C$_{1-7}$cycloalkyl) (unsub or substituted); C(O)—C$_1$-C$_{10}$alkyl; C(O)—C$_o$-C$_{10}$alkyl-aryl; C—O—C$_1$-C$_{10}$alkyl; C—O—C$_o$-C$_{10}$alkyl-aryl or SO$_2$—C$_1$-C$_{10}$-alkyl; SO$_2$—(C$_o$-C$_{10}$-alkylaryl);

$R_6$, $R_7$, $R'_6$ and $R'_7$ are each independently H; —$C_1$-$C_{10}$alkyl; —$C_1$-$C_{10}$ alkoxy; aryl-$C_1$-$C_{10}$ alkoxy; —OH; —O—$C_1$-$C_{10}$alkyl; —$(CH_2)_{0-6}$—$C_3$-$C_7$cycloalkyl; —O—$(CH_2)_{0-6}$-aryl; phenyl; —$(CH_2)_{1-6}$-het; —O—$(CH_2)_{1-6}$-het; —$OR_{11}$; —C(O)—$R_{11}$; —C(O)—N($R_{11}$)($R_{12}$); —N($R_{11}$)($R_{12}$); —S—$R_{11}$; —S(O)—$R_{11}$; —S(O)$_2$—$R_{11}$; —S(O)$_2$—N$R_{11}R_{12}$; —N$R_{11}$—S(O)$_2$—$R_{12}$; wherein alkyl, cycloalkyl and aryl are unsubstituted or substituted; and $R_6$, $R_7$, $R'_6$ and $R'_7$ can be united to form a ring system;

$R_{11}$ and $R_{12}$ are independently H; $C_1$-$C_{10}$alkyl; —$(CH_2)_{0-6}$—$C_3$-$C_7$cycloalkyl; —$(CH_2)_{0-6}$—$(CH)_{0-1}$(aryl)$_{1-2}$; —C(O)—$C_1$-$C_{10}$alkyl; —C(O)—$(CH_2)_{1-6}$—$C_3$-$C_7$cycloalkyl; —C(O)—O—$(CH_2)_{0-6}$-aryl; —C(O)—$(CH_2)_{0-6}$—O-fluorenyl; —C(O)—NH—$(CH_2)_{0-6}$-aryl; —C(O)—$(CH_2)_{0-6}$-aryl; —C(O)—$(CH_2)_{1-6}$-het; —C(S)—$C_1$-$C_{10}$alkyl; —C(S)—$(CH_2)_{1-6}$—$C_3$-$C_7$cycloalkyl; —C(S)—O—$(CH_2)_{0-6}$-aryl; —C(S)—$(CH_2)_{0-6}$—O-fluorenyl; —C(S)—NH—$(CH_2)_{0-6}$-aryl; —C(S)—$(CH_2)_{0-6}$-aryl; —C(S)—$(CH_2)_{1-6}$-het; wherein alkyl, cycloalkyl and aryl are unsubstituted or substituted; or $R_{11}$ and $R_{12}$ are a substituent that facilitates transport of the molecule across a cell membrane; or $R_{11}$ and $R_{12}$ together with the nitrogen are het; aryl of $R_{11}$ and $R_{12}$ can be phenyl, naphthyl, or indanyl which is unsubstituted or substituted;

alkyl of $R_{11}$ and $R_{12}$ may be unsubstituted or substituted by one or more substituents selected from a $C_1$-$C_{10}$ alkene, halogen, OH, —O—$C_1$-$C_6$ alkyl, —S—$C_1$-$C_6$ alkyl and —$CF_3$; cycloalkyl of $R_{11}$ and $R_{12}$ may be unsubstituted or substituted by one or more selected from a $C_1$-$C_{10}$ alkene, one or more halogens, $C_1$-$C_6$ alkyl, halogen, OH, —O—$C_1$-$C_6$ alkyl, —S—$C_1$-$C_6$ alkyl or —$CF_3$; and phenyl or aryl of $R_{11}$ and $R_{12}$ may be unsubstituted or substituted by one or more substituents selected from halogen, hydroxy, $C_1$-$C_4$ alkyl, $C_1$-$C_4$ alkoxy, nitro, —CN, —O—C(O)—$C_1$-$C_4$ alkyl and —C(O)—O—$C_1$-$C_4$-aryl;

or pharmaceutically acceptable salts thereof.

A further embodiment the present invention relates to the use of compound of formula I in the treatment of proliferative diseases, especially those dependent on the binding of the Smac protein to Inhibitor of Apoptosis Proteins (IAPs), or for the manufacture of pharmaceutical compositions for use in the treatment of said diseases, methods of use of compounds of formula (I) in the treatment of said diseases, pharmaceutical preparations comprising compounds of formula (I) for the treatment of said diseases, compounds of formula (I) for use in the treatment of said diseases.

One embodiment of the present invention relates to compounds of the formula (I) wherein $R_1$ and $R_2$ are independently H or substituted or unsubstituted $C_1$-$C_4$alkyl;

$R_4$ is $C_1$-$C_{16}$ straight or branched alkyl, or $C_3$-$C_{10}$cycloalkyl, wherein the alkyl or cycloalkyl may be unsubstituted or substituted;

$R_5$ is H; $C_1$-$C_{10}$alkyl; $C_1$-$C_{10}$alkyl-aryl; —C(O)—$(CH_2)_{0-6}$-Phenyl; —$(CH_2)_{0-6}$—C(O)-Phenyl; aryl; indanyl; naphthyl or $R_5$ is a residue of an amino acid, wherein the alkyl or aryl substituents are unsubstituted or substituted;

U is as shown in structure II:

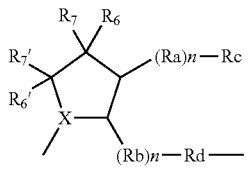

II wherein n=0-5;

X is —CH or N;

Ra and Rb are independently an O, S, or N atom or $C_{0-8}$ alkyl wherein one or more of the carbon atoms in the alkyl chain may be replaced by a heteroatom selected from O, S or N, and where the alkyl may be unsubstituted or substituted;

Rd is selected from
(a) -Re-Q-(Rf)$_p$(Rg)$_q$; or
(b) Ar$_1$-D-Ar$_2$;

Rc is H or Rc and Rd together form cycloalkyl or het; where if Rd and Rc form a cycloalkyl or heteroring, $R_5$ is attached to the formed ring at a C or N atom;

p and q are independently 0 or 1;

Re is $C_{1-8}$ alkyl, or methylidene which may be unsubstituted or substituted;

Q is N, O, S, S(O), or S(O)$_2$;

Ar$_1$ and Ar$_2$ are substituted or unsubstituted aryl or het;

Rf and Rg are each independently H or substituted or unsubstituted $C_0$-$C_{10}$alkyl; $C_1$-$C_{10}$alkylaryl; aryl-$C_1$-$C_{10}$alkyl; het-$C_1$-$C_{10}$alkyl —C(O)—$C_1$-$C_4$-alkyl-phenyl; —C(O)—$C_1$-$C_4$-alkyl; —$SO_2$—$C_1$-$C_2$ alkyl; —$SO_2$—$C_1$-$C_2$ alkylphenyl; —O—$C_1$-$C_4$-alkyl;

D is —C(O)—; $C_{1-7}$ alkylene or arylene; —O—, or —S(O)$_r$ where r is 0-2; where alkyl, alkylene or arylene which may be unsubstituted or substituted with one or more halogens; —OH; —O—$C_1$-$C_6$ alkyl; —S—$C_1$-$C_6$ alkyl or —$CF_3$; or D is NRh wherein Rh is H; $C_{1-7}$ alkyl (unsubstituted or substituted); aryl; —$OC_{1-7}$cycloalkyl (unsubstituted or substituted); —CO—$C_{0-10}$ alkyl or aryl or $SO_2$—$C_{0-10}$-alkyl or aryl; and $R_6$, $R_7$, $R'_6$ and $R'_7$ are each independently H, —$C_1$-$C_{10}$alkyl, or —OH, alkoxy, or aryloxy;

or pharmaceutically acceptable salts thereof.

In a further embodiment, U is a bicyclic saturated or unsaturated ring system, consisting of all carbon skeleton or with one or more heteroatoms such as O, N, S but preferably as shown in structure III:

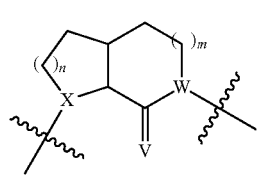

III wherein wherein any of the ring carbon atoms can be unsubstituted or substituted with any of the substituted defined above for $R_6$, $R_7$, $R_6$', and $R_7$';

X is CH or N;

V is O, $F_2$, $Cl_2$, $Br_2$, $I_2$, S, YH, $H_2$, NH, or $C_1$-$C_4$ alkyl;

W is —CH, or —N;

n is 0-3; and m is 0-3.

In a preferred embodiment the ring atoms may be substituted with substituents independently selected from halo, H, OH, lower alkyl or lower alkoxy, wherein alkyl or alkoxy are unsubstituted or substituted by halogen, OH, lower alkyl or lower alkoxy.

In a further embodiment, U of formula II or III together with $R_5$ farm a fused ring system.

Especially preferred is a compound of formula (I) wherein $R_1$ and $R_3$ are preferably methyl or ethyl;

$R_2$ is especially H; methyl; ethyl; chloromethyl; dichloromethyl or trifluoromethyl;

$R_4$ is —$C_1$-$C_4$ alkyl; —$C_3$-$C_7$ cycloalkyl; —$(CH_2)_{1-6}$cycloalkyl; or —$(CH_2)_{0-6}$aryl. $R_4$ is particularly ethyl; propyl; isopropyl; t-butyl; cyclopentyl; or cyclohexyl; —$CH_2$-cyclopentyl; —$CH_2$-cyclohexyl or —$CH_2$-phenyl.

$R_5$ is —$C_1$-$C_4$alkyl-phenyl; —C(O)—$C_1$-$C_4$ alkyl-phenyl; —$C_1$-$C_4$ alkyl-C(O)-phenyl or aryl; $R_5$ is particularly phenylmethyl, phenylethyl and phenylpropyl; indanyl, naphthyl; —C(O)—$CH_2$-phenyl or —$CH_2$—C(O)-phenyl;

$R_6$ and $R_7$ are H or methyl;

U has the structure of formula III:

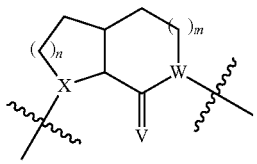

III wherein
wherein any of the ring carbon atoms can be unsubstituted or substituted with any of the substituted defined above for $R_6$, $R_7$, $R_6'$ and $R_7'$;
X is N;
V is O or $H_2$;
W is —N;
n is 1; and
m is 1 or 2.

Especially preferred is a compound of formula (I) wherein
$R_1$ and $R_3$ are preferably methyl or ethyl;
$R_2$ is H;
$R_4$ is $C_1$-$C_4$alkyl; $C_{3-7}$cycloalkyl; $C_1$-$C_7$ cycloalkyl-$C_1$-$C_7$alkyl; phenyl-$C_1$-$C_7$alkyl or aryl. $R_4$ is particularly methyl; ethyl; butyl; isopropyl; t-butyl; or cyclohexyl; —$CH_2$-cyclopentyl; —$CH_2$-cyclohexyl; —$CH_2$-cyclopropyl; phenyl or —$CH_2$-phenyl;
$R_5$ is —$C_1$-$C_4$ alkyl-phenyl; —C(O)—$C_1$-$C_4$ alkyl-phenyl; —$C_1$-$C_4$ alkyl-C(O)-phenyl or aryl. $R_5$ is particularly phenylethyl; indanyl, naphthyl; —C(O)—$CH_2$-phenyl; —$CH_2$—C(O)-phenyl or ($CF_3$O)phenylethyl;
$R_6$, $R'_6$, $R_7$ and $R'_7$ are H;
U has the structure of formula III wherein
wherein any of the ring carbon atoms can be unsubstituted or substituted with any of the substituted defined above for $R_6$, $R_7$, $R_6'$ and $R_7'$;
X is N;
V is O or $H_2$;
W is —N;
n is 1; and
m is 1 or 2.

Another embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$alkyl or $C_3$-$C_7$ cycloalkyl particularly isopropyl, t-butyl, cyclopentyl, or cyclohexyl;
$R_5$ is H;
U has the structure of formula II wherein
X is N;
$R_6$, $R'_6$, $R_7$, and $R'_7$ are H;
n is O;
Rc is H;

$Ar_1$ and $Ar_2$ are substituted or unsubstituted phenyl or het particularly tetrazolyl, 1,2,3-triazole, pyrazole, oxazole, pyrrolyl, triazine, pyrimidine, imidazol, oxadiazol; and and D is $C_1$ alkyl which may optionally be substituted with halo, especially F.

Another embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$alkyl; $C_3$-$C_7$ cycloalkyl; $C_1$-$C_7$ cycloalkyl-$C_1$-$C_7$alkyl; phenyl-$C_1$-$C_7$alkyl or aryl. $R_4$ is particularly methyl, ethyl, butyl, isopropyl, t-butyl, or cyclohexyl; —$CH_2$-cyclopentyl, —$CH_2$-cyclohexyl; —$CH_2$-cyclopropyl; phenyl or —$CH_2$-phenyl;
$R_5$ is H;
U has the structure of formula II wherein
X is N;
$R_6$, $R'_6$, $R_7$, and $R'_7$ are H; or $R_6$ is —C(O)—$C_1$-$C_4$ alkyl-phenyl and $R'_6$, $R_7$, and $R'_7$ are H;
n is O;
Rc is H;
$Ar_1$ and $Ar_2$ are substituted or unsubstituted phenyl or het, particularly triazine, pyrimidine, pyridine, oxazole, 2,4-difluorophenyl, Cl-phenyl or fluorophenyl; and D is N(Rh), where Rh is H, Me, —CHO, —$SO_2$, —C(O), —CHOH, —$CF_3$ or —$SO_2CH_3$.

Another embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$ alkyl; $C_3$-$C_7$cycloalkyl; $C_1$-$C_7$cycloalkyl-$C_1$-$C_7$alkyl; phenyl-$C_1$-$C_7$alkyl or aryl. $R_4$ is particularly methyl, ethyl, butyl, isopropyl, t-butyl, or cyclohexyl; —$CH_2$-cyclopentyl, —$CH_2$-cyclohexyl; —$CH_2$-cyclopropyl; phenyl or —$CH_2$-phenyl;
$R_5$ is H;
U has the structure of formula II wherein
X is N;
$R_6$, $R'_6$, $R_7$, and $R'_7$ are H;
n is O;
Rc is H;
$Ar_1$ and $Ar_2$ are substituted or unsubstituted phenyl or het particularly pyrimidine, pyridine, oxazole, 2-methyloxazole; and D is —O—.

Another embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$ alkyl or $C_3$-$C_7$cycloalkyl particularly isopropyl, t-butyl, cyclopentyl, or cyclohexyl;
$R_5$ is H;
U has the structure of formula II wherein
X is N;
$R_6$, $R'_6$, $R_7$, and $R'_7$ are H;
n is O;
Rc is H;
$Ar_1$ and $Ar_2$ are substituted or unsubstituted phenyl or het; and D is S, S(O), or $S(O)_2$.

Another embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;

$R_4$ is $C_1$-$C_4$ alkyl or $C_3$-$C_7$cycloalkyl particularly isopropyl, t-butyl, cyclopentyl, or cyclohexyl;
$R_5$ is H;
U has the structure of formula II wherein
X is N;
$R_6$, $R'_6$, $R_7$, and $R'_7$ are H;
n is O;
Rc is H;
$Ar_1$ and $Ar_2$ are substituted or unsubstituted phenyl or het, particularly oxazole, thiazole and ozadiazole;
and D is C(O), or 1,3-dioxolane.

Another embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$alkyl or $C_3$-$C_7$cycloalkyl particularly isopropyl, t-butyl, cyclopentyl, or cyclohexyl;
$R_5$ is H or phenyl $C_1$-$C_{10}$alkyl such as phenylethyl;
U has the structure of formula II wherein
X is N;
$R_6$, $R'_6$, $R_7$, and $R'_7$ are H;
n is O;
Rc and Rd are a heterocyclic ring, particularly pyrrolidine; pyrrolidin-2-one; or pyrrolidin-3-one.

Another embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$alkyl or $C_3$-$C_7$cycloalkyl particularly isopropyl, t-butyl, cyclopentyl, or cyclohexyl;
$R_5$ is H, indanyl or phenyl;
U has the structure of formula II wherein
X is N;
Q is O;
$R_6$, $R'_6$, $R_7$, and $R'_7$ are H;
n is O;
Re is $C_1$ alkyl; and
p and q are 0.

A further embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$ alkyl or $C_3$-$C_7$cycloalkyl particularly isopropyl, t-butyl, cyclopentyl, or cyclohexyl;
$R_5$ is H, indanyl or phenyl;
U has the structure of formula II wherein
X is N;
Q is N;
$R_6$, $R'_6$, $R_7$, and $R'_7$ are H;
n is O;
Re is $C_1$ alkyl; and
$R_g$ is H $C_1$-$C_8$ alkyl, methyl, ethyl, hexyl, heptyl, octyl; or $CH_2CF_3$; or aryl-$C_1$-$C_4$ alkyl particularly phenylethyl, furanylethyl; $C_3$-$C_7$cycloalkyl particularly cyclohexyl; ethylphenyl; —C(O)—$C_1$-$C_4$ alkyl-phenyl; —C(O)—$C_1$-$C_4$ alkyl; —$C_1$-$C_4$ alkyl-aryl particularly —$CH_2$-phenyl; —$CH_2$-thiophene, —$CH_2$-furan, —$CH_2$-pyrrolidinyl, —$CH_2$-imidazole, —$CH_2$-triazole, —$CH_2$-imidazole;
and $R_f$ is $C_1$-$C_2$ alkyl; $C_1$-$C_2$ alkylphenyl; —$SO_2$—$C_1$-$C_2$ alkyl; —$SO_2$—$C_1$-$C_2$ alkylphenyl; —O—$C_1$-$C_4$ alkyl particularly O-ethyl; phenyl-phenyl, 1,2,3,4-tetrahydronapthalene and indanyl.

A further embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$ alkyl or $C_3$-$C_7$cycloalkyl particularly isopropyl, t-butyl, cyclopentyl, or cyclohexyl;
$R_5$ is H, indanyl or phenyl;
U has the structure of formula II wherein
X is N;
Q is N;
$R_6$, $R'_6$, $R_7$, and $R'_7$ are H;
n is O;
Re is C alkyl; and
$R_g$ and $R_f$ form a ring selected from het or aryl particularly 2,3,4,5-tetrahydrobenzo[c]azepine; 1,2,3,4 tetrahydroquinoline; indanyl which may be substituted with $C_1$-$C_4$alkylphenyl A further embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$alkyl or $C_3$-$C_7$cycloalkyl particularly isopropyl, t-butyl, cyclopentyl, or cyclohexyl;
$R_5$ is phenyl;
U has the structure of formula II wherein
X is N;
Q is O, S, S(O) or S(O)$_2$;
$R_6$, $R'_6$, $R_7$, and $R'_7$ are H;
n is O;
Re is $C_1$ alkyl;
q is 0;
Rc is H;
and $R_f$ is $C_2$ alkyl.

A further embodiment is directed to a compound of formula (I) wherein
$R_1$ and $R_3$ are preferably methyl or ethyl;
$R_2$ is especially H, methyl, ethyl, chloromethyl, dichloromethyl or trifluoromethyl;
$R_4$ is $C_1$-$C_4$ alkyl or $C_3$-$C_7$cycloalkyl particularly isopropyl, t-butyl, cyclopentyl, or cyclohexyl;
$R_5$ is phenyl;
U has the structure of formula II wherein
X is N;
Q is N;
$R_6$, $R'_6$, $R_7$, and $R'_7$ are H;
n is O;
Re is CH;
q is 0;
Rc is H;
and $R_f$ is O$C_1$ alkyl.

In a particularly important embodiment of the present invention, $R_3$ and $R_4$ have the stereochemistry indicated in formula IV, with the definitions of the variable substituents and preferences described herein above also applying to compounds having the stereochemistry indicated in formula IV.

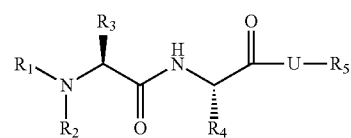

IV

Especially preferred is a compound with the stereochemistry of formula (IV) wherein $R_1$ and $R_3$ are preferably methyl or ethyl;
$R_2$ is H, methyl, ethyl, or substituted methyl especially chloromethyl, dichloromethyl and trifluoromethyl; preferably $R_2$ is H or unsubstituted methyl;
$R_4$ is $C_1$-$C_4$alkyl or $C_3$-$C_7$ cycloalkyl particularly isopropyl, t-butyl, cyclopentyl, or cyclohexyl;
$R_5$ is —$C_1$-$C_4$-alkyl-phenyl, particularly phenylmethyl, phenylethyl and phenylpropyl, indanyl, naphthyl; and
$R_6$ and $R_7$ are H or methyl.

The preferred stereochemistry for U is as shown in Figure V

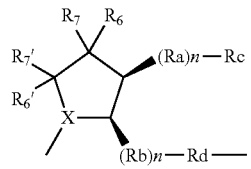

V

In a particular embodiment of the present invention, one or both of $R_6$, $R_7$, $R_{6'}$, and $R_{7'}$ is H. If one of $R_6$, $R_7$, $R_{6'}$, and $R_{7'}$ is other than H, it is especially hydroxyl or phenoxy.

Synthetic Procedure
Abbreviations:
$CH_2Cl_2$ methylene chloride
$CH_3CN$ acetonitrile
DIBAL diisobutylaluminium hydride
DIPEA diisopropylethylamine
DME ethylene glycol dimethyl ether
DMF N,N-dimethylformamide
DTBB 4,4'-di-tert-butylbiphenyl
EtOAc ethyl acetate
HBTU O-benzyltriazol-1-yl-N,N,N',N'-tetramethyluronium hexafluorophosphate
HOBt 1-hydroxybenzotriazole
HPLC high pressure liquid chromatography
KOTMS potassium trimethysilanoate.
MeOH methanol
$MgSO_4$ magnesium sulfate
$MnO_2$ manganese dioxide
$Na_2CO_3$ sodium carbonate
$NaHCO_3$ sodium bicarbonate
NaOH sodium hydroxide
Tetrakis tetrakis(triphenylphosphine)palladium(0)
TFA trifluoroacetic acid
THF tetrahydrofuran The compounds of formula (I) may be prepared as depicted below in scheme 1 (for compound #9-25, 29-31):

General synthesis scheme for compounds of formula I where W=N and X and X' are independently selected from the substituents defined above for $R_6$:
KOTMS is defined as potassium trimethysilanoate.

Scheme 1

Step A

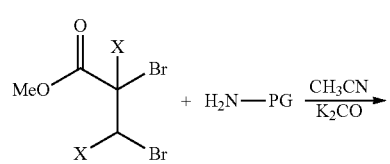

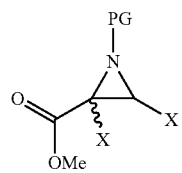

Step B

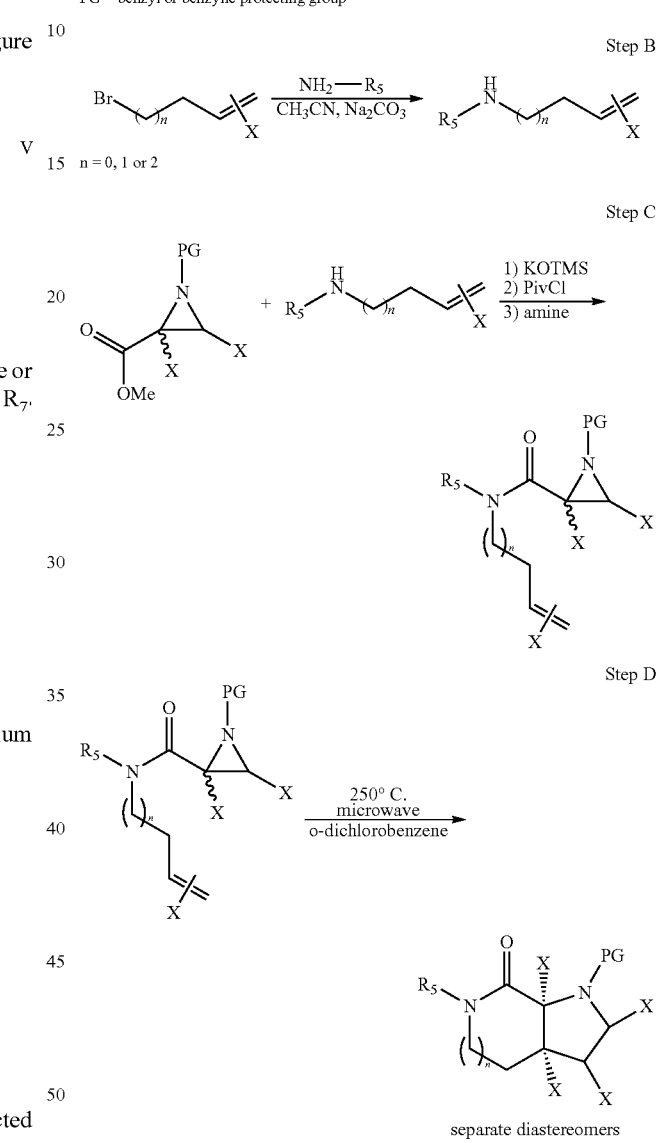

n = 0, 1 or 2

Step C

PG = benzyl or benzylic protecting group

Step D

Step E separate diastereomers

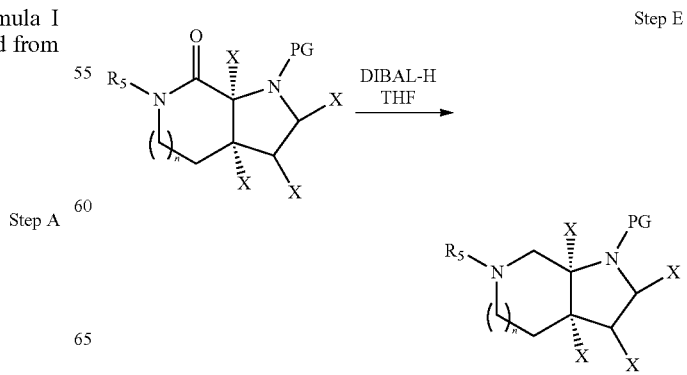

-continued

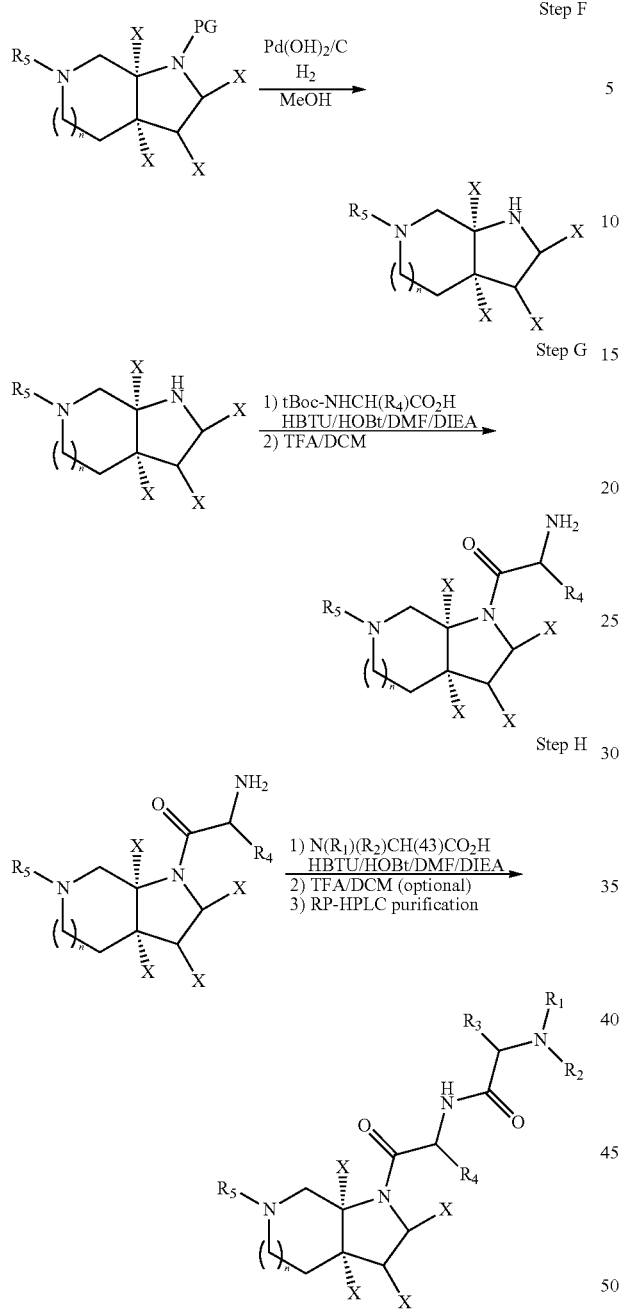

Step A: This step involves the formation of an aziridine ring via standard base mediated conditions.

Step B: This step involves the formation of a secondary amine via the reaction of an alkyl bromide with excess amine in the presence of a base.

Step C: This step involves the coupling of a secondary amine with an activated derivative of the aziridine methyl ester to form an amide substituted aziridine.

Step D: This step involves the intramolecular cycloaddition of the aziridine to the tethered alkene through a thermally accessible azomethine ylide intermediate.

Step E: This step involves the reduction of the amide to an amine via standard reduction conditions employing DIBAL-H.

Step F: This step involves the removal of the benzylic protecting group using standard palladium conditions under a hydrogen atmosphere.

Step G: This step involves coupling of the scaffold with a t-Boc protected natural or unnatural amino acid using standard peptide coupling conditions followed by the removal of the t-Boc group with TFA.

Step H: This step involves the coupling of the amine generated in the preceding step with a t-Boc protected or tertiary natural or unnatural amino acid using standard peptide coupling conditions followed by the removal of the t-Boc group with TFA if applicable. The product is then purified by high-performance liquid chromatography (HPLC).

The compounds of formula (I) may be prepared as depicted below in scheme 2 (for compound #26-28):

Scheme 2

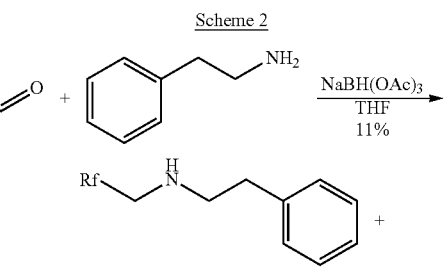

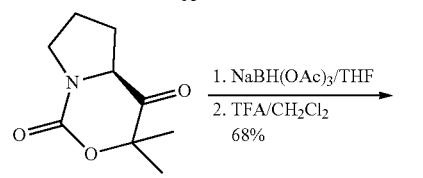

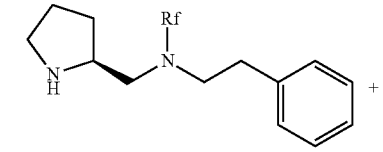

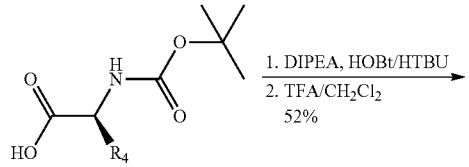

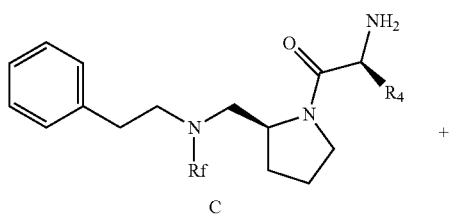

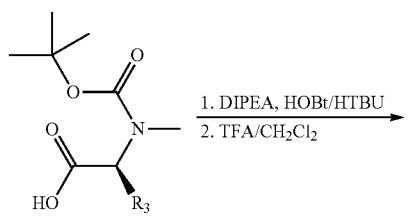

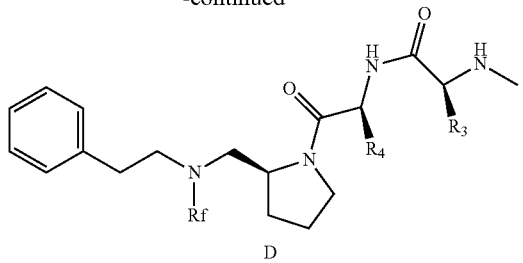
The compounds of formula (I) may be prepared as depicted below in scheme 3 (for compound #32-33):
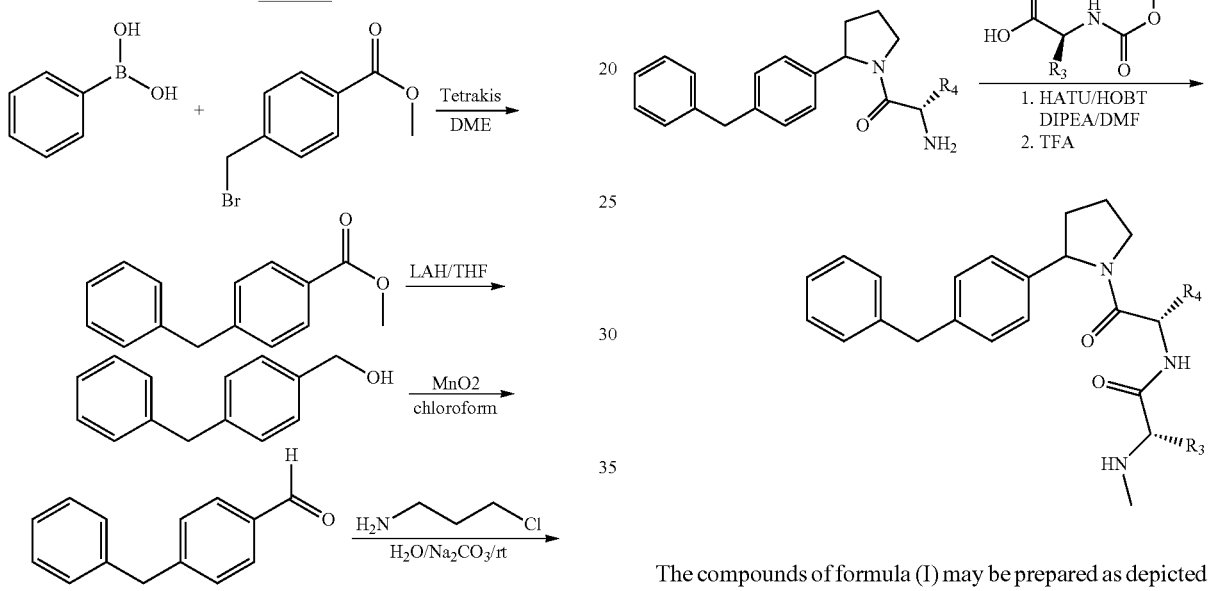
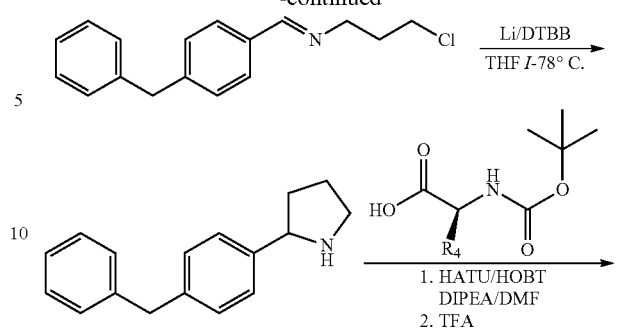
The compounds of formula (I) may be prepared as depicted below in scheme 4 (for compound #34-35):
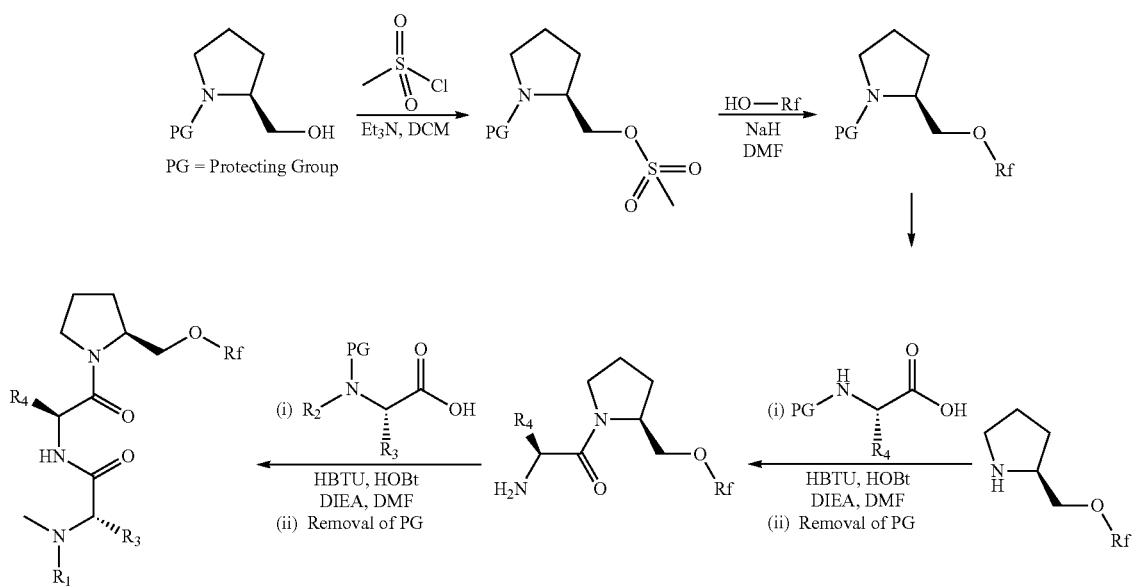

Compounds 36-38 can be prepared analogously to the preparation of compounds 34-35 according to Scheme 4.

As discussed above, the compounds of the present invention are useful for treating proliferative diseases. Thus, the present invention further relates to a method of treating a proliferative disease which comprises administering a therapeutically effective amount of a compound of the invention to a mammal, preferably a human, in need of such treatment.

A proliferative disease is mainly a tumor disease (or cancer) (and/or any metastases). The inventive compounds are particularly useful for treating a tumor which is a breast cancer, genitourinary cancer, lung cancer, gastrointestinal cancer, epidermoid cancer, melanoma, ovarian cancer, pancreas cancer, neuroblastoma, head and/or neck cancer or bladder cancer, or in a broader sense renal, brain or gastric cancer; in particular (i) a breast tumor; an epidermoid tumor, such as an epidermoid head and/or neck tumor or a mouth tumor; a lung tumor, for example a small cell or non-small cell lung tumor; a gastrointestinal tumor, for example, a colorectal tumor; or a genitourinary tumor, for example, a prostate tumor (especially a hormone-refractory prostate tumor); or (ii) a proliferative disease that is refractory to the treatment with other chemotherapeutics; or (iii) a tumor that is refractory to treatment with other chemotherapeutics due to multi-drug resistance.

In a broader sense of the invention, a proliferative disease may furthermore be a hyperproliferative condition such as leukemias, hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

Where a tumor, a tumor disease, a carcinoma or a cancer are mentioned, also metastasis in the original organ or tissue and/or in any other location are implied alternatively or in addition, whatever the location of the tumor and/or metastasis.

The inventive compound is selectively toxic or more toxic to rapidly proliferating cells than to normal cells, particularly in human cancer cells, e.g., cancerous tumors, the compound has significant antiproliferative effects and promotes differentiation, e.g., cell cycle arrest and apoptosis.

The compounds of the present invention may be administered alone or in combination with other anticancer agents, such as compounds that inhibit tumor angiogenesis, for example, the protease inhibitors, epidermal growth factor receptor kinase inhibitors, vascular endothelial growth factor receptor kinase inhibitors and the like; cytotoxic drugs, such as antimetabolites, like purine and pyrimidine analog antimetabolites; antimitotic agents like microtubule stabilizing drugs and antimitotic alkaloids; platinum coordination complexes; anti-tumor antibiotics; alkylating agents, such as nitrogen mustards and nitrosoureas; endocrine agents, such as adrenocorticosteroids, androgens, anti-androgens, estrogens, anti-estrogens, aromatase inhibitors, gonadotropin-releasing hormone agonists and somatostatin analogues and compounds that target an enzyme or receptor that is overexpressed and/or otherwise involved a specific metabolic pathway that is upregulated in the tumor cell, for example ATP and GTP phosphodiesterase inhibitors, histone deacetylase inhibitors, protein kinase inhibitors, such as serine, threonine and tyrosine kinase inhibitors, for example, Abelson protein tryosine kinase and the various growth factors, their receptors and kinase inhibitors therefore, such as, epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors and the like; methionine aminopeptidase inhibitors, proteasome inhibitors, and cyclooxygenase inhibitors, for example, cyclooxygenase-1 or -2 inhibitors.

The present invention further relates to a method of promoting apoptosis in rapidly proliferating cells, which comprises contacting the rapidly proliferating cells with an effective apoptosis promoting amount of a non-naturally-occurring compound that binds to the Smac binding site of XIAP and/or cIAP proteins. Preferably, the non-naturally-occurring compound a compound of present formula I or IV.

The present invention further relates to a method of treating or inhibiting myeloma, especially multiple myeloma. The term "myeloma" as used herein relates to a tumor composed of cells of the type normally found in the bone marrow. The term "multiple myeloma" as used herein means a disseminated malignant neoplasm of plasma cells which is characterized by multiple bone marrow tumor foci and secretion of an M component (a monoclonal immunoglobulin fragment), associated with widespread osteolytic lesions resulting in bone pain, pathologic fractures, hypercalcaemia and normochromic normocytic anaemia. Multiple myeloma is incurable by the use of conventional and high dose chemotherapies. The invention relates to a method of treating myeloma, especially myeloma which is resistant to conventional chemotherapy.

Pharmaceutical Compositions

The invention relates also to pharmaceutical compositions comprising a compound of formula I, to their use in the therapeutic (in a broader aspect of the invention also prophylactic) treatment or a method of treatment of a kinase dependent disease, especially the preferred diseases mentioned above, to the compounds for said use and to pharmaceutical preparations and their manufacture, especially for said uses.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

The pharmacologically acceptable compounds of the present invention may be present in or employed, for example, for the preparation of pharmaceutical compositions that comprise an effective amount of a compound of the formula I, or a pharmaceutically acceptable salt thereof, as active ingredient together or in admixture with one or more inorganic or organic, solid or liquid, pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g. lymphocytes), for the treatment of (this, in a broader aspect of the invention, also includes the prevention of (=prophylaxis against)) a disease that responds to inhibition of protein kinase activity, comprising an amount of a compound of formula I or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treatment for a disease that responds to inhibition of a protein kinase and/or a proliferative disease, which comprises administering a (against the mentioned diseases) prophylactically or especially therapeutically effective amount of a compound of formula I according to the invention, or a tautomer thereof or a pharmaceutically acceptable salt thereof, especially to a warm-blooded animal, for example a human, that, on account of one of the mentioned diseases, requires such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes.

Combinations

A compound of the formula I may also be used to advantage in combination with other antiproliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing agents and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating agents, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. Also included is the monoclonal antibody trastuzumab which can be administered, e.g., in the form as it is marketed, e.g. under the trademark HERCEPTIN.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity and further anti-angiogenic compounds" as used herein includes, but is not limited to: protein tyrosine kinase and/or serine and/or threonine kinase inhibitors or lipid kinase inhibitors, e.g.:
a) compounds targeting, decreasing or inhibiting the activity of the fibroblast growth factor-receptors (FGF-Rs);
b) compounds targeting, decreasing or inhibiting the activity of the insulin-like growth factor receptor I (IGF-IR), such as compounds which target, decrease or inhibit the activity of IGF-IR, especially compounds which inhibit the IGF-IR receptor, such as those compounds disclosed in WO 02/092599;
c) compounds targeting, decreasing or inhibiting the activity of the Trk receptor tyrosine kinase family;
d) compounds targeting, decreasing or inhibiting the activity of the Axl receptor tyrosine kinase family;
e) compounds targeting, decreasing or inhibiting the activity of the c-Met receptor;
f) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a PI3K inhibitor);
g) compounds targeting, decreasing or inhibiting the activity of a protein-tyrosine kinase, such as imatinib mesylate (GLIVEC/GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); and
h) compounds targeting, decreasing or inhibiting the activity of the epidermal growth factor family of receptor tyrosine kinases (EGF-R, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (HERCEPTIN), cetuximab, Iressa, Tarceva, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α-γ- or δ-tocopherol or α-γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "heparanase inhibitor" as used herein refers to compounds which target, decrease or inhibit heparin sulphate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor", e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. PS-341 and MLN 341.

The term "matrix metalloproteinase inhibitor" or ("MMP inhibitor") as used herein includes, but is not limited to collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies" as used herein includes, but is not limited to FMS-like tyrosine kinase inhibitors e.g. compounds targeting, decreasing or inhibiting the activity of Flt-3; interferon, 1-b-D-arabinofuransylcytosine (ara-c) and bisulfan; and ALK inhibitors e.g. compounds which target, decrease or inhibit anaplastic lymphoma kinase.

The term "compounds which target, decrease or inhibit the activity of Flt-3" are especially compounds, proteins or antibodies which inhibit Flt-3, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones or especially radiation.

A compound of formula I may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic, effect, or any combination thereof.

EXAMPLES

The following examples are intended to illustrate, but not further limit, the invention.

Example 1

N-[1-cyclohexyl-2-oxo-2-(6-phenethyl-octahydro-pyrrolo[2,3-c]pyridin-1-yl)-ethyl]-2-methylamino-propionamide (9)

Compound 9 according to Formula I is prepared according to the procedure set forth in Scheme 5.

Scheme 5
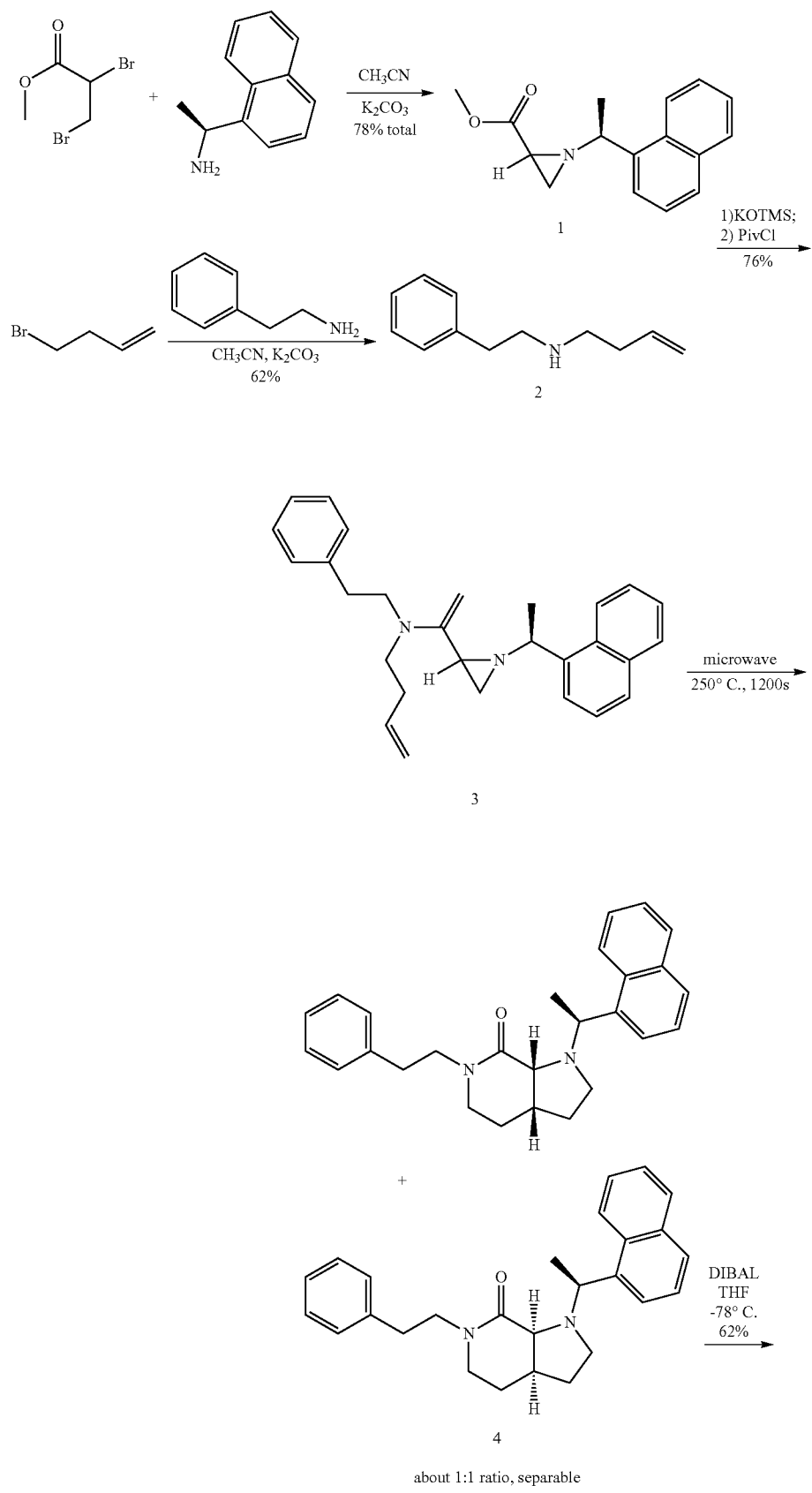

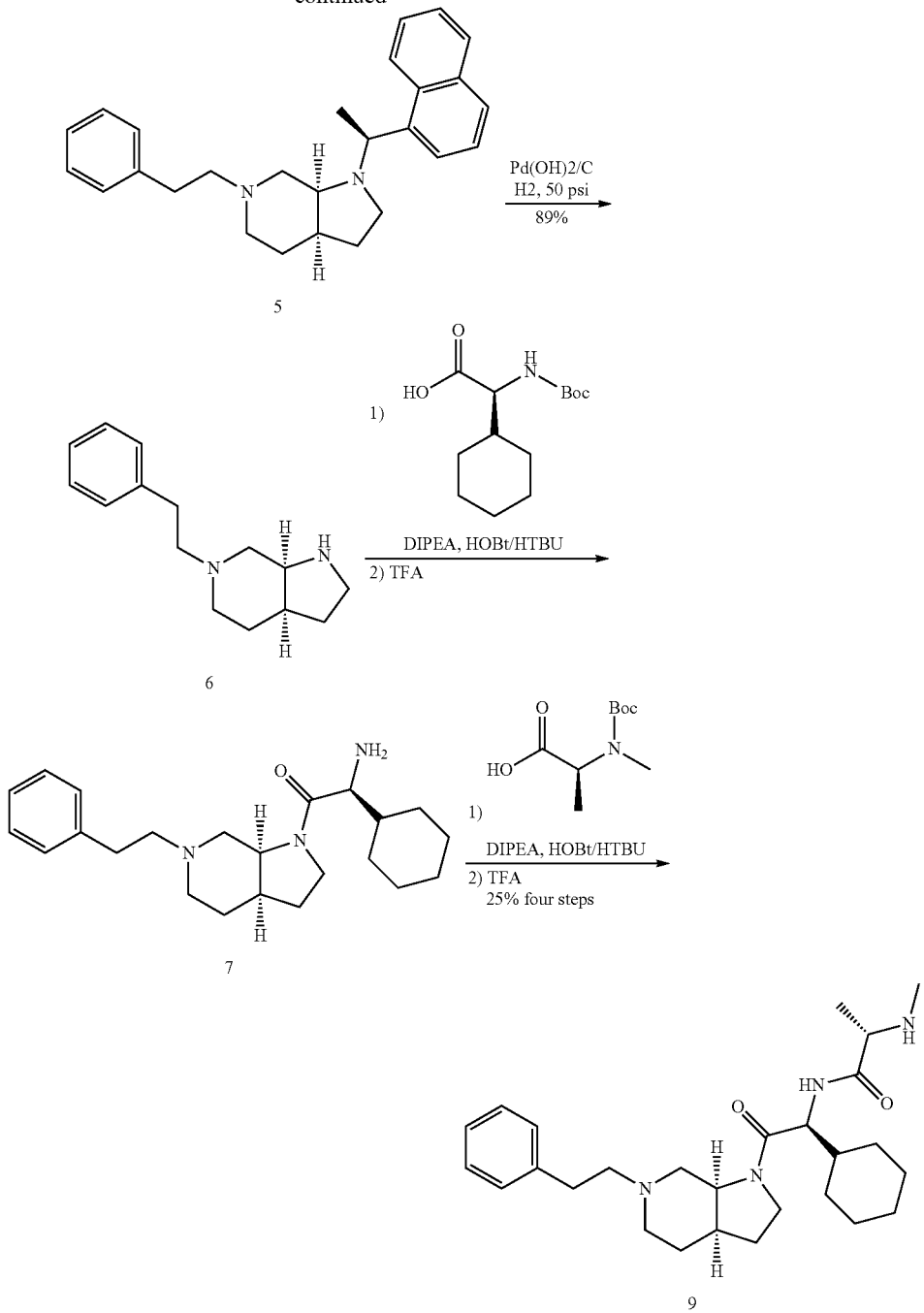

1-(1-Naphthalen-1-yl-ethyl)-aziridine-2-carboxylic acid methyl ester (1). To a solution of (S)-(−)-1-(1-naphthyl)ethylamine (20.8 g, 120 mmol) in acetonitrile (HPLC grade, 600 mL) is added K₂CO₃ (52.7 g, 360 mmol) and methyl 2,3-dibromopropionate (30 g, 120 mmol). The solution is stirred overnight at room temperature. The solution is evaporated to dryness, then H₂O/EtOAc (1:1) (600 mL) is added, and the mixture is extracted with EtOAc (4×100 mL). The organic extracts are combined, dried and concentrated under vacuum. The residue is purified by flash chromatography (silica gel; Hexane/EtOAc 1:2) to provide 24 g (78%) of the title compound as a mixture of two diastereomers in an equimolecular ratio. M+H⁺=256.10.

But-3-enyl-phenethyl-amine (2). To a solution of 2-phenylethylamine (72 mL, 570 mmol) is added K₂CO₃ (82 g, 570 mmol) and 4-bromo-1-butene (25 g, 185 mmol). The solution is stirred overnight at room temperature. The solution is evaporated to dryness and H₂O/EtOAc (1:1) (600 mL) is added. The mixture is extracted with EtOAc (4×150 mL). The organic extracts are combined, dried and concentrated under vacuum. The residue is purified by flash chromatography (silica gel; Hexane/EtOAc 1:8) to provide 20 g (62%) of the title compound. M+H⁺=176.10.

1-(1-Naphthalen-1-yl-ethyl)-aziridine-2-carboxylic acid but-3-enyl-phenethylamide (3). To a solution of 1 (12.6 g, 49.75 mmol) in THF (200 mL) is added KOTMS (6.38 g, 49.75 mmol). The mixture is stirred overnight at room temperature. The mixture is concentrated and the residue dissolved in dichloromethane (200 mL) and cooled to 0° C. Trimethylacetyl chloride (5.94 g, 49.25 mmol) is added slowly and the mixture is warmed to room temperature over 2 hours. The mixture is cooled to −78° C., 2 (8.63 g, 49.25 mmol) is added and stirring continued at −78° C. for 1.5 h. Saturated sodium bicarbonate (100 mL) is added and the mixture is allowed to warm to rt. The mixture is extracted with EtOAc (4×100 mL) and the organic extracts are combined, dried and concentrated under vacuum. The residue is purified by flash chromatography (silica gel; Hexane/EtOAc 1:8) to provide 15 g (76%) of the title compound as a mixture of two diastereomers in an equimolecular ratio. M+H$^+$=399.37.

1-(1-Naphthalen-1-yl-ethyl)-6-phenethyl-octahydro-pyrrolo[2,3-c]pyridin-7-one (4). A solution of 3 (15 g, 58.7 mmol) in o-dichlorobenzene (100 mL) is heated at 250° C. for 1200 s in a microwave reactor. The mixture is purified by flash chromatography (silica gel; Hexane/EtOAc 1:1; second spot) to provide 5 g (33%) of the title compound as an enantiomerically pure compound. M+H$^+$=399.32.

1-(1-Naphthalen-1-yl-ethyl)-6-phenethyl-octahydro-pyrrolo[2,3-c]pyridine (5). To a solution of 4 (4.8 g, 12 mmol) in THF (100 mL) is added slowly 1 M DIBAL in toluene, (50 mL, 50 mmol) at −78° C. The mixture is stirred at room temperature for 1 hour and quenched with 20 mL of water. The solvent is evaporated, the residue is diluted with 100 mL of 1:1 saturated Rochells salt/15% NaOH, and this extracted with EtOAc (4×50 mL). The organic extracts are combined, dried and concentrated under vacuum. The residue is purified by flash chromatography (silica gel; Hexane/EtOAc 1:9) to provide 2.3 g (48%) of the title compound. M+H$^+$=385.26.

6-Phenethyl-octahydro-pyrrolo[2,3-c]pyridine (6). To a solution of 5 (2.3 g, 6 mmol) in MeOH/CH$_2$Cl$_2$ (1:1; 200 mL) is added Pd(OH)$_2$ (300 mg). The mixture is agitated under 50 psi. hydrogen atmosphere for 10 h. The mixture is filtered through a celite pad, the filtrate is concentrated and the residue is used directly in the next step without further purification. M+H$^+$=231.17.

Compound (7). To a solution of 6 in dichloromethane (25 mL) is added sequentially diisopropylethylamine (4.17 mL, 24 mmol), t-Boc-L-cyclohexylglycine (1.54 g, 6 mmol), and a solution of 0.45 M HOBt/HBTU in DMF (16 mL, 7.19 mmol). The mixture is stirred overnight at room temperature, then diluted with EtOAc (200 mL) and washed sequentially with 1 M aq. citric acid (50 mL), water (50 mL), aq. Sat. NaHCO$_3$ (50 mL) and brine (2×50 mL). The organic layer is dried and concentrated under vacuum. The residue is purified by flash chromatography (silica gel; Hexane/EtOAc 1:9) to provide a yellow oil. The yellow oil is dissolved in dichloromethane (20 mL), TFA (10 mL) is added and the mixture is stirred at room temperature for 3 h. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum to provide 1.75 g (79% two steps) of the title compound which is used in next step without further purification or characterization.

Compound (9). To a solution of 7 (1.75 g, 4.74 mmol) in dichloromethane (25 mL) is added sequentially diisopropylethylamine (3.30 mL, 19 mmol), t-Boc-N-methyl-L-alanine (0.97 g, 4.74 mmol), and a solution of 0.45 M HOBt/HBTU in DMF (13 mL, 5.691 mmol). The mixture is stirred overnight at room temperature. The mixture is diluted with EtOAc (200 mL) and washed sequentially with 1 M citric acid (50 mL), water (50 mL), aq. Sat. NaHCO$_3$ (50 mL) and brine (2×50 mL). The organic layer is dried and concentrated under vacuum. The residue is dissolved in dichloromethane (20 mL), TFA (10 mL) is added and the mixture is stirred at room temperature for 3 hours. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum. The residue is purified by HPLC (C-18 silica gel, 20% CH$_3$CN/H$_2$O in 0.5% TFA) to provide 1 g (36% two steps) of the title compound as TFA salt. M+H$^+$=455.39.

Example 2

(S)—N—((S)-1-Cyclohexyl-2-{(2S,3R)-2-[(ethyl-phenethyl-amino)-methyl]-3-methyl-pyrrolidin-1-yl}-2-oxo-ethyl)-2-methylamino-propionamide (23)

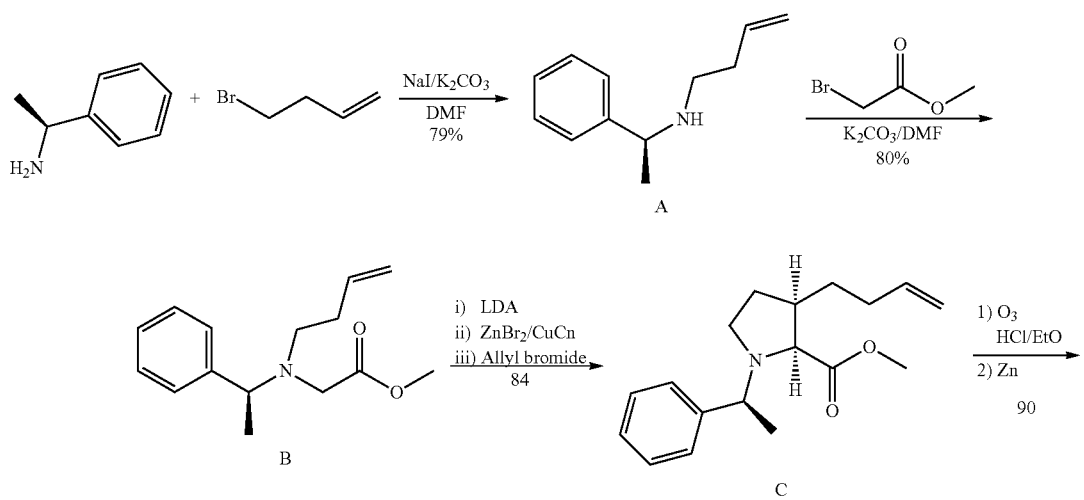

-continued
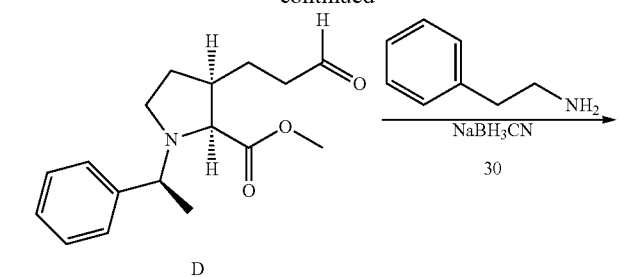
D
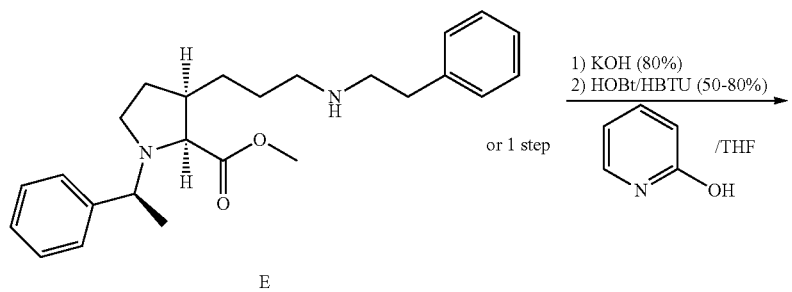
E
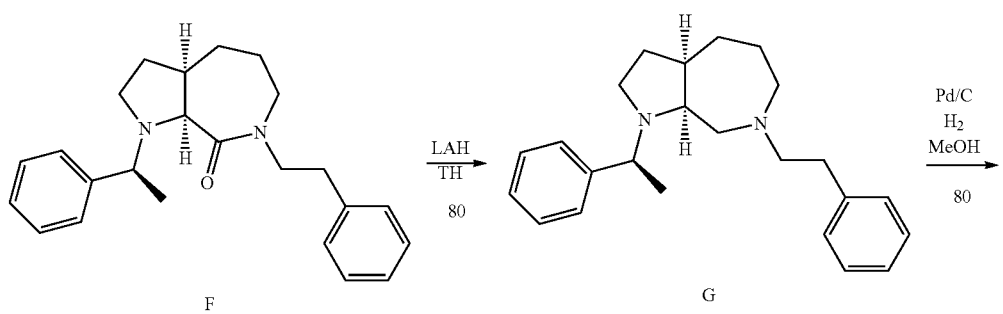
F                                    G
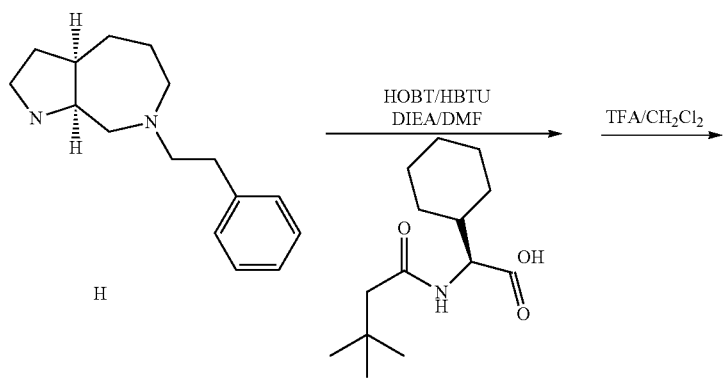
H
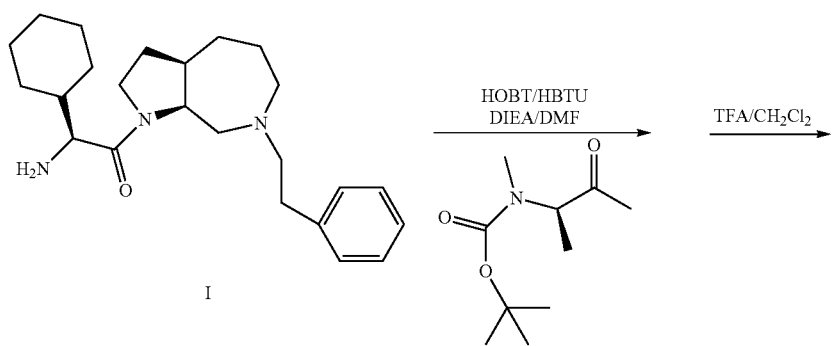
I

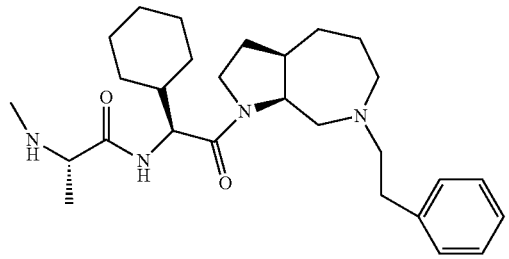

23

But-3-enyl-((S)-1-phenyl-ethyl)-amine (A): To a solution of S-(−)-1-phenyl ethylamine (15.75 g, 130 mmol) in 150 mL of DMF at 0° C. is added $K_2CO_3$ (53.9 g, 390 mmol) in small portions. After stirring at 0° C. for 10 min, 4-bromobutene (13.5 g, 100 mmol) is added dropwise and followed by NaI (58.5 g, 390 mmol) in small portions. The reaction mixture, a white suspension, is heated to 95° C. and stirred overnight/16 hrs. The solution is cooled to RT and diluted with 200 mL of ether, and washed with 3×100 ml of water. The organic layer is dried over $Na_2SO_4$ and concentrated. The crude product is purified by distillation (65-70° C. under high vacuum) to yield a colorless liquid (13.5 g, 76.7%). (NMR and MS data confirmed, U-4117-28-23).

[But-3-enyl-((S)-1-phenyl-ethyl)-amino]-acetic acid ethyl ester (B): To a solution of But-3-enyl-((S)-1-phenyl-ethyl)-amine (6.37 g, 36.4 mmol) in 150 mL of DMF at 0° C. is added $K_2CO_3$ (10.0 g, 72.8 mmol) in small portions. After stirring at 0° C. for 10 min, ethylbromoacetate (8.35 g, 54.6 mmol) is added slowly. The reaction mixture, a white suspension, is stirred at r.t. overnight/16 hrs. The solution is diluted with 200 mL of ether, and washed with 3×100 ml of water. The crude product is purified by chromatography (hexane/$CH_2Cl_2$: 50/50) to give a pale liquid (8.5 g, 94.5%). (NMR and MS data confirmed, U-4117-58).

(2S,3R)-3-But-3-enyl-1-((S)-1-phenyl-ethyl)-pyrrolidine-2-carboxylic acid ethyl ester (C): To a solution of diisopropylamine (3.6 g, 35.7 mmol) in THF (80 mL) at −40° C. is added BuLi (14.28 mL, 35.7 mmol, 2.5 M in hexane) slowly. The solution is warmed to 0° C. and stirred for 30 min to form an LDA solution. The LDA solution is cooled to −70° C. and added to a solution of [But-3-enyl-((S)-1-phenyl-ethyl)-amino]-acetic acid ethyl ester (7.8 g, 29.8 mmol) in THF (80 mL) slowly at −70° C. The light yellowish reaction solution is stirred at −20° C. for 30 min to become a deep yellow solution, and then cooled to −70° C. To the solution is added $ZnBr_2$ (16.76 g, 74.5 mmol) in ether (50 mL) dropwise at −70° C. After stirring at RT for 1.5 hrs, the reaction solution is cooled to 0° C. and added a solution of CuCN (3.47 g, 38.74 mmol) and LiCl (3.29 g, 77.48 mmol) in THF (80 mL) slowly. After stirring at 0° C. for 10 min, allyl bromide (7.26 g, 60 mmol) is added dropwise to the reaction solution, and warmed very slowly to r.t. After stirring overnight at r.t., the reaction is quenched by addition of 60 mL of saturated $NH_4Cl$ and extracted with 3×150 mL of ether. The combined organic layers is concentrated. The crude product is purified by chromatography (hexane/EtOAc: 85/15) to give a colorless liquid (7.4 g, 82.6%). (NMR and MS data confirmed, U-4117-40-19, U-4117-34-35). $ZnBr_2$ is dried at 150° C. under high vacuum for 1 hour before used**

(2S,3R)-1-((2E,4Z)—(S)-1,2-Dimethyl-hexa-2,4-dienyl)-3-(3-oxo-propyl)pyrrolidine-2-carboxylic acid ethyl ester (D): (2S,3R)-3-But-3-enyl-1-((S)-1-phenyl-ethyl)-pyrrolidine-2-carboxylic acid ethyl ester (1.0 g, 3.32 mmol) is dissolved in EtOH (10 mL) with HCl (0.5 mL, 37%), and cooled to −70° C. Ozone gas is bubbled though the solution for about 10 min or until the solution is turned very light blue color. The nitrogen gas is bubbled though the solution for 15 min to remove excess ozone in the solution. To the cool solution is added Zn dust (0.43 g, 6.6 mmol) and HCl (0.5 mL, 37%), and stirred at r.t. for 20 min. After filtration the solution is diluted with 50 mL of $CH_2Cl_2$ and washed with saturated $NaHCO_3$ (10 mL) and 2×20 ml of water. After dried and concentrated, a colorless liquid (1.0 g) is obtained without further purification for next step reaction. (NMR and MS data confirmed, U-4117-51-30).

(2S,3R)-3-(3-Phenethylamino-propyl)-1-((S)-1-phenyl-ethyl)-pyrrolidine-2-carboxylic acid ethyl ester (E): To a solution of (2S,3R)-1-((2E,4Z)—(S)-1,2-Dimethyl-hexa-2,4-dienyl)-3-(3-oxo-propyl)pyrrolidine-2-carboxylic acid ethyl ester (1.g, crude) in EtOH (10 mL) is added phenethylamine (0.44 g, 3.65 mmol) at r.t. After stirring at r.t. for 30 min, $NaBH_3CN$ (0.3 g, 4.87 mmol) is added in one portion, After stirring at r.t. for 1.5 Hrs, the reaction solution is diluted with 50 mL of ether and washed with 20 mL of brine. The ether layer is concentrated and the crude product is purified by chromatography ($CH_2Cl_2$/MeOH: 97/3) to give a pale liquid (405 mg, 30.0%). (NMR and MS data confirmed, U-4117-52-20).

(3aS,7aS)-6-Phenethyl-1-((S)-1-phenyl-ethyl)-octahydro-pyrrolo[2,3-c]pyridin-7-one (F): (2S,3R)-3-(3-Phenethylamino-propyl)-1-((S)-1-phenyl-ethyl)-pyrrolidine-2-carboxylic acid ethyl ester (340 mg, 0.83 mmol) is dissolved in 20 mL of MeOH/KOH/$H_2O$ (10 mL/5 g/5 mL). After stirring at 80° C. for 2 hrs, the solution is cooled to 0° C. and neutralized by addition of HCl (37%) to pH=5. After concentration the crude product is dissolved in 1 mL of $CH_2Cl_2$, and filtered through a short silica gel plug and eluted with $CH_2Cl_2$/MeOH (93/7) to give a pale glassy solid (250 mg, 78.9%) as the acid. (NMR and MS data confirmed, U-4117-60-22).

To a solution (0.05~0.1 M) of acid (1 equivalent) in DMF at r.t. is added diisopropylethylamine (5 equivalents). After stirring at r.t. for 20 min, a solution (0.05~0.1 M) of HOBT (1.2 equivalents) and HBTU (1.2 equivalents) in DMF is added to the reaction mixture, and continued to be stirred for 1.5 h (or monitored by TLC). The reaction solution is diluted with ether (1×5~10 times by volume of the solution), and washed with water (twice ×3 by volume of the solution). The combined organic solution is concentrated. The crude product is diluted with $CH_2Cl_2$ and dried over $Na_2SO_4$, and purified by chromatography ($CH_2Cl_2$/MeOH: 97/3) to give pure product (70~95% yield).

(NMR and MS data confirmed, U-4117-102).

Procedure for Compound F:

A solution of (2S,3R)-3-(2-Phenethylamino-ethyl)-1-((S)-1-phenyl-ethyl)-pyrrolidine-2 carboxylic acid methyl ester (400 mg, 1.05 mmol) and 2-hydroxyl pyridine (100 mg, 1.05 mmol) in THF (10 mL) is stirred at 40° C. for 24 hrs. The reaction is diluted with 50 mL of ether and washed with 2×120 mL of water. After dried and concentrated to give a pale liquid (350 mg, LC/MS shown a clean product only) without further purification for next step reaction.

(3aR,8aS)-7-Phenethyl-1-((S)-1-phenyl-ethyl)-decahydro-pyrrolo[2,3-c]azepine (G): To a solution (0.02M) of lactam (1 equivalent) in THF at −20° C. is added a solution (0.02M) of LiAlH$_4$ (2 equivalent) in THF slowly. After stirring at r.t. for 1.5 hrs, the solution is diluted with ether (1×5 times by volume of the solution) and washed with water (twice 2 times by volume of the solution), dried and concentrated. The crude product is purified by Chromatography (CH2Cl2/MeOH: 97/3) to give product (yield 70~90%).

(NMR and MS data confirmed, U-4117-104).

(3aR,8aS)-7-Phenethyl-decahydro-pyrrolo[2,3-c]azepine (H): A solution/suspension of reactant (<1 g) and Pd 10% on carbon (20% by weight) in MeOH (10 mL, with 2 drops of acetic acid) in a 1000 ml round flask is vigorously stirred at r.t. under hydrogen gas (at atmosphere pressure) from a balloon for 4-8 hrs. After degassed by house vacuum for 10 min, the reaction mixture is filtered to remove catalyst and concentrated. The crude product is diluted with CH$_2$Cl$_2$/H$_2$O (8/2, reasonable amount) and neutralized with 10% NH$_4$OH to pH=7~8. After dried and concentrated to give product (80%~quantitative yield) without purification for the next step reaction.

(NMR and MS data confirmed, U-4117-105).

(S)—N—((S)-1-Cyclohexyl-2-{(2S,3R)-2-[(ethyl-phenethyl-amino)-methyl]-3-methyl-pyrrolidin-1-yl}-2-oxo-ethyl)-2-methylamino-propionamide (compound 23): Prepared from compound H following the procedures established in Scheme 5.

Example 3

Scheme 6

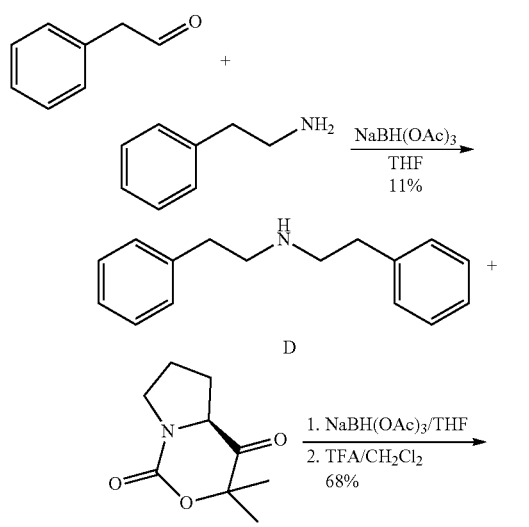

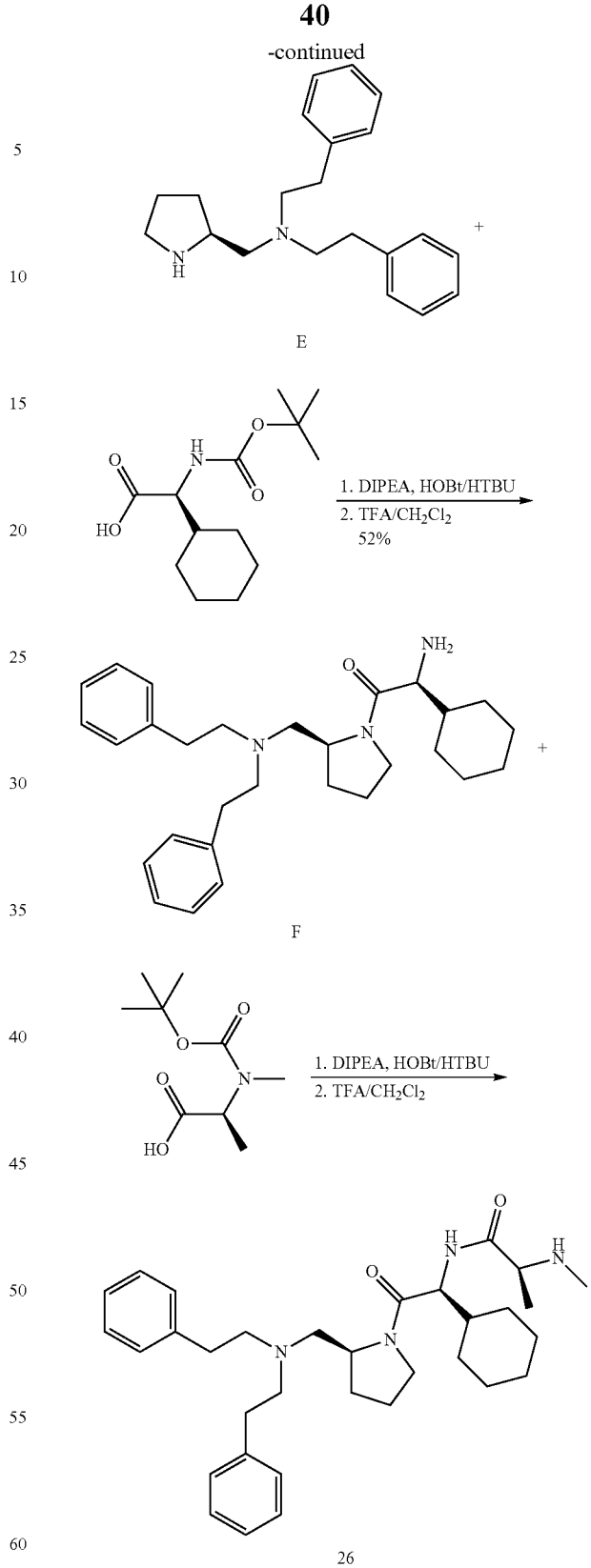

Diphenethylamine (D). To a solution of phenylacetaldehyde (6.0 g, 50 mmol) and 2-phenylethylamine in THF (200 mL) is added sodium triacetoxy-borohydride drop wise. The solution is stirred under nitrogen overnight at room temperature. The solution is quenched with aq. saturated sodium bicarbonate (200 mL), and extracted with EtOAc (4×100 mL). The organic extracts are combined, dried and concentrated under vacuum. The residue is purified by flash chromatography (silica gel; EtOAc/MeOH 9:1) to provide 1.25 g (11%) of the compound D as a clear oil. M+H$^+$=226.10.

Diphenethyl-(S)-1-pyrrolidin-2-ylmethyl-amine (E). To a solution of (S)-2-Formyl-pyrrolidine-1-carboxylic acid tert-butyl ester (1.0 g, 5.0 mmol) and D (1.125 g, 5.0 mmol) in THF (40 mL) is added sodium triacetoxyborohydride drop wise. The solution is stirred under nitrogen overnight at room temperature. The solution is quenched with aq. saturated sodium bicarbonate (40 mL). The mixture is extracted with EtOAc (4×50 mL). The organic extracts are combined, dried and concentrated under vacuum. The residue is purified by flash chromatography (silica gel; Hexane/EtOAc 4:1) to provide a yellow oil. The yellow oil is dissolved in dichloromethane (20 mL), TFA (10 mL) is added and the mixture is stirred at room temperature for 3 h. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum to provide 1.04 g (68% two steps) of the title compound E which is used in the next step without further purification or characterization.

Compound (F). To a solution of t-Boc-L-cyclohexylglycine (0.868 g, 3.38 mmol) in DMF (20 mL) is added diisopropylethylamine (1.83 mL, 16.9 mmol). The mixture is stirred for 20 minutes at room temperature. Then a solution of E, HOBt (516 mg, 3.82 mmol) and HBTU (1.448 g, 3.82 mmol) in DMF (30 mL) is added. The mixture is stirred overnight at room temperature, and then diluted by ether (200 mL) and washed sequentially with aq. 1 M citric acid (50 mL), water (50 mL), satd. aq. NaHCO$_3$ (50 mL) and brine (2×50 mL). The organic extract is dried and concentrated under vacuum. The residue is purified by flash chromatography (silica gel; Hexane/EtOAc 2:3) to provide a yellow oil. The yellow oil is dissolved in dichloromethane (20 mL), TFA (10 mL) is added and the mixture is stirred at room temperature for 3 hours. The mixture is concentrated and the residue is dissolved in dichloromethane (100 mL) and neutralized with saturated sodium bicarbonate. The solution is extracted with dichloromethane (3×50 mL). The organic extracts are combined, dried and concentrated under vacuum to provide 780 mg (52% two steps) of the title compound F which is used in the next step without further purification or characterization.

Compound 26. To a solution of t-Boc-N-methyl-L-alanine (354 mg, 1.75 mmol) in DMF (20 mL) is added diisopropylethylamine (0.938 mL, 8.75 mmol). The mixture is stirred for 20 minutes at room temperature. Then a solution of F, HOBt (267 mg, 1.98 mmol) and HBTU (751 mg, 1.98 mmol) in DMF (30 mL) is added. The mixture is stirred for 3 h at room temperature, and then diluted by ether (200 mL) and washed sequentially with 1 M citric acid (50 mL), water (50 mL), satd. aq. NaHCO$_3$ (50 mL) and brine (2×50 mL). The organic extract is dried and concentrated under vacuum. The residue is dissolved in dichloromethane (20 mL) and TFA (10 mL) is added. The mixture is stirred at room temperature for 3 h and concentrated. The resulting residue is dissolved in dichloromethane (100 mL) and neutralized with saturated sodium bicarbonate. The solution is extracted with dichloromethane (3×50 mL). The organic extracts are combined, dried and concentrated under vacuum. Portion of the residue is purified by HPLC (C-18 silica gel, 30% CH$_3$CN/H$_2$O in 0.5% TFA) to provide 120 mg of compound 26 as TFA salt. M+H$^+$=533.47.

Example 4

Compound 32 is prepared as follows:

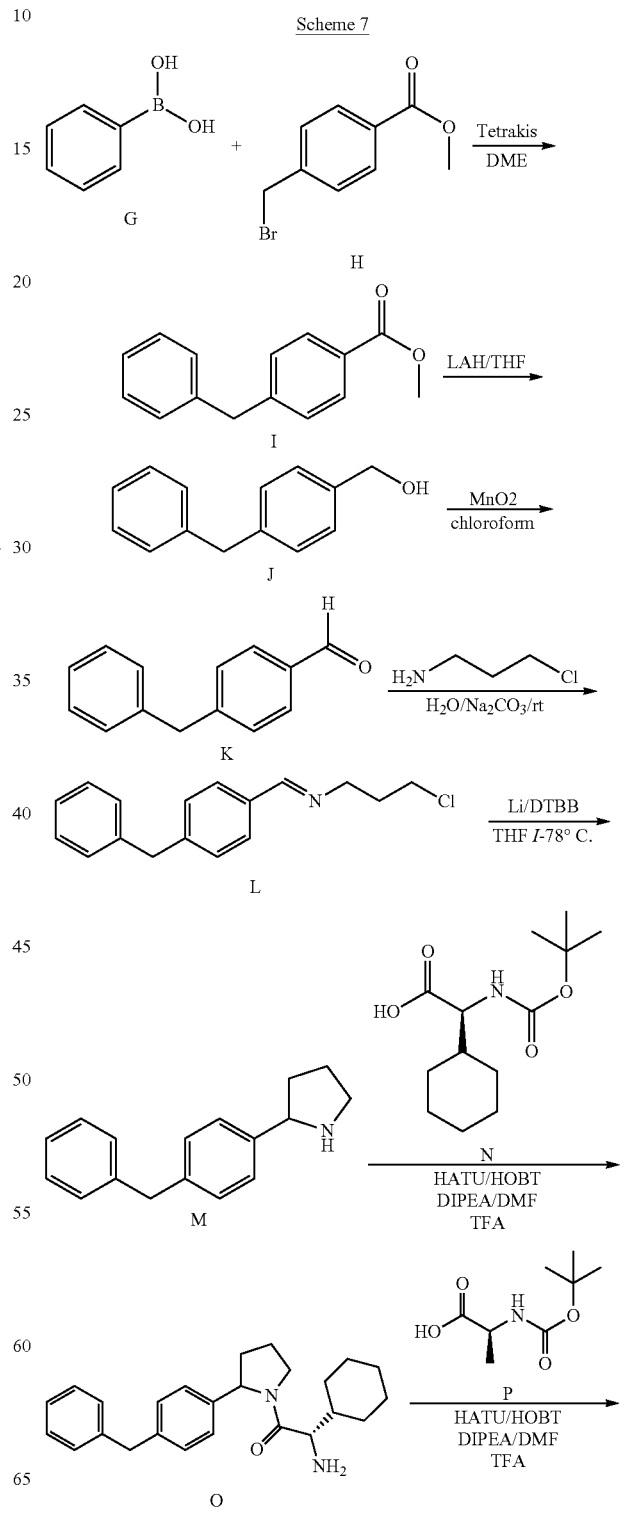

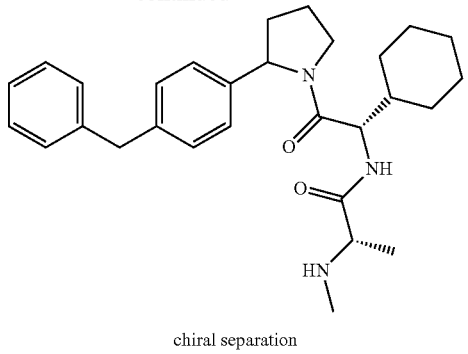

chiral separation
32

Compound I. Compounds G (122 mg, 1 mmole) and H (226 mg, 1 mmole) are dissolved in 5 mL DME. To this a mixture of 1 mL 2 N aq. Na$_2$CO$_3$ and 50 mg Tetrakis is added. The resulting mixture is degassed for 5 minutes, stirred at 90° C. for 6 h, cooled down to room temperature, and concentrated. The residue is purified by flash chromatography (ethyl acetate/hexane) to provide I as an amber oil (204 mg, 90%). The crude product is used directly in next reaction without further purification or characterization.

Compound J. LAH (38 mg) is added to a solution of I (226 mg, 1 mmole) in 5 mL THF 0° C. The temperature of the mixture is allowed to warm to room temperature and further stirred overnight. The reaction is quenched by following the Fisher method, filtered and concentrated to provide J as a colorless oil (183 mg, 92%) and is used directly in next reaction without further purification or characterization.

Compound K. The suspension of compound J (198 mg, 1 mmole) and MnO$_2$ (870 mg, 10 mmole) in 15 mL chloroform is stirred overnight. Filtering and concentration yielded product K as a colorless oil (192 mg, 98%).

$^1$H NMR (CDCl$_3$) δ 9.96 (s, 1H), 7.72 (s, 2H), 7.47 (s, 2H), 7.15-7.35 (m, 5H), 4.07 (s, 2H)

Compound L. A mixture of 3-chloropropylamine hydrochloride (140 mg, 1.1 mmole), aldehyde K (196 mg, 1.0 mmole), and sodium carbonate (212 mg, 2 mmole) in water (10 mL) is stirred overnight at room temperature. The resulting solution is extracted with ethyl acetate (3×20 mL), separated, dried over Na$_2$SO$_4$ and evaporated in vacuum (15 Torr) to give an essentially pure oily residue (270 mg) which is used for the next reaction without further purification. (M+H$^+$ 272, calc. 272)

Compound M. Imine L (271 mg, 1 mmol) is added to a blue suspension of lithium powder (75 mg, 10 mmol) and a catalytic amount of DTBB (30 mg, 0.10 mmol; 5% molar) in THF (5 mL) at −78° C. The resulting mixture is stirred for 2 h at same temperature. Reaction is quenched with water (20 mL) allowing the temperature to rise to 20° C. The resulting solution is purified by successively acid-base extraction with 2 M hydrochloric acid (3×15 mL) and 4 M sodium hydroxide (3×20 mL). The final solution is extracted with ethyl acetate (3×20 mL), separated, dried over Na$_2$SO$_4$ and evaporated to give pure compound M, (214 mg, 90%); (M+H$^+$ 238, calc. 238)

Compound O. A mixture of compound M (237 mg, 1 mmole), compound N (257 mg, 1 mmole), HBTU (460 mg, 1.2 mmole), HOBT (170 mg, 1.1 mmole), DIPEA (512 mg, 3 mmole) and 5 mL DMF is stirred overnight. The mixture is diluted with ether (25 mL), washed with water, brine, dried over MgSO$_4$, filtered, and concentrated. The resulting residue is treated with 2 mL of CH$_2$Cl$_2$/TFA (1/1), stirred for 2 h, concentrated to provided product O as a pale yellow solid (320 mg, 85%); (M+H$^+$ 377, calc. 377).

Compound 32. A mixture of compound O (376 mg, 1 mmole), t-Boc-N-methylalanine P (203 mg, 1 mmole), HBTU (460 mg, 1.2 mmole), HOBT (170 mg, 1.1 mmole), DIPEA (512 mg, 3 mmole) and 5 mL DMF is stirred overnight. The mixture is diluted with ether (25 mL), washed with water, brine, dried over MgSO$_4$, filtered, and concentrated. The resulting residue is treated with 2 mL of CH$_2$Cl$_2$/TFA (1/1), stirred for 2 h and concentrated under vacuum. Column chromatography provided compound 32 as a pale yellow solid, (397 mg, 86%). (M+H$^+$ 462, calc. 462).

Example 5

(S)—N—{(S)-1-Cyclohexyl-2-[(S)-2-(indan-2-yloxymethyl)-pyrrolidin-1-yl]-2-oxo-ethyl}-2-methylamino-propionamide (34)

(S)-2-Methanesulfonyloxymethyl-pyrrolidine-1-carboxylic acid tert-butyl ester, (P). A flame dried flask charged with (S)-2-Hydroxymethyl-pyrrolidine-1-carboxylic acid tert-butyl ester (1 g, 5 mmol), dichloromethane (DCM) (20 mL) and triethylamine (0.70 mL, 5.2 mmol) is cooled to 0° C. under N$_2$ is added a solution of methanesulfonylchloride (0.38 mL, 5 mmol) in DCM (5 mL) dropwise over 10 minutes. The reaction is stirred for 1 hour. After addition of DCM (100 mL), the reaction mixture is washed with brine, dried and concentrated in vacuo. The residue is purified by chromatography on SiO$_2$ (5% EtOAc/Hexanes) to give 1.38 g of methanesulfonate ester (P) as a clear colorless oil: LCMS (ES) 280.10 (MH$^+$).

(S)-2-(Indan-2-yloxymethyl)-pyrrolidine-1-carboxylic acid tert-butyl ester, (Q). Sodium hydride (60%) (0.6 g, 14.4 mmol) is added to a flame dried flask charged with indan-2-ol (0.965 g, 7.2 mmol) and N,N'-dimethylformamide (DMF) (20 mL), cooled to 0° C. under N$_2$ and stirred for 30 minutes. A solution of (S)-2-Methanesulfonyloxymethyl-pyrrolidine-1-carboxylic acid tert-butyl ester (P) (1 g, 3.6 mmol) in DMF (5 mL) is added dropwise to the reaction mixture in such a manner as to maintain 0° C. The reaction is stirred at 60° C. for one hour, cooled to 0° C., quenched with brine, diluted with EtOAc, washed repeatedly with brine (6×), dried and concentrated in vacuo. The residue is purified by chromatography on SiO$_2$ (5% EtOAc/Hexanes) to give 0.20 g of indanyl ether (Q) as a clear colorless oil: LCMS (ES) 340.17 (MNa+).

(S)—N—{(S)-1-Cyclohexyl-2-[(S)-2-(indan-2-yloxymethyl)-pyrrolidin-1-yl]-2-oxo-ethyl}-2-methylamino-propionamide, (34). ((S)-1-{(S)-1-Cyclohexyl-2-[(S)-2-(indan-2-yloxymethyl)-pyrrolidin-1-yl]-2-oxo-ethylcarbamoyl}-ethyl)-methyl-carbamic acid tert-butyl ester (Q) (0.54 g, 1 mmol) is dissolved in DCM (8 mL) and treated with trifluoroacetic acid (4 mL) for 45 minutes. The reaction mixture is concentrated in vacuo, purified by preparative reverse-phase hplc to give 0.096 g of the methylamine (34) as a clear gum: LCMS (ES) 442.26 (MH+).

Example 6

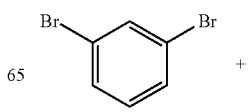

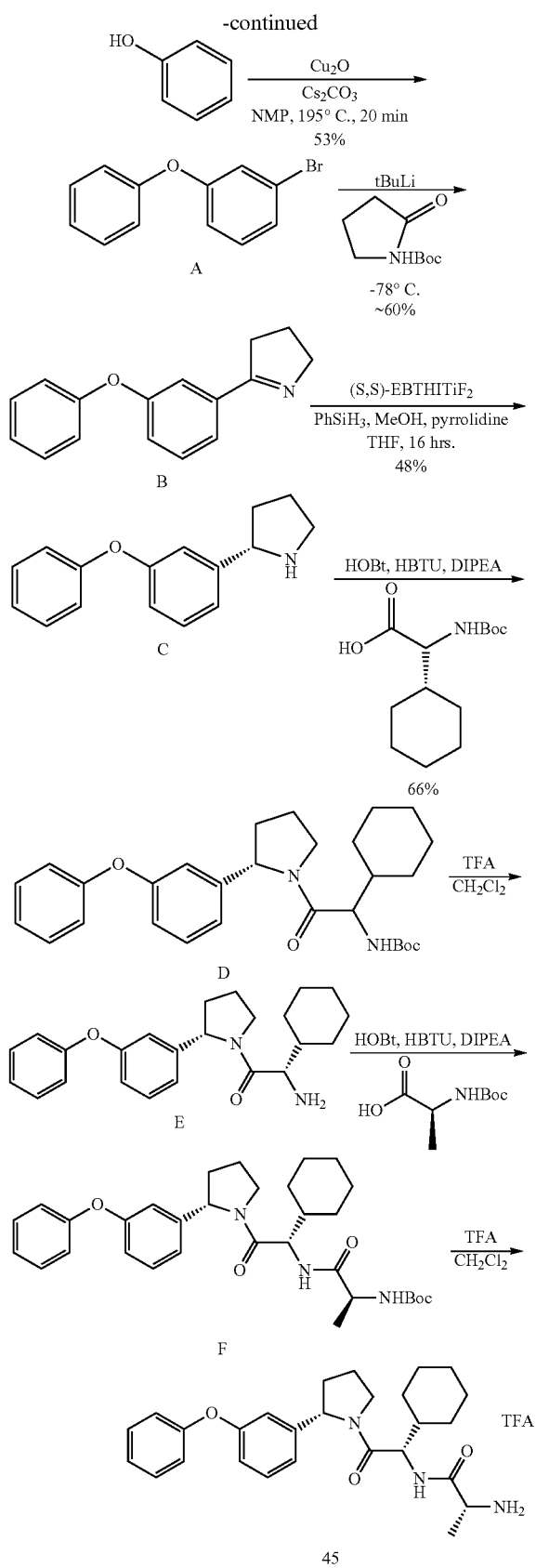

copper(I) oxide (152 mgs, 1 mmol), and cesium carbonate (3.46 g, 10.6 mmol) in 8 mL of NMP is heated at 195° C. for 20 minutes in a microwave. The heterogeneous mixture is filtered through a bed of Celite and the residue is washed with EtOAc (1×20 mL). The filtrate is diluted with 1N NaOH (200 mL) and extracted with EtOAc (3×100 mL). The organics were combined, dried over $Na_2SO_4$, filtered and concentrated under reduced pressures to give crude product as a yellow oil which is purified by column chromatography (100% hexanes) to give 1-bromo-3-phenoxy-benzene as a colorless oil (1.4 g, 53%). LCMS m/z 250 (M+1).

5-(3-Phenoxy-phenyl)-3,4-dihydro-2H-pyrrole (B): To a cold solution (−78° C.) of 1-bromo-3-phenoxy-benzene (10.13 g, 40.6 mmol) in anhydrous THF (100 mL) and under nitrogen is added n-BuLi (1.6M, 44.7 mmol, 27 mL). The mixture is allowed to stir for 30 minutes before being added to a cold solution (−78° C.) of 1-(tert-Butoxycarbonyl)-2-pyrrolidinone in anhydrous THF (50 mL) under nitrogen via cannula. The resulting mixture is allowed to warm to room temperature overnight before being quenched with water (200 mL) and extracted with EtOAc (3×100 mL). The organics were collected, dried over $Na_2SO_4$, filtered and concentrated under reduced pressures. The residue is dissolved in $CH_2Cl_2$ (20 mL) and TFA (10 mL) is added with stirring. The mixture is stirred for 30 minutes and quenched over ice cold sat. $NaHCO_3$, extracted with $CH_2Cl_2$ (3×100 mL) and the organics were combined, dried over $Na_2SO_4$, filtered and concentrated under reduced pressures. The residue is purified by silica gel column chromatography (20% EtOAc/Hexanes) to give 5-(3-phenoxy-phenyl)-3,4-dihydro-2H-pyrrole as light yellow oil (6.1 g, 63%). LCMS m/z 238 (M+1).

(S)-2-(3-Phenoxy-phenyl)-pyrrolidine (C): To oven dried round bottom flask is added S,S-EBTHITiF2 (100 mgs, 0.3 mmol) and diluted with THF (5 mL). The flask is sealed and purged with argon. To the yellow solution is added phenylsilane (4.6 mL, 37.5 mmol), pyrrolidine (100 uL, 1.1 mmol), and anhydrous methanol (100 uL, 1.1 mmol). The resulting yellow mixture is stirred for 45 minutes until green color persisted. A solution of 5-(3-phenoxy-phenyl)-3,4-dihydro-2H-pyrrole (1.2 g, 5.05 mmol) in THF (2 mL) is added to the catalyst and the mixture is stirred for 8 hrs. The reaction is carefully quenched with 10% HCl (100 mL) until gas evolution subsided and the pH~2. The mixture is diluted with EtOAc (100 mL) and the aqueous layer is removed, neutralized with 3M NaOH (50 mL) until basic and extracted with EtOAc (3×100 mL). The organics were combined, dried over $Na_2SO_4$, filtered and concentrated under reduced pressures. The solid residue is purified by silica gel column chromatography (100% EtOAc) to give (S)-2-(3-phenoxy-phenyl)-pyrrolidine as a yellow solid (580 mgs, 48%). LCMS m/z 240.1 (M+1).

{(S)-1-Cyclohexyl-2-oxo-2-[(S)-2-(3-phenoxy-phenyl)-pyrrolidin-1-yl]-ethyl}-carbamic acid tert-butyl ester (D): (S)-2-(3-phenoxy-phenyl)-pyrrolidine (1.2 g, 5.02 mmol) is added to a solution of Boc-L-α-cyclohexylglycine (1.42 g, 5.2 mmol), HOBt (1.0 g, 7.53 mmol) and HBTU (2.86 g, 7.53 mmol) in 10 mL of DMF. Hunig's base (3.6 Ml, 20 mmol) is added and the mixture is stirred for 30 minutes. The mixture is diluted with brine (20 mL) and extracted with EtOAc (3×10 mL). The organics were combined, dried over $Na_2SO_4$, filtered, concentrated under reduced pressures and purified by silica gel column chromatography (20% EtOAc/Hexanes) to give {(S)-1-cyclohexyl-2-oxo-2-[(S)-2-(3-phenoxy-phenyl)-pyrrolidine-1-yl]-ethyl}-carbamic acid tert-butyl ester as a white powder (1.65 g, 66%). LCMS m/z 479.2 (M+1).

1-Bromo-3-phenoxy-benzene (A) A mixture of dibromobenzene (3 g, 12.75 mmol), phenol (1 g, 10.6 mmol), (S)-2-Amino-2-cyclohexyl-1-[(S)-2-(3-phen oxy-phenyl)-pyrrolidin-1-yl]-ethanone (E): To a solution of {(S)-1-cyclohexyl-2-oxo-2-[(S)-2-(3-phenoxy-phenyl)-pyrrolidine-1-yl]-ethyl}-carbamic acid tert-butyl ester in CH$_2$Cl$_2$ (20 mL) is added TFA (10 mL) and the mixture is stirred for 30 minutes. The mixture is concentrated under reduced pressures to give (S)-2-amino-2-cyclohexyl-1-[(S)-2-(3-phenoxy-phenyl)-pyrrolidin-1-yl]-ethanone as a TFA salt quantitatively (1.65 g). LCMS m/z 379 (M+1).

((S)-1-{(S)-1-Cyclohexyl-2-oxo-2-[(S)-2-(3-phenoxy-phenyl)-pyrrolidin-1-yl]-ethylcarbamoyl}-ethyl)-methyl-carbamic acid tert-butyl ester (F): To a solution of Boc-N-methyl-L-alanine (771 mgs, 3.79 mmol), HOBt (700 mgs, 5.17 mmol), and HBTU (2.0 g, 5.17 mmol) in DMF (10 mL) is added (S)-2-amino-2-cyclohexyl-1-[(S)-2-(3-phenoxy-phenyl)-pyrrolidin-1-yl]-ethanone and DIPEA (3 mL, 17.25 mmol). The mixture is stirred for 30 minutes and diluted with brine (20 mL) and extracted with EtOAc (3×10 mL). The organics were combined, dried over Na$_2$SO$_4$, filtered, concentrated under reduced pressures and purified by silica gel column chromatography (50% EtOAc/Hexanes) to give the product ((S) 1-{(S)-1-cyclohexyl-2-oxo-2-[(S)-2-(3-phenoxy-phenyl)-pyrrolodin-1-yl]-ethylcarbamoyl}-ethyl)-methyl-carbamic acid tert-butyl ester as a white powder (1.3 g, 84%). LCMS m/z 564 (M+1).

(S)—N—{(S)-1-Cyclohexyl-2-oxo-2-[(S)-2-(3-phenoxy-phenyl)-pyrrolidin-1-yl]-ethyl}-2-methylamino-propionamide (45): To a solution of ((S) 1-{(S)-1-cyclohexyl-2-oxo-2-[(S)-2-(3-phenoxy-phenyl)-pyrrolodin-1-yl]-ethylcarbamoyl}-ethyl)-methyl-carbamic acid tert-butyl ester (450 mgs, 0.79 mmol) in CH$_2$Cl$_2$ (20 mL) is added TFA (10 mL) and stirred for 30 minutes. The mixture is concentrated under reduced pressures and purified by reverse phase column chromatography to give the product as a TFA salt (370 mgs, 82%). LCMS m/z 464.1 (M+1).

Example 7

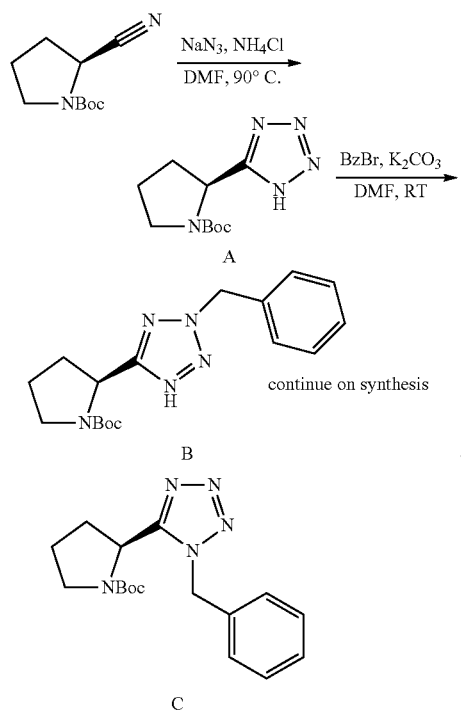

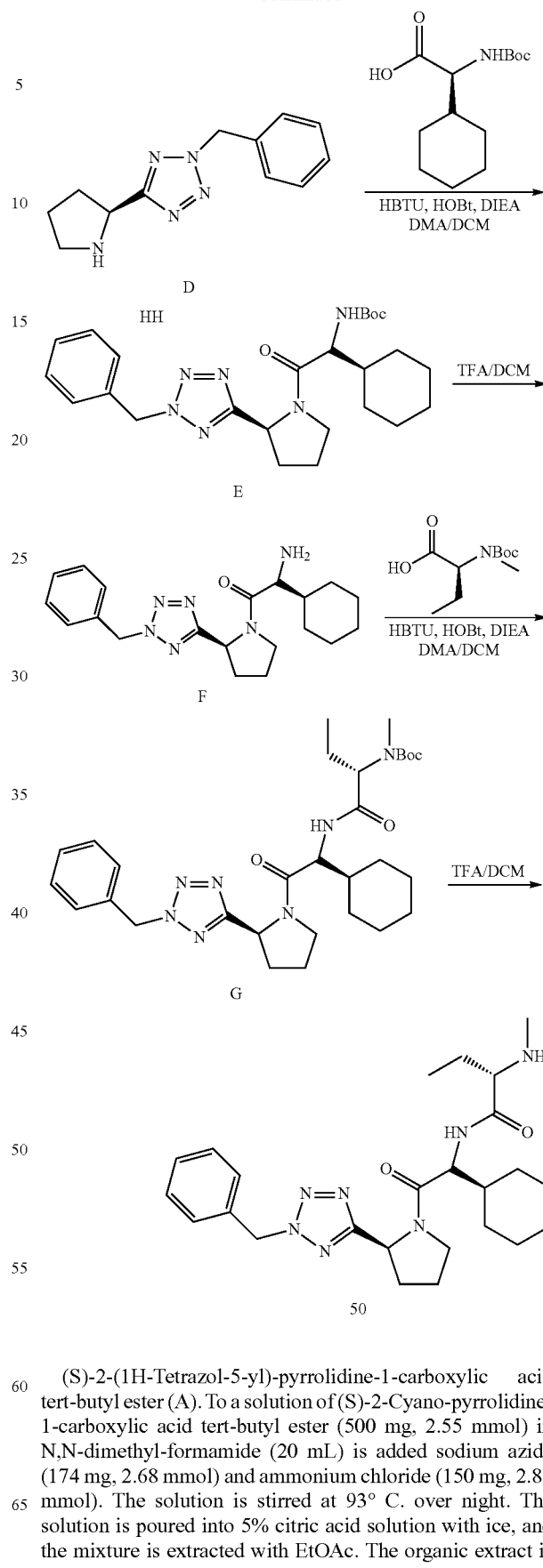

(S)-2-(1H-Tetrazol-5-yl)-pyrrolidine-1-carboxylic acid tert-butyl ester (A). To a solution of (S)-2-Cyano-pyrrolidine-1-carboxylic acid tert-butyl ester (500 mg, 2.55 mmol) in N,N-dimethyl-formamide (20 mL) is added sodium azide (174 mg, 2.68 mmol) and ammonium chloride (150 mg, 2.81 mmol). The solution is stirred at 93° C. over night. The solution is poured into 5% citric acid solution with ice, and the mixture is extracted with EtOAc. The organic extract is washed with brine, dried and concentrated under vacuum. The crude oil is used directly in the next step without further purification. M+H⁺=240.

(S)-2-(2-Benzyl-2H-tetrazol-5-yl)-pyrrolidine-1-carboxylic acid tert-butyl ester (B). To a solution of crude compound A in N,N-dimethyl-formamide (5 mL) is added K₂CO₃ (1.16 g, 8.4 mmol) and benzyl bromide (665 uL, 5.6 mmol). The solution is stirred at room temperature for 1 hr. The mixture is diluted with EtOAc and washed with brine. The organic layer is dried and concentrated under vacuum. The residue is purified by flash column chromatography (Hexanes/EtOAc) to provide 404 mg of the title compound M+H⁺=330, and 401 mg of the other region isomer (S)-2-(1-Benzyl-1H-tetrazol-5-yl)-pyrrolidine-1-carboxylic acid tert-butyl ester (C). M+H⁺=330. Combined yield is 87% for 2 steps.

2-Benzyl-5-(S)-pyrrolidine-2-yl-2H-tetrazole (D). To a solution of compound B in DCM (5 mL) is added triethylsilane (479 uL, 3.0 mmol) and then TFA (5 mL). The solution is stirred at room temperature for 1 hr and dried under vacuum. The crude oil is used directly in the next step without further purification. M+H⁺=230.

{2-[(S)-2-(2-Benzyl-2H-tetrazol-5-yl)-pyrrolidin-1-yl]-1-cyclohexyl-2-oxo-ethyl}-carbamic acid tert-butyl ester (E). To a solution of (S)-tert-butoxycarbonylamino-cyclohexyl-acetic acid (123.8 mg, 0.48 mmol) in DMA (5 mL) is added HBTU (248.8 mg, 0.656 mmol), HOBt (88.6 mg, 0.656 mmol) and diisopropylethylamine (305 uL, 1.75 mmol). The mixture is stirred at room temperature for 5 minutes. A solution of compound D in DCM (5 mL) is added to the above mixture at 0° C. The reaction mixture is stirred at room temperature for 1 hour and concentrated under vacuum. The residue is diluted with EtOAc. The organic is washed with brine, citric acid (5%), brine, NaHCO₃ (Sat.) and brine. The organic layer is then dried and concentrated under vacuum. The residue is purified by flash column chromatography (Hexanes/EtOAc) to provide the title compound 190 mg (92%). M+H⁺=369.

2-Amino-1-[(S)-2-(2-Benzyl-2H-tetrazol-5-yl)-pyrrolidin-1-yl]-2-cyclohexyl-ethanone; compound with trifluoro-acetic acid (F). To a solution of compound E in DCM (4 mL) is added TFA (4 mL) at 0° C. The solution is stirred at room temperature for 1 hr and dried under vacuum. The crude oil is used directly in the next step without further purification. M+H⁺=369.

((S)-1-{2-[(S)-2-(2-Benzyl-2H-tetrazol-5-yl)-pyrrolidin-1-yl]-1-cyclohexyl-2-oxo-ethylcarbamoyl}-propyl)-methyl-carbamic acid tert-butyl ester (G). To a solution of (S)-2-(tert-butoxycarbonyl-methyl-amino)-butyric acid (53.0 mg, 0.24 mmol) in DMA (2 mL) is added HBTU (125.0 mg, 0.33 mmol), HOBt (44.6 mg, 0.33 mmol) and diisopropylethylamine (192 uL, 1.1 mmol). The mixture is stirred at room temperature for 5 minutes. A solution of compound F in DCM (2 mL) is added to the above mixture at 0° C. The reaction mixture is stirred at room temperature for 1 hour and concentrated under vacuum. The residue is diluted with EtOAc. The organic is washed with brine, citric acid (5%), brine, NaHCO₃ (Sat.) and brine. The organic layer is then dried and concentrated under vacuum. The crude oil is used directly in the next step without further purification. M+H⁺=554.

(S)—N-{2-[(S)-2-(2-Benzyl-2H-tetrazol-5-yl)-pyrrolidin-1-yl]-1-cyclohexyl-2-oxo-ethyl}-2-methylamino-butyramide; compound with trifluoro-acetic acid (50). To a solution of compound G in DCM (2 mL) is added TFA (2 mL) at 0° C. The solution is stirred at room temperature for 1 hr and dried under vacuum. The crude oil is purified by HPLC to provide the title compound. M+H⁺=467.

Example 8

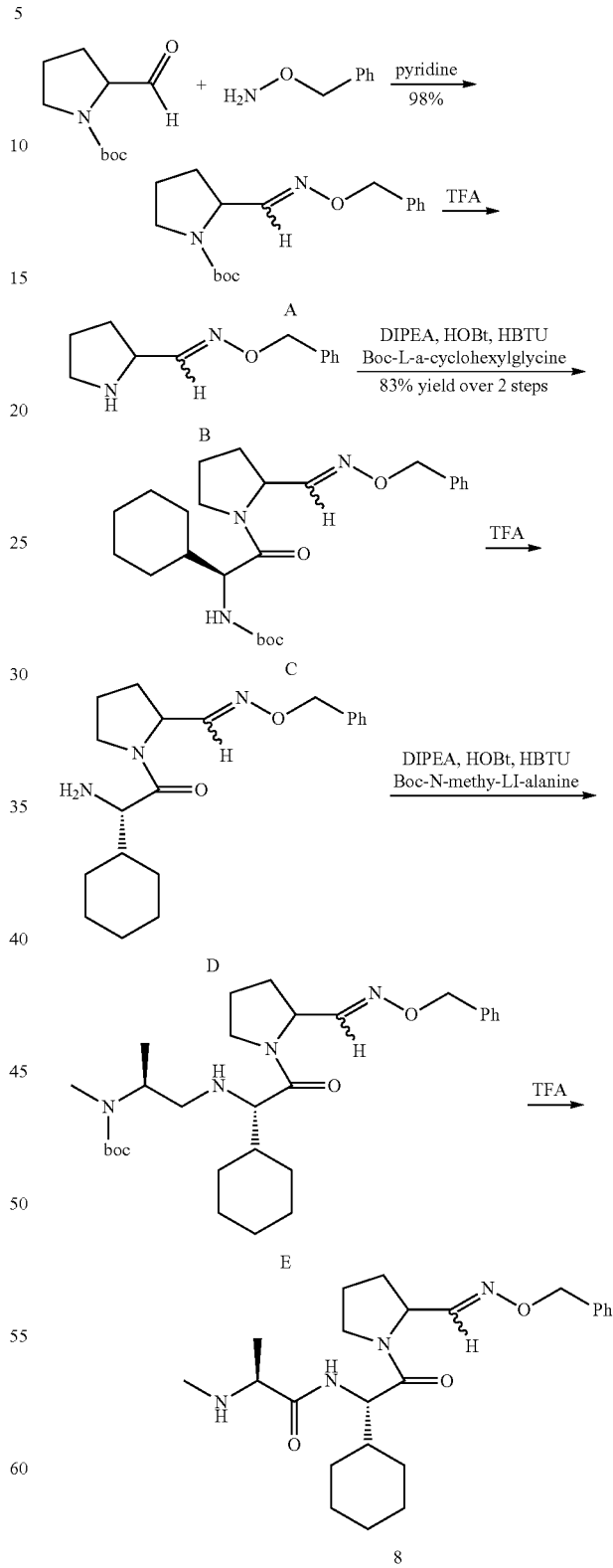

2-(Benzyloxyimino-methyl)-pyrrolidine-1-carboxylic acid tert-butyl ester (A). To a solution of benzylhydroxylamine (2.64 g, 16.56 mmole) in dry pyridine (20 ml) is added 2-formyl-pyrrolidine-1-carboxylic acid tert-butyl ester (3.30 g, 16.56 mmole). The solution is stirred for three hours at room temperature. The reaction solution is quenched with water and extracted with dichloromethane. The organic layer is combined, dried, and concentrated under vacuum. The residue is purified by flash chromatography (silica gel; from 50% to 50% of ethyl acetate in hexane) to provide 4.9 g (98%) of the title compound. M+H$^+$–Boc=205.1.

Pyrrolidine-2-carbaldehyde-O-benzyl-oxime (B). The solution of 2-(benzyloxyimino-methyl)-pyrrolidine-1-carboxylic acid tert-butyl ester (1.50 g, 4.92 mmole) and TFA (10 ml) in dichloromethane (10 ml) is stirred for 2 hours at room temperature. Solvent is removed. The crude product is carried to next step without further purification. M+H$^+$=205.1

{(S)-2-[Benzyloxyimino-methyl-pyrrolidine-1-yl]-1-cyclohexyl-2-oxo-ethyl}-carbamic acid tert-butyl ester (C). The solution of boc-L-α-cyclohexylglycine (1.27 g, 4.92 mmole), 1-hydroxybenzotriazole (0.99 g, 7.38 mmole), diisopropylethylamine (2.54 g, 19.68 mmole), and O-benzotriazole-N,N,N,N-tetramethyl-urounium hexafluorophosphate (2.80 g, 7.38 mmole) in dichloromethane (30 ml) is stirred for 15 minutes at room temperature. A solution of pyrrolidine-2-carbaldehyde-O-benzyl-oxime (~1.00 g, 0.49 mmole) in dichloromethane is added. The reaction solution is stirred for three hours at room temperature and then quenched with saturated NaHCO$_3$ aqueous., extracted with dichloromethane. The organic layer is combined, dried, and concentrated under vacuum. The residue is purified by flash chromatography (silica gel; from 20% to 70% of ethyl acetate in hexane) to provide 1.81 g (83% over 2 steps) of the title compound. M+H$^+$=444.2

1-((S)-2-Amino-2-cyclohexyl-acetyl)-pyrrolidine-2-Carbaldehyde-O-benzyl-oxime (D). The solution of {(S)-2-[benzyloxyimino-methyl-pyrrolidine-1-yl]-1-cyclohexyl-2-oxo-ethyl}-carbamic acid tert-butyl ester (1.76 g, 3.97 mmole) and TFA (10 ml) in dichloromethane (20 ml) is stirred for a hour. Solvent is removed under vacuum. The residue is carried to next step without further purification. M+H$^+$=344.2

((S)-1-{(S)-2-[2-(Benzyloxyimino-methyl)-pyrrolidine-1-yl]-1-cyclohexyl-2-oxo-ethylcarbamoyl}-ethyl)-methyl-carbamic acid tert-butyl ester (E). The solution of Boc-L-α-cyclohexylglycine (0.81 g, 3.87 mmole), 1-hydroxybenzotriazole (0.81 g, 5.95 mmole), diisopropylethylamine (2.05 g, 15.88 mmole), and O-benzotriazole-N,N,N,N-tetramethyl-urounium hexafluorophosphate (2.35 g, 5.95 mmole) in dichloromethane is stirred for 15 minutes at room temperature. A solution of 1-((S)-2-amino-2-cyclohexyl-acetyl)-pyrrolidine-2-carbaldehyde-O-benzyl-oxime (~1.40 g, 3.97 mmole) in dichloromethane is added. The reaction solution is stirred for three hours at room temperature and then quenched with saturated NaHCO$_3$ aqueous and extracted with dichloromethane. The organic layer is combined, dried, and concentrated under vacuum. The residue is carried to next step without further purification. M+H$^+$=529.4.

(S)—N-{2-[2-(Benzyloxyimino-methyl-pyrrolidine-1-yl]-1-cyclohexyl-2-oxo-ethyl}-2-methylamino-propionamide (8). The solution of ((S)-1-{(S)-2-[2-(benzyloxyimino-methyl)-pyrrolidine-1-yl]-1-cyclohexyl-2-oxo-ethylcarbamoyl}-ethyl)-methyl-carbamic acid tert-butyl ester (~2.10 g, 3.97 mmole) and TFA (20 ml) in dichloromethane (40 ml) is stirred for a hour. Solvent is removed under vacuum. 1.36 g of crude product is obtained. The crude product (0.66 g) is purified by HPLC (C18 silica gel, from 10% to 70% of CH$_3$CN/H$_2$O in 0.1% TFA) to provide 0.058 g of the title compound as TFA salt of isomeric mixtures. M+H$^+$=429.4.

Examples 9-78

The following compounds are prepared by methods analogous to those described herein utilizing analogous starting materials:

TABLE 1

| Compound Structure | Example Number |
| --- | --- |
| 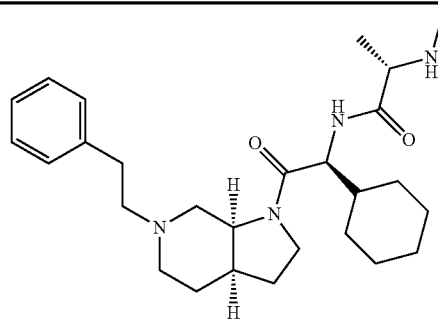 | Example 9<br>MS ESI 455.34 (M + H)$^+$ |
| 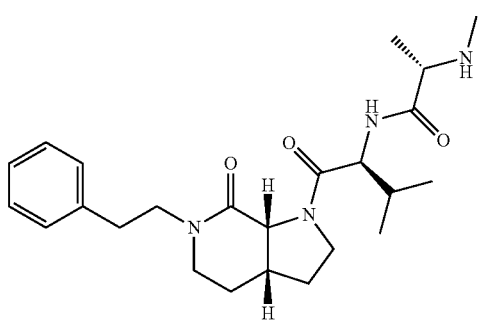 | Example 10<br>MS ESI 429.46 (M + H)$^+$ |

TABLE 1-continued
| Compound Structure | Example Number |
| --- | --- |
| 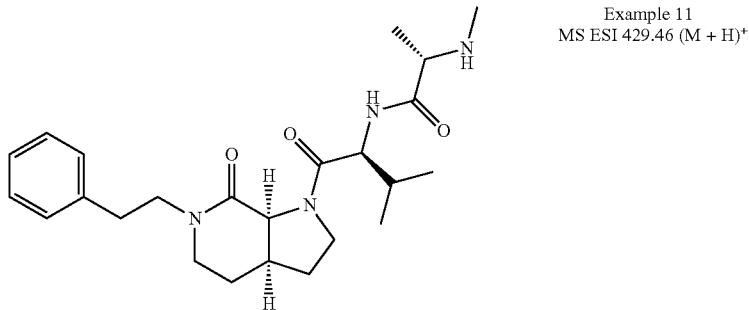 | Example 11<br>MS ESI 429.46 (M + H)+ |
| 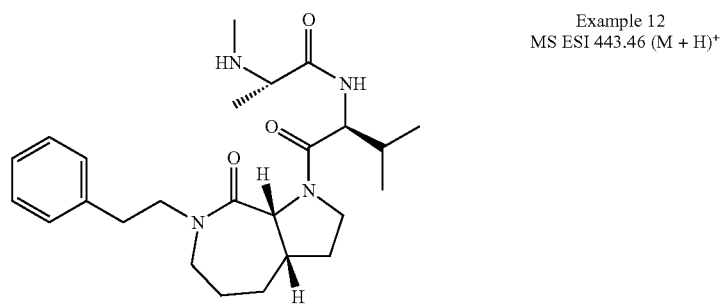 | Example 12<br>MS ESI 443.46 (M + H)+ |
| 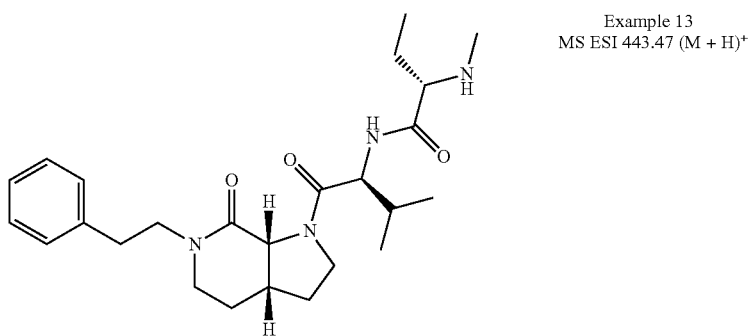 | Example 13<br>MS ESI 443.47 (M + H)+ |
| 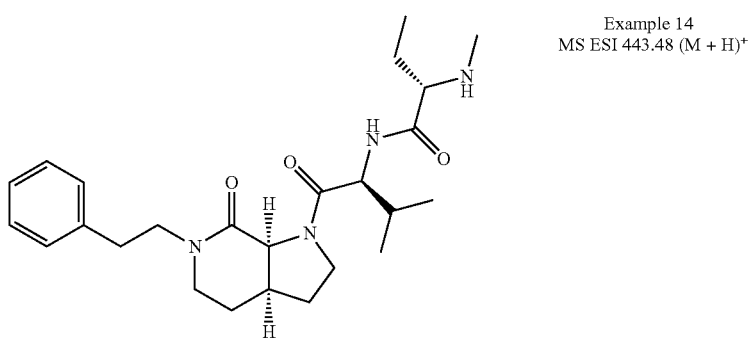 | Example 14<br>MS ESI 443.48 (M + H)+ |

TABLE 1-continued
| Compound Structure | Example Number |
|---|---|
| 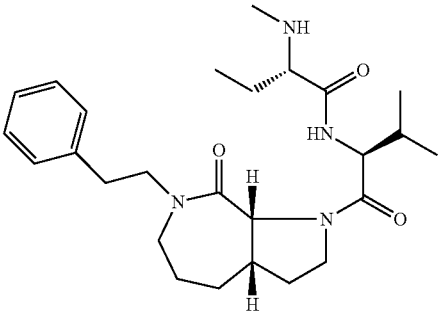 | Example 15<br>MS ESI 457.27 (M + H)⁺ |
| 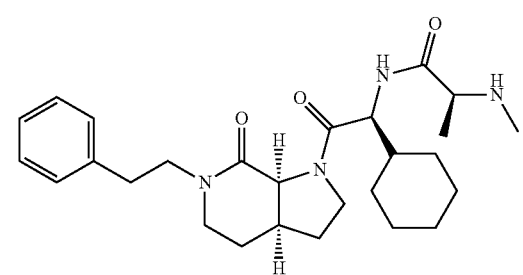 | Example 16<br>MS ESI 469.23 (M + H)⁺ |
| 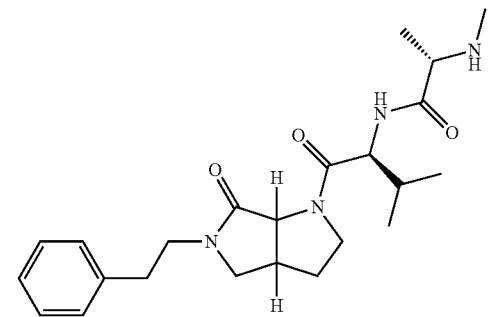 | Example 17<br>MS ESI 415.26 (M + H)⁺ |
| 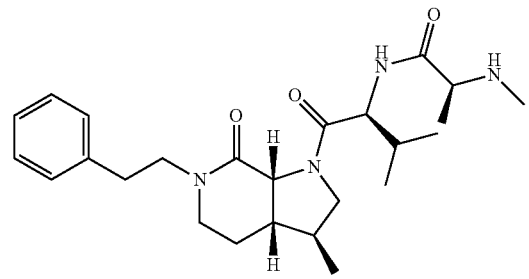 | Example 18<br>MS ESI 443.19 (M + H)⁺ |
| 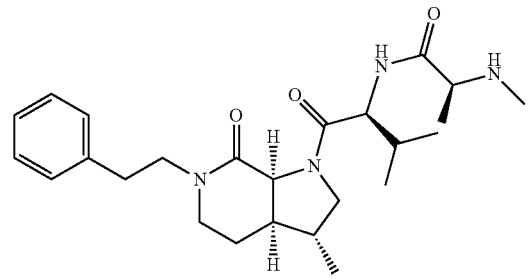 | Example 19<br>MS ESI 443.19 (M + H)⁺ |

TABLE 1-continued
| Compound Structure | Example Number |
|---|---|
| 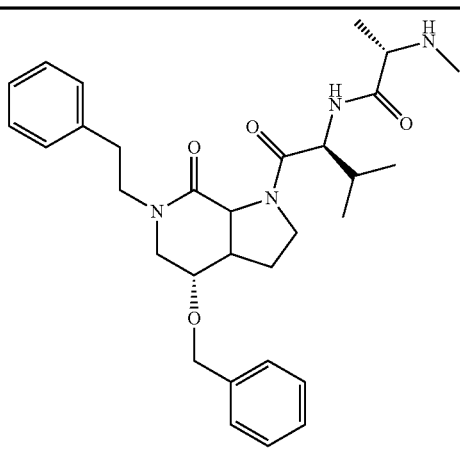 | Example 20<br>MS ESI 535.33 (M + H)+ |
| 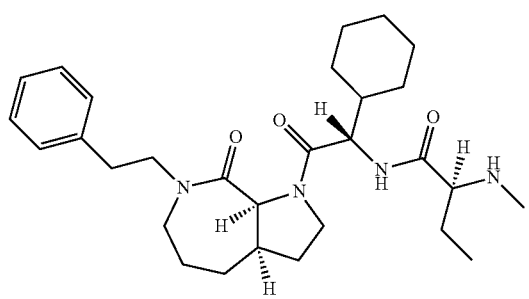 | Example 21<br>MS ESI 497.33 (M + H)+ |
| 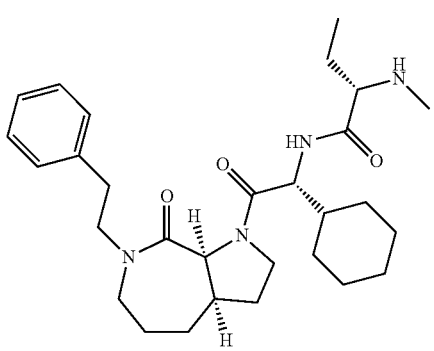 | Example 22<br>MS ESI 497.35 (M + H)+ |
| 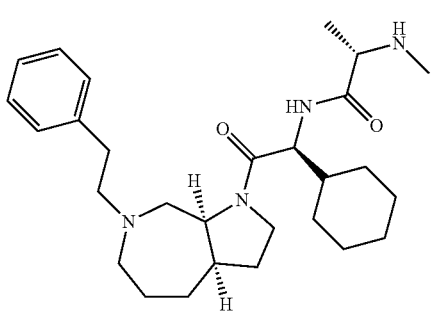 | Example 23<br>MS ESI 469.36 (M + H)+ |

TABLE 1-continued

| Compound Structure | Example Number |
|---|---|
| 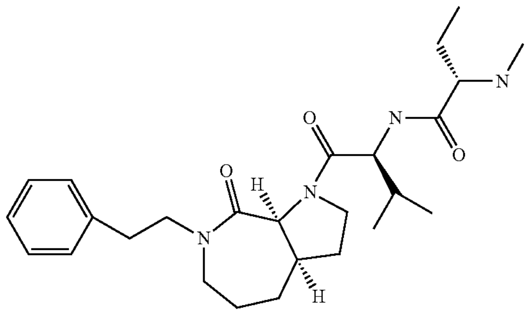 | Example 24<br>MS ESI 457.6 (M + H)+ |
| 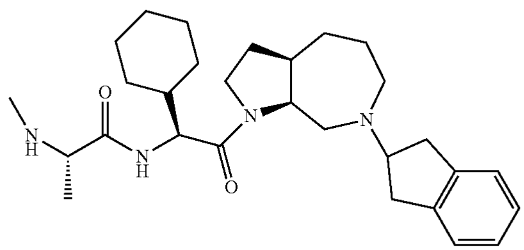 | Example 25<br>MS ESI 481.7 (M + H)+ |
| 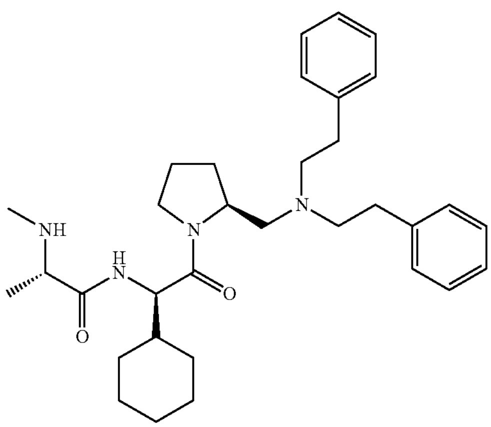 | Example 26<br>MS ESI 533.5 (M + H)+ |
| 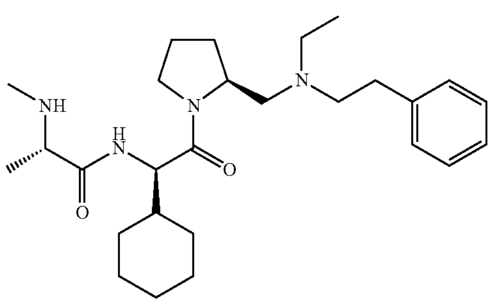 | Example 27<br>MS ESI 457.43 (M + H)+ |
| 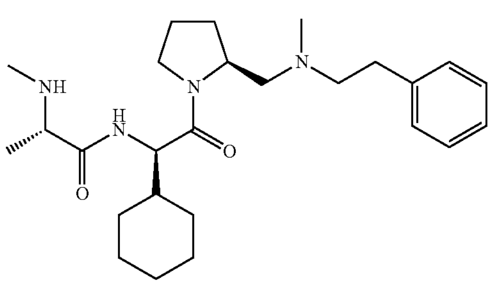 | Example 28<br>MS ESI 443.23 (M + H)+ |

TABLE 1-continued

| Compound Structure | Example Number |
|---|---|
| | Example 29<br>MS ESI 442.65 (M + H)⁺ |
| | Example 30<br>MS ESI 428.62 (M + H)⁺ |
| | Example 31<br>MS ESI 414.30 (M + H)⁺ |
| | Example 32<br>MS ESI 462.0 (M + H)⁺ |
| | Example 33<br>MS ESI 422.1 (M + H)⁺ |
| | Example 34<br>MS ESI 442.26 (M + H)⁺ |

TABLE 1-continued
| Compound Structure | Example Number |
|---|---|
| 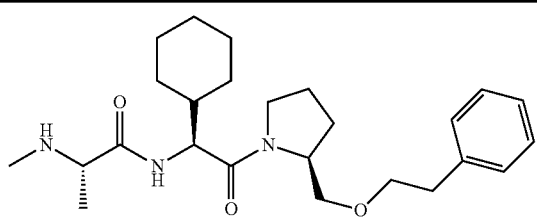 | Example 35<br>MS ESI 430.28 (M + H)+ |
| 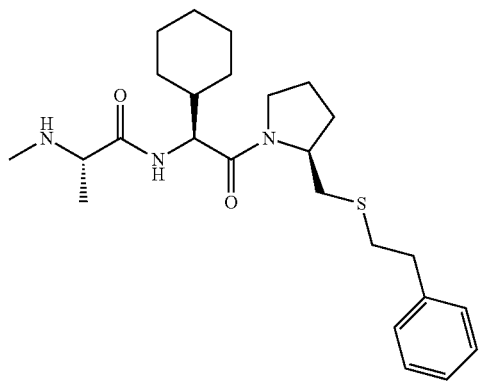 | Example 36<br>MS ESI 446.6 (M + H)+ |
| 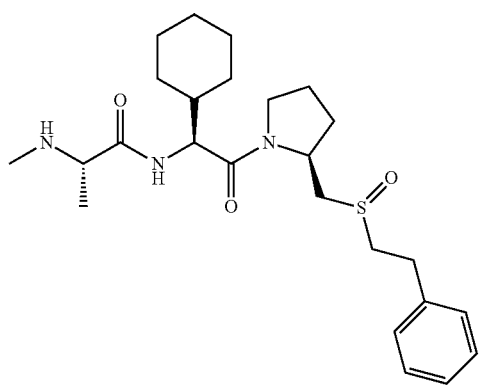 | Example 37<br>MS ESI 462.6 (M + H)+ |
| 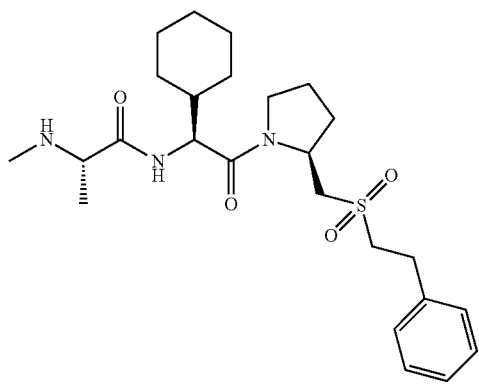 | Example 38<br>MS ESI 478.7 (M + H)+ |

TABLE 1-continued

| Compound Structure | Example Number |
| --- | --- |
| 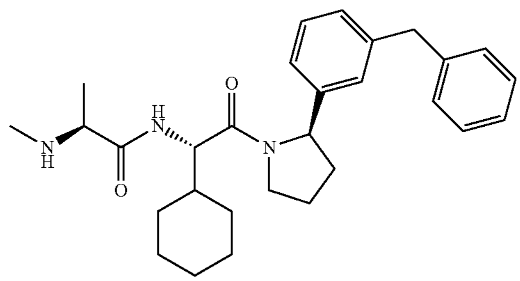 | Example 39<br>MS ESI 462.3 (M + H)+ |
| 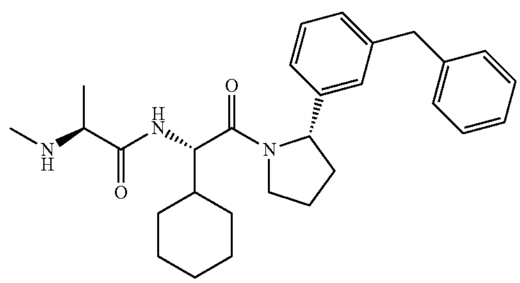 | Example 40<br>MS ESI 462.3 (M + H) |
| 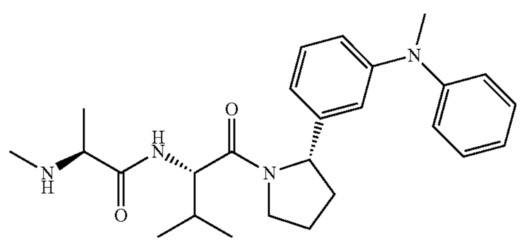 | Example 41<br>MS ESI 437.3 (M + H)+ |
| 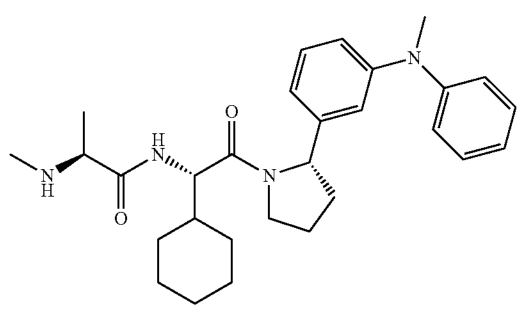 | Example 42<br>MS ESI 477.3 (M + H)+ |
| 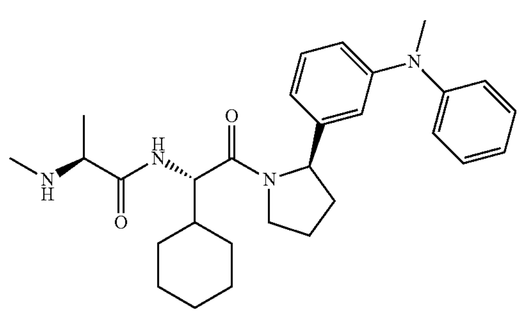 | Example 43<br>MS ESI 477.3 (M + H)+ |

TABLE 1-continued

| Compound Structure | Example Number |
|---|---|
| 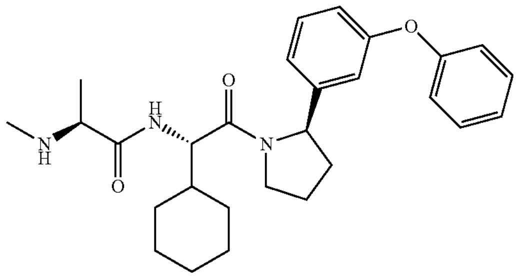 | Example 44<br>MS ESI 464.3 (M + H)+ |
| 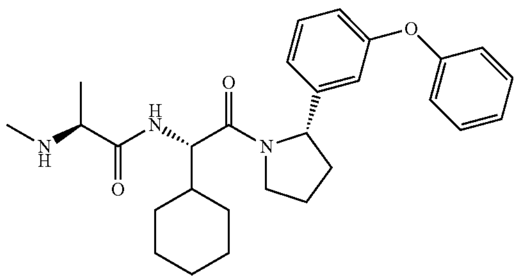 | Example 45<br>MS ESI 464.3 (M + H)+ |
| 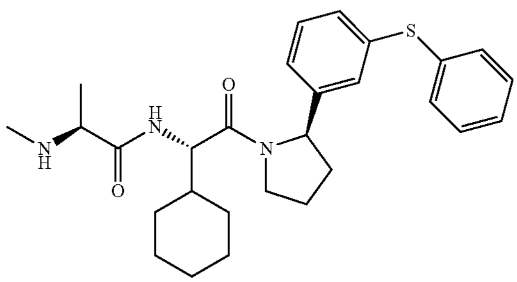 | Example 46<br>MS ESI 480.3 (M + H)+ |
| 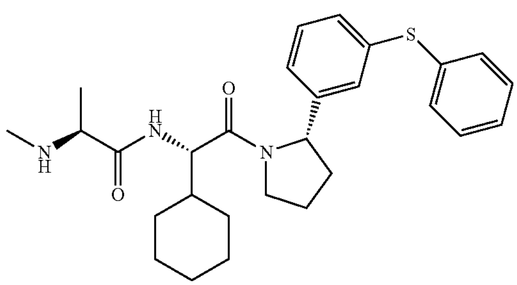 | Example 47<br>MS ESI 480.3 (M + H)+ |
| 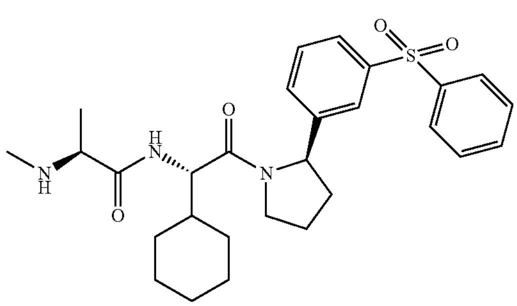 | Example 48<br>MS ESI 512.0 (M + H)+ |

TABLE 1-continued
| Compound Structure | Example Number |
|---|---|
| 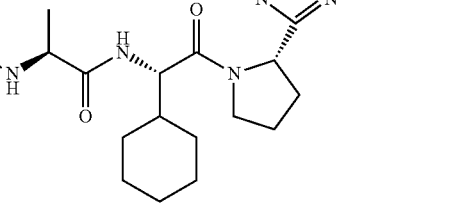 | Example 49<br>MS ESI 454.3 (M + H)+ |
| 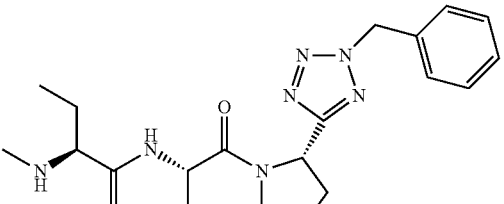 | Example 50<br>MS ESI 468.3 (M + H)+ |
| 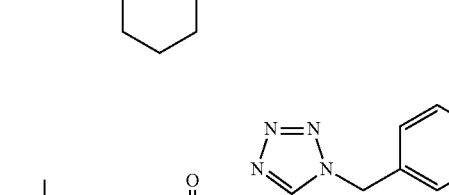 | Example 51<br>MS ESI 454.3 (M + H)+ |
| 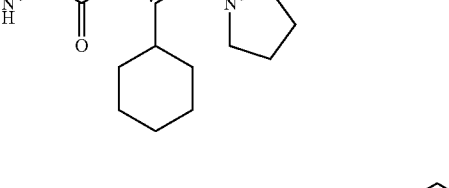 | Example 52<br>MS ESI 468.3 (M + H)+ |
| 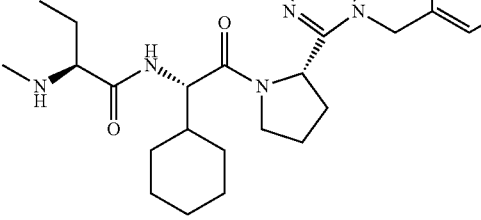 | Example 53<br>MS ESI 439 (M + H)+ |

TABLE 1-continued

| Compound Structure | Example Number |
|---|---|
| 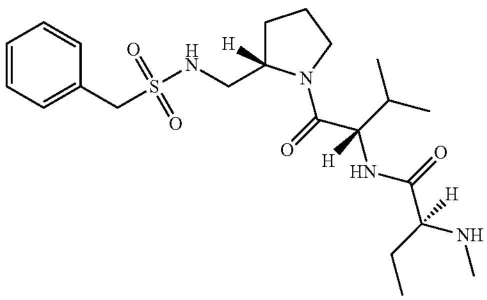 | Example 54<br>MS ESI 453 (M + H)$^+$ |
| 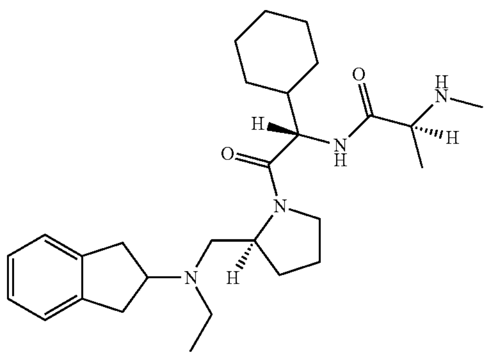 | Example 55<br>MS ESI 469.3 (M + H)$^+$ |
| 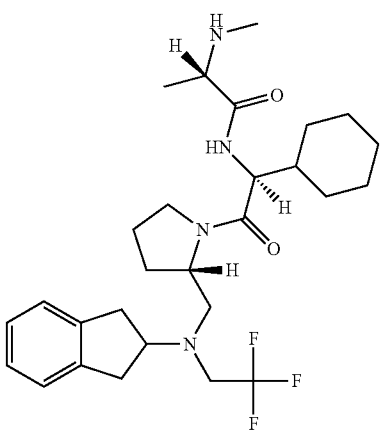 | Example 56<br>MS ESI 523.2 (M + H)$^+$ |
| 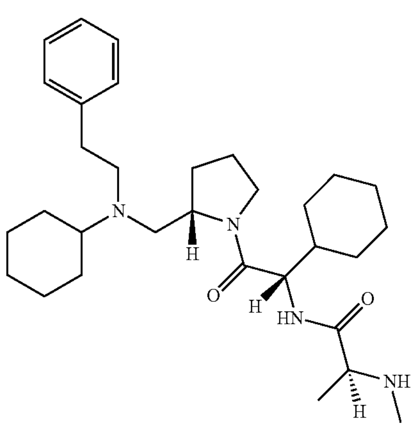 | Example 57<br>MS ESI 511 (M + H)$^+$ |

TABLE 1-continued

| Compound Structure | Example Number |
|---|---|
| 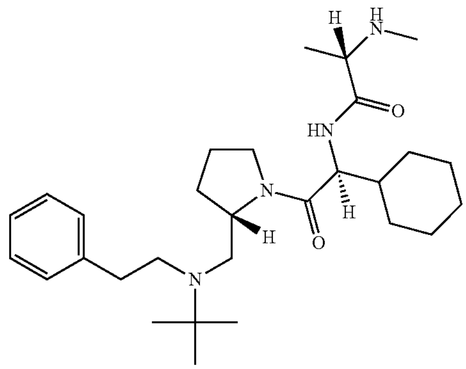 | Example 58<br>MS ESI 485 (M + H)+ |
| 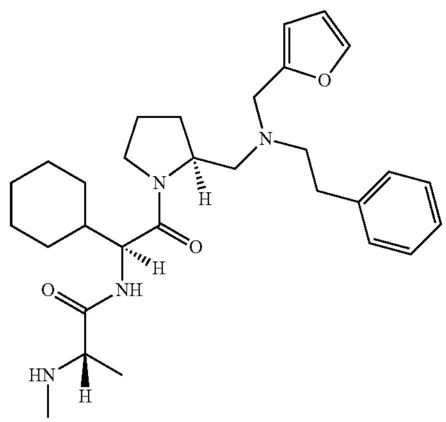 | Example 59<br>MS ESI 509 (M + H)+ |
| 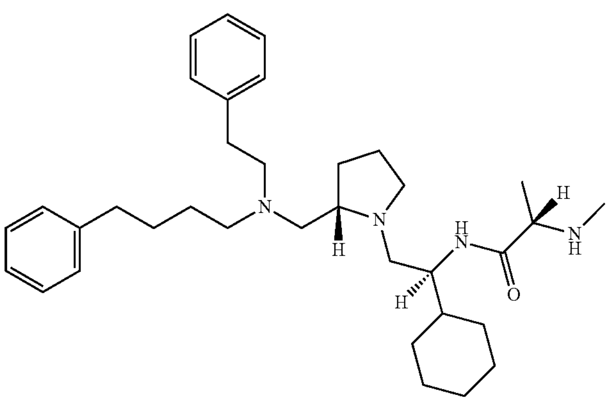 | Example 60<br>MS ESI 826 (M + H)+ |
| 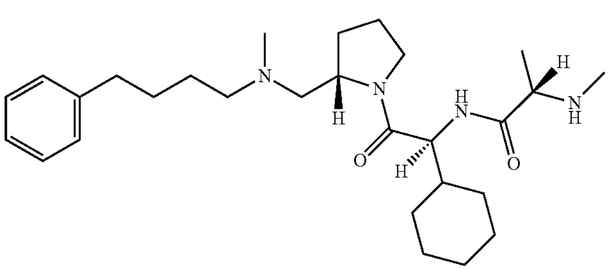 | Example 61<br>MS ESI 471.3 (M + H)+ |

| Compound Structure | Example Number |
|---|---|
| 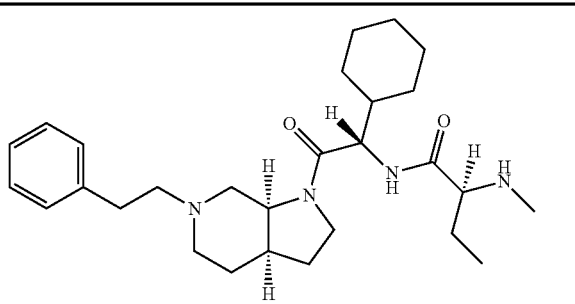 | Example 62<br>MS ESI 469.4 (M + H)+ |
| 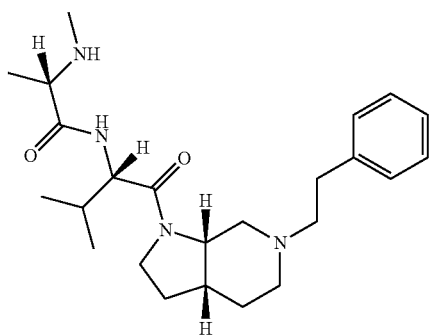 | Example 63<br>MS ESI 415.3 (M + H)+ |
| 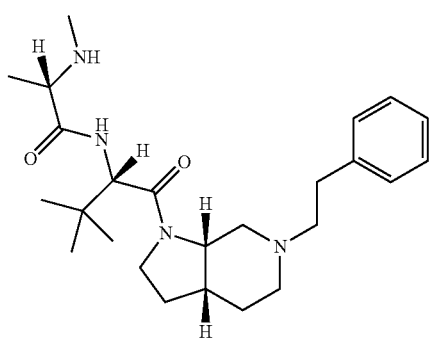 | Example 64<br>MS ESI 443.4 (M + H)+ |
| 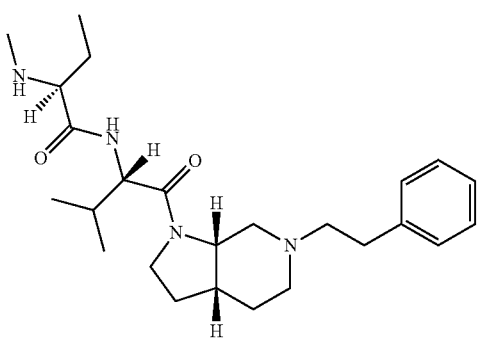 | Example 65<br>MS ESI 429.4 (M + H)+ |

TABLE 1-continued
| Compound Structure | Example Number |
|---|---|
| 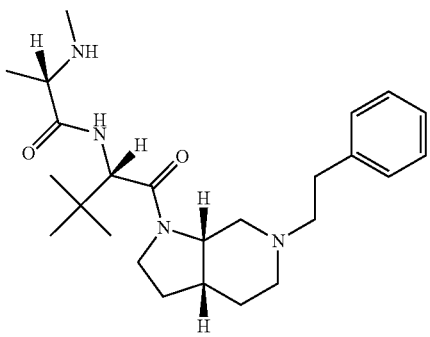 | Example 66<br>MS ESI 429.4 (M + H)+ |
| 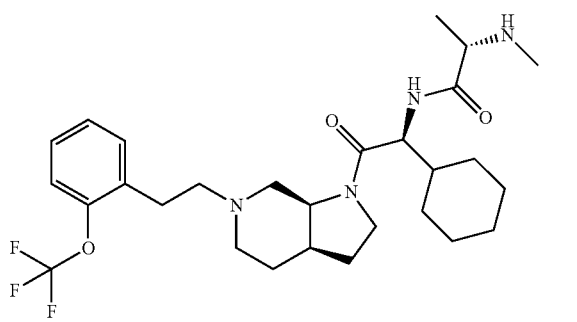 | Example 67<br>MS ESI 539.3 (M + H)+ |
| 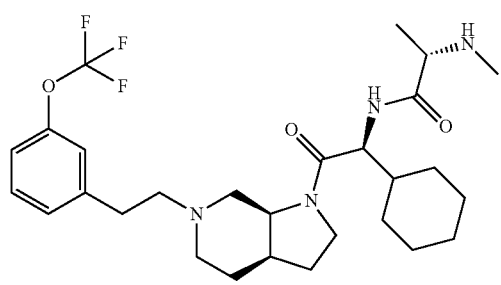 | Example 68<br>MS ESI 539.3 (M + H)+ |
| 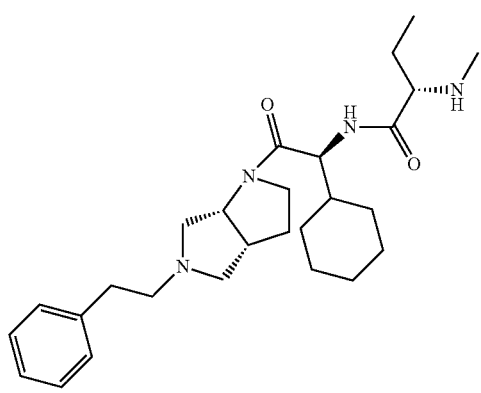 | Example 69<br>MS ESI 455.3 (M + H)+ |

TABLE 1-continued

| Compound Structure | Example Number |
| --- | --- |
| 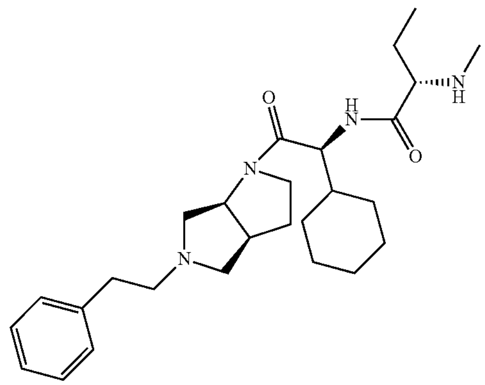 | Example 70<br>MS ESI 455.3 (M + H)+ |
| 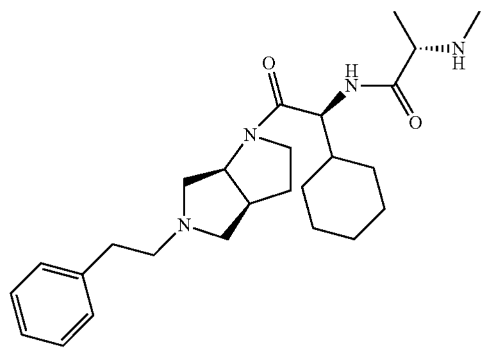 | Example 71<br>MS ESI 441.3 (M + H)+ |
| 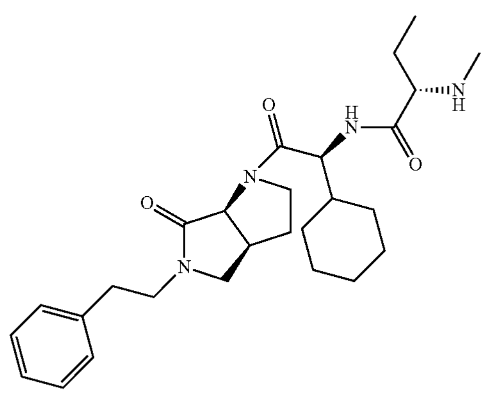 | Example 72<br>MS ESI 469.3 (M + H)+ |
| 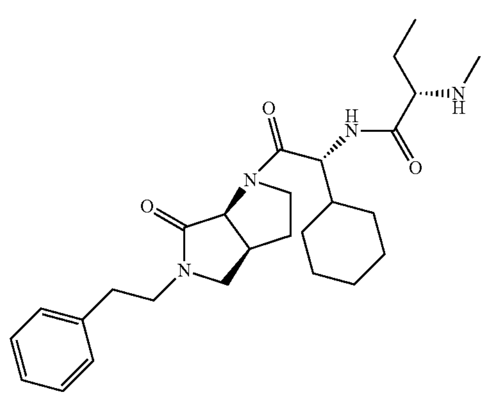 | Example 73<br>MS ESI 469.3 (M + H)+ |

TABLE 1-continued

| Compound Structure | Example Number |
|---|---|
| 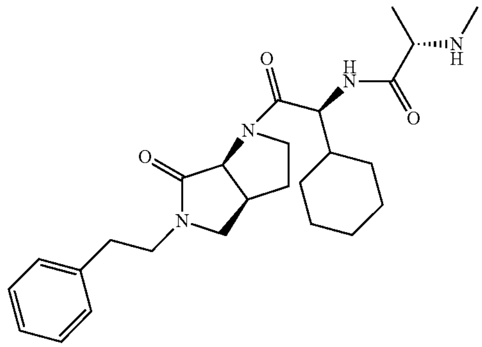 | Example 74<br>MS ESI 455.3 (M + H)+ |
| | Example 75<br>MS ESI 455.3 (M + H)+ |
| 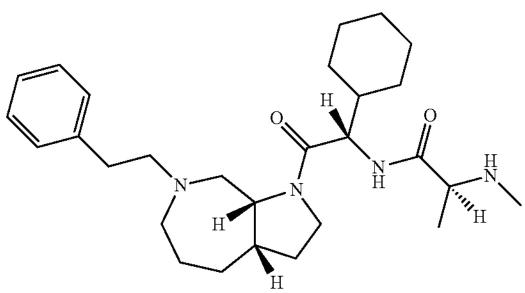 | Example 76<br>MS ESI 469.3 (M + H)+ |
| 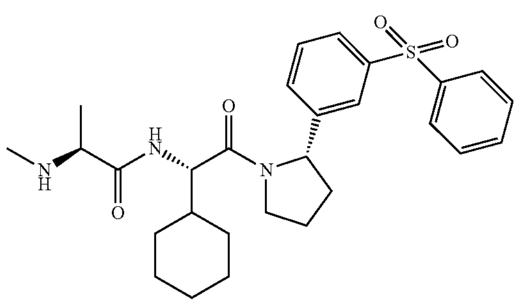 | Example 77<br>MS ESI 512.2 (M + H)+ |
| 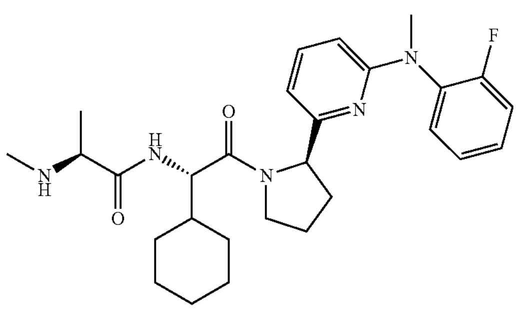 | Example 78<br>MS ESI 496.3 (M + H)+ |

TABLE 1-continued
| Compound Structure | Example Number |
|---|---|
| Additional compounds within the scope of Formula I include: | |
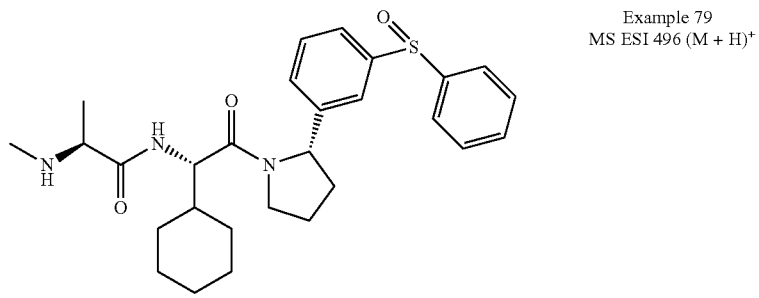
Example 79
MS ESI 496 (M + H)+
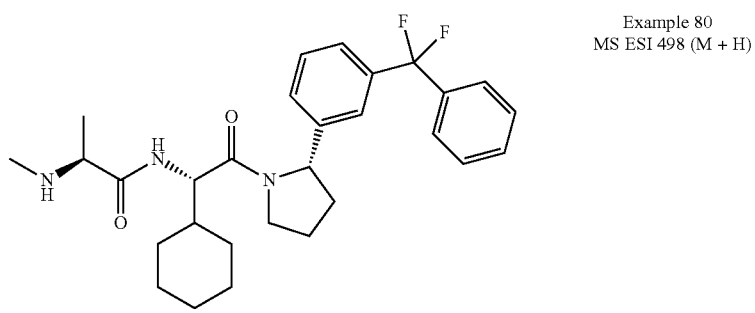
Example 80
MS ESI 498 (M + H)
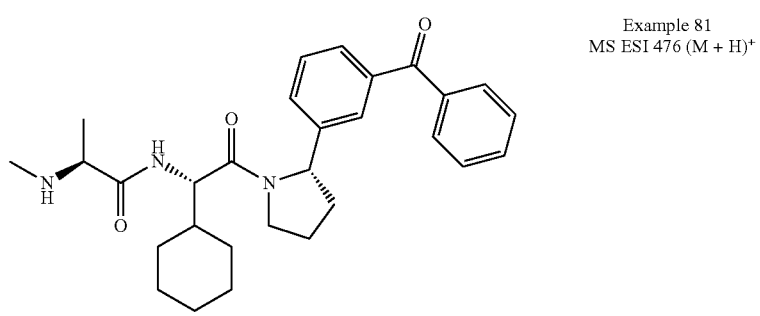
Example 81
MS ESI 476 (M + H)+
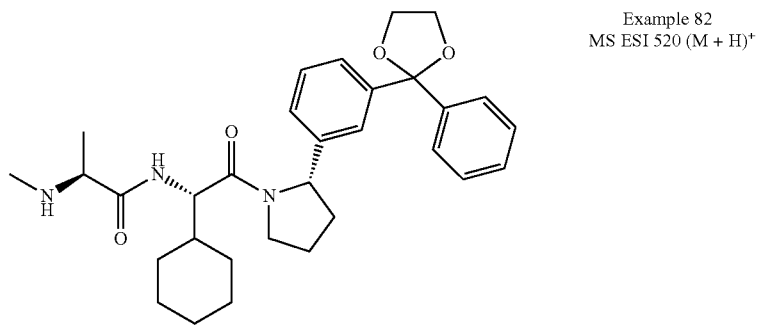
Example 82
MS ESI 520 (M + H)+

TABLE 1-continued

| Compound Structure | Example Number |
|---|---|
| | Example 83<br>MS ESI 424 (M + H)⁺ |
| | Example 84<br>MS ESI 424 (M + H)⁺ |
| | Example 85<br>MS ESI 424 (M + H)⁺ |
| | Example 86<br>MS ESI 396 (M + H)⁺ |
| | Example 87<br>MS ESI 410 (M + H)⁺ |
| | Example 88<br>MS ESI 438 (M + H)⁺ |

TABLE 1-continued
| Compound Structure | Example Number |
|---|---|
| 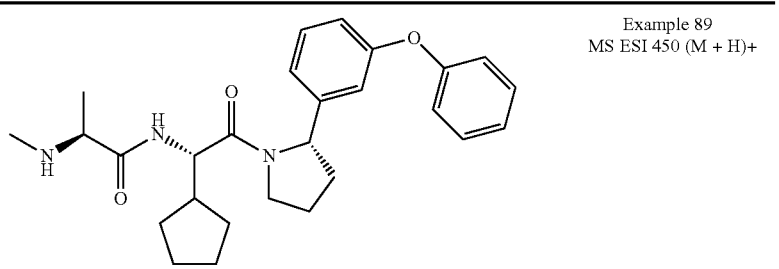 | Example 89<br>MS ESI 450 (M + H)+ |
| 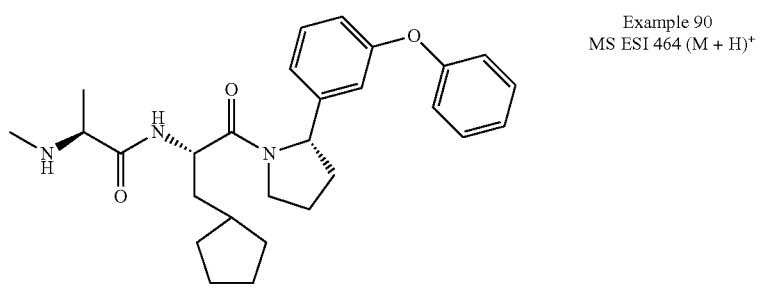 | Example 90<br>MS ESI 464 (M + H)+ |
| 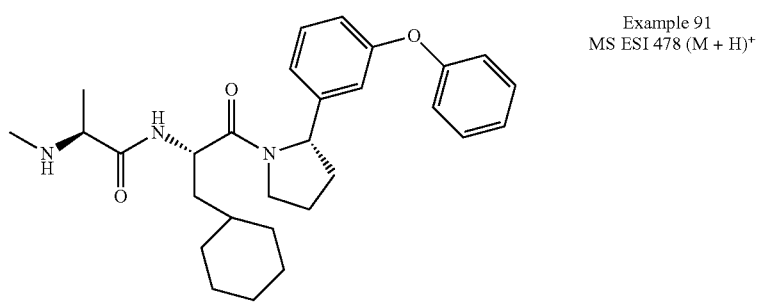 | Example 91<br>MS ESI 478 (M + H)+ |
| 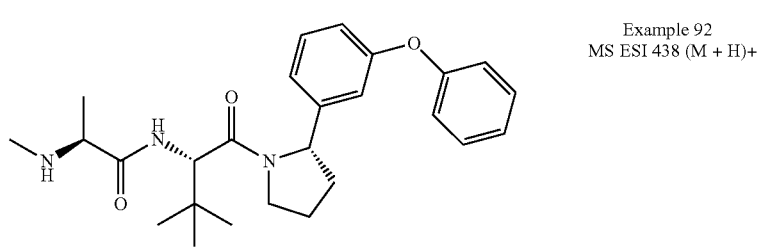 | Example 92<br>MS ESI 438 (M + H)+ |
| 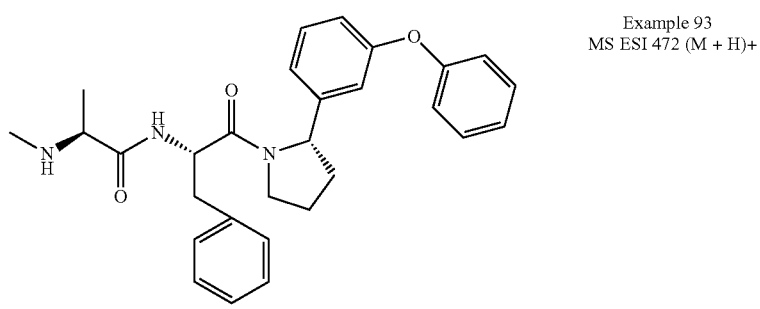 | Example 93<br>MS ESI 472 (M + H)+ |

TABLE 1-continued
| Compound Structure | Example Number |
|---|---|
| 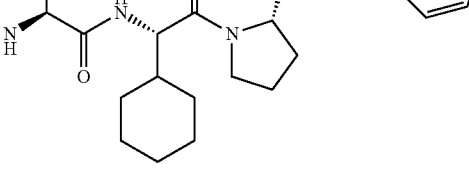 | Example 94<br>MS ESI 465 (M + H)+ |
| 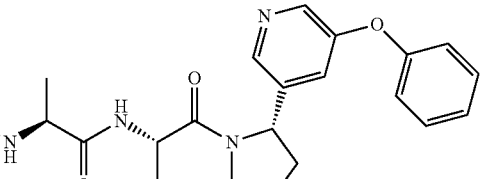 | Example 95<br>MS ESI 465 (M + H)+ |
| 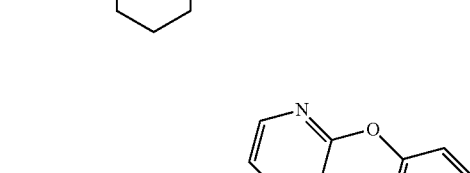 | Example 96<br>MS ESI 465 (M + H)+ |
| 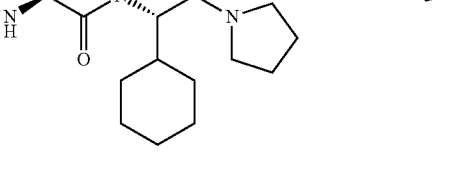 | Example 97<br>MS ESI 466 (M + H)+ |
| 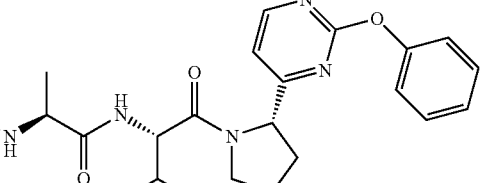 | Example 98<br>MS ESI 465 (M + H)+ |

TABLE 1-continued
| Compound Structure | Example Number |
|---|---|
| 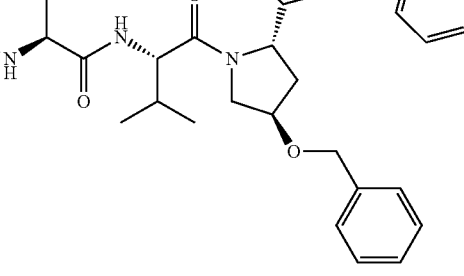 | Example 99<br>MS ESI 529 (M + H)$^+$ |
| 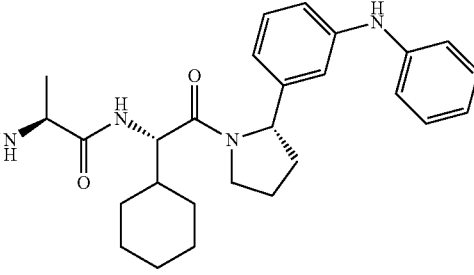 | Example 100<br>MS ESI 463 (M + H)$^+$ |
| 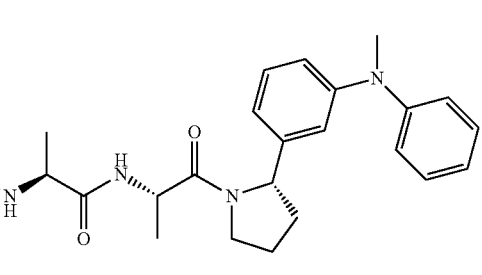 | Example 101<br>MS ESI 409 (M + H)$^+$ |
| 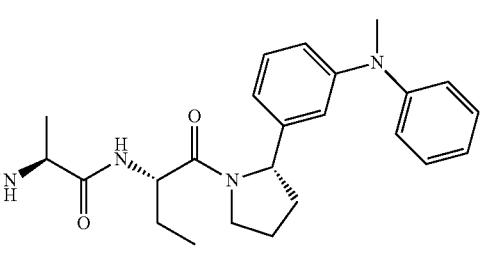 | Example 102<br>MS ESI 423 (M + H)$^+$ |
| 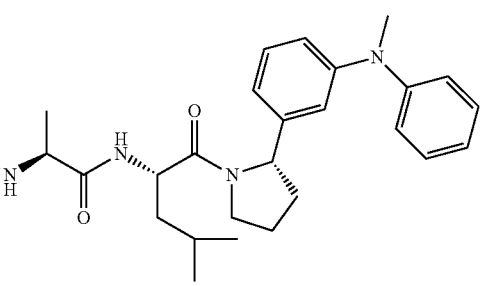 | Example 103<br>MS ESI 451 (M + H)$^+$ |

TABLE 1-continued

| Compound Structure | Example Number |
| --- | --- |
| 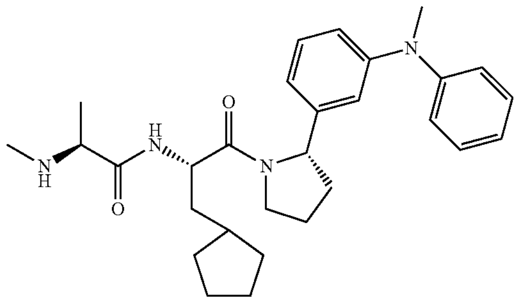 | Example 104<br>MS ESI 477 (M + H)+ |
| 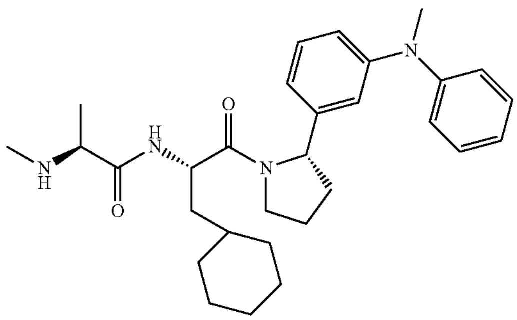 | Example 105<br>MS ESI 491 (M + H)+ |
| 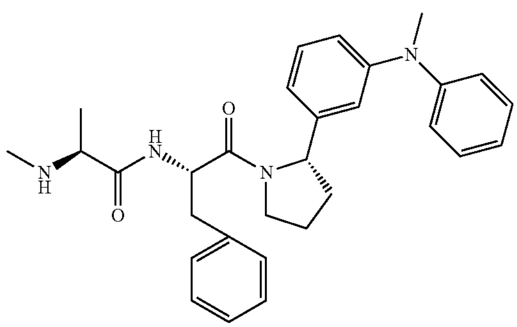 | Example 106<br>MS ESI 485 (M + H)+ |
| 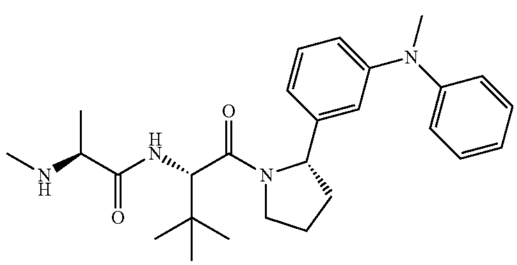 | Example 107<br>MS ESI 451 (M + H)+ |
| 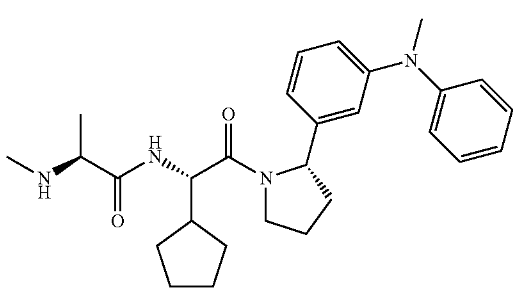 | Example 108<br>MS ESI 463 (M + H)+ |

| Compound Structure | Example Number |
|---|---|
| 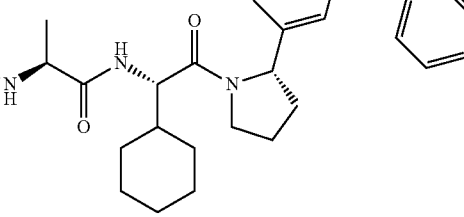 | Example 109<br>MS ESI 541 (M + H)+ |
| 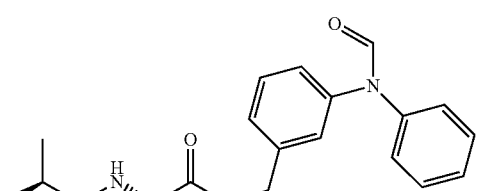 | Example 110<br>MS ESI 491 (M + H)+ |
| 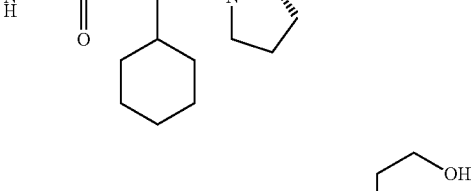 | Example 111<br>MS ESI 507 (M + H)+ |
| 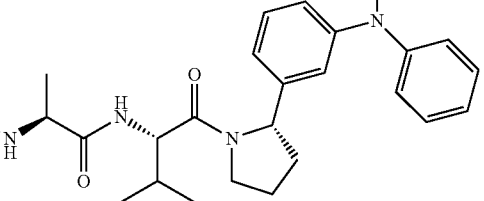 | Example 112<br>MS ESI 531 (M + H)+ |
| 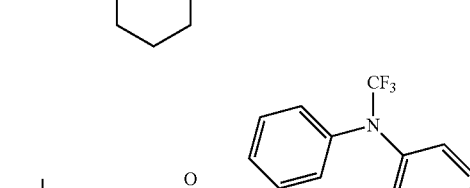 | Example 113<br>MS ESI 497 (M + H)+ |

TABLE 1-continued
| Compound Structure | Example Number |
|---|---|
| 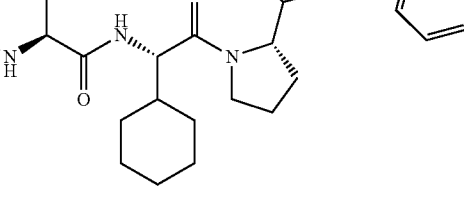 | Example 114<br>MS ESI 496 (M + H)+ |
| 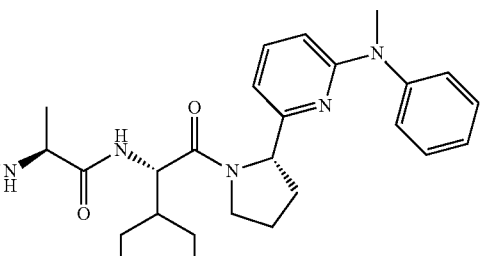 | Example 115<br>MS ESI 478 (M + H)+ |
| 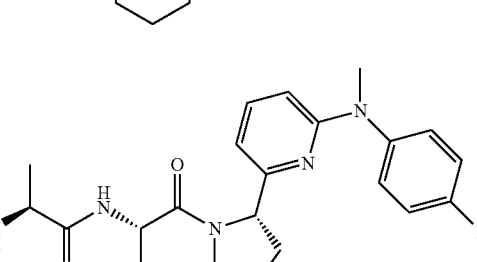 | Example 116<br>MS ESI 496 (M + H)+ |
| 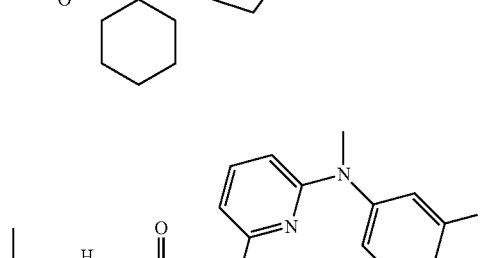 | Example 117<br>MS ESI 512 (M + H)+ |
| 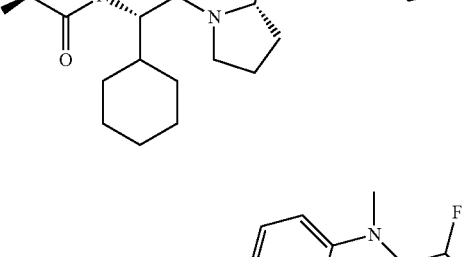 | Example 118<br>MS ESI 514 (M + H)+ |

TABLE 1-continued

| Compound Structure | Example Number |
|---|---|
| | Example 119<br>MS ESI 479 (M + H)⁺ |
| | Example 120<br>MS ESI 478 (M + H)⁺ |
| | Example 121<br>MS ESI 479 (M + H)⁺ |
| | Example 122<br>MS ESI 496 (M + H)⁺ |
| | Example 123<br>MS ESI 453 (M + H)⁺ |

TABLE 1-continued
| Compound Structure | Example Number |
|---|---|
| 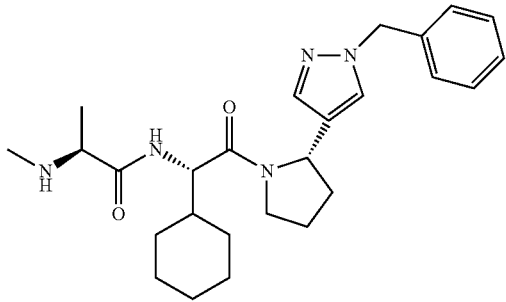 | Example 124<br>MS ESI 452 (M + H)+ |
| 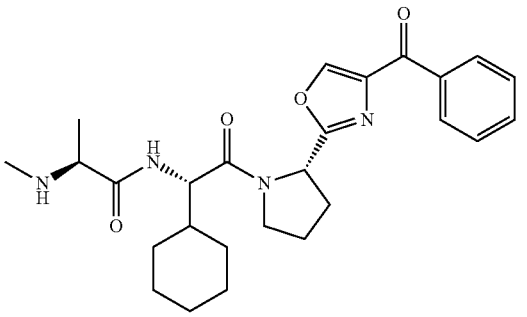 | Example 125<br>MS ESI 467 (M + H)+ |
| 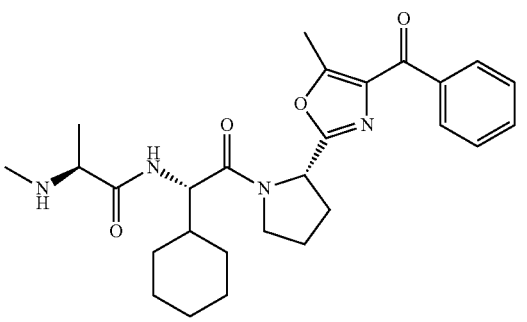 | Example 126<br>MS ESI 481 (M + H)+ |
| 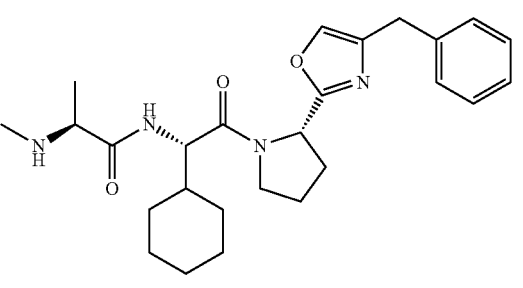 | Example 127<br>MS ESI 453 (M + H) |
| 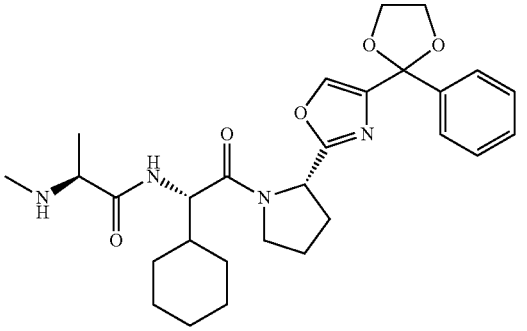 | Example 128<br>MS ESI 511 (M + H)+ |

TABLE 1-continued
| Compound Structure | Example Number |
|---|---|
| 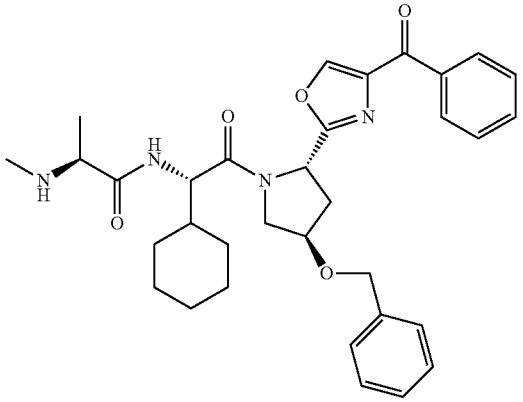 | Example 129<br>MS ESI 573 (M + H)$^+$ |
| 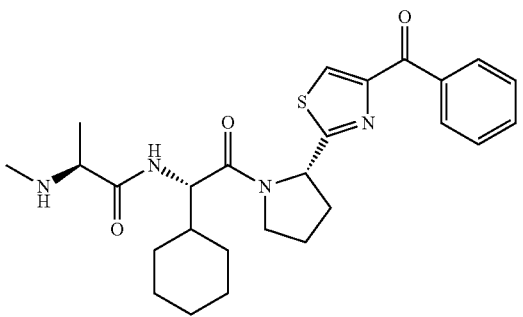 | Example 130<br>MS ESI 483 (M + H)$^+$ |
| 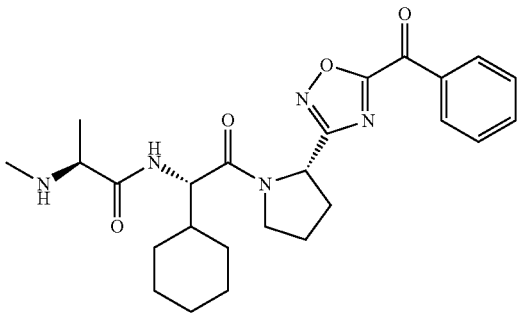 | Example 131<br>MS ESI 468 (M + H)$^+$ |
| 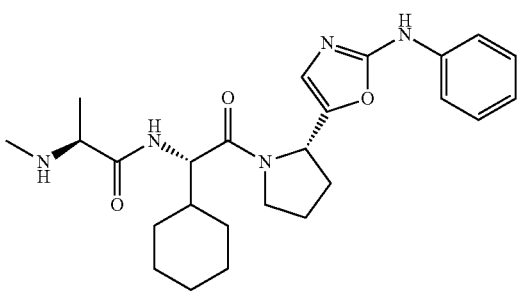 | Example 132<br>MS ESI 454 (M + H)$^+$ |

TABLE 1-continued

| Compound Structure | Example Number |
|---|---|
| 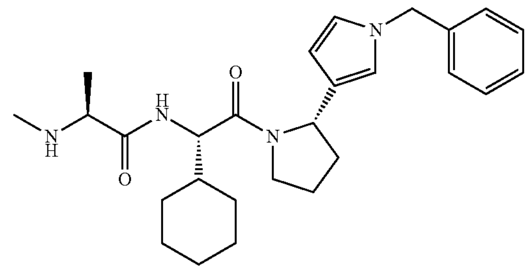 | Example 133<br>MS ESI 451 (M + H)+ |
| 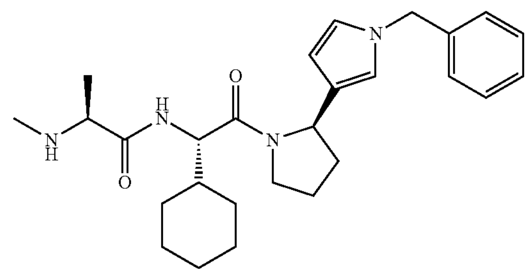 | Example 134<br>MS ESI 451 (M + H) |
| 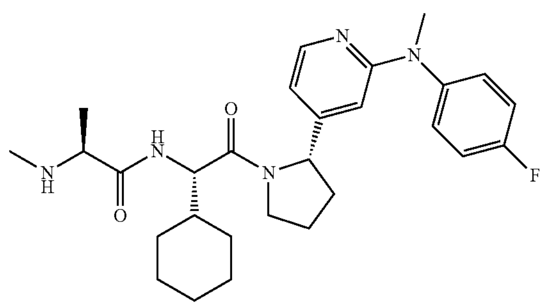 | Example 135<br>MS ESI 510 (M + H)+ |
| 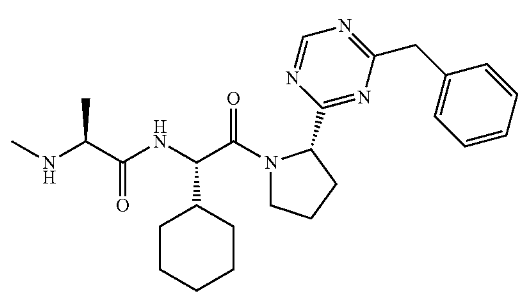 | Example 136<br>MS ESI 465 (M + H) |
| 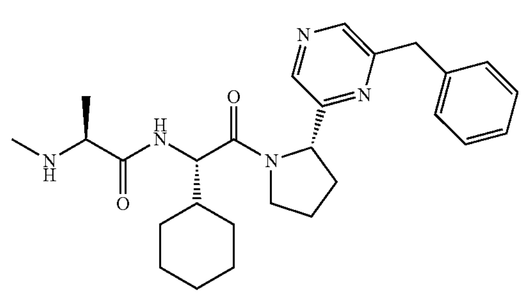 | Example 137<br>MS ESI 464 (M + H)+ |

TABLE 1-continued

| Compound Structure | Example Number |
|---|---|
| | Example 138<br>MS ESI 452 (M + H)⁺ |
| | Example 139<br>MS ESI 454 (M + H)⁺ |
| | Example 140<br>MS ESI 535 (M + H)⁺ |
| | Example 141<br>MS ESI 405 (M + H)⁺ |
| | Example 142<br>MS ESI 473 (M + H)⁺ |

TABLE 1-continued
| Compound Structure | Example Number |
|---|---|
| 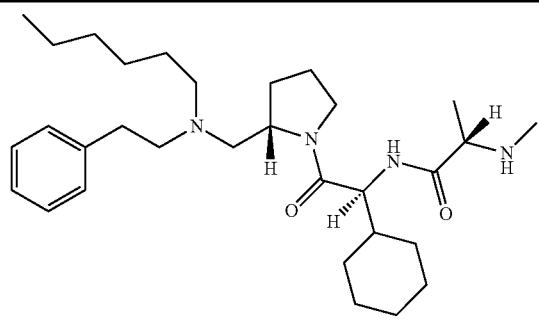 | Example 143<br>MS ESI 513 (M + H)+ |
| 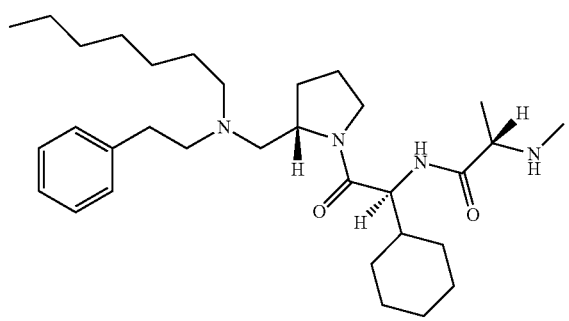 | Example 144<br>MS ESI 527 (M + H)+ |
| 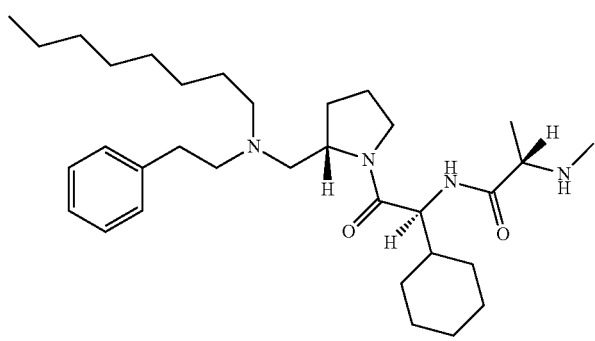 | Example 145<br>MS ESI 541 (M + H)+ |
| 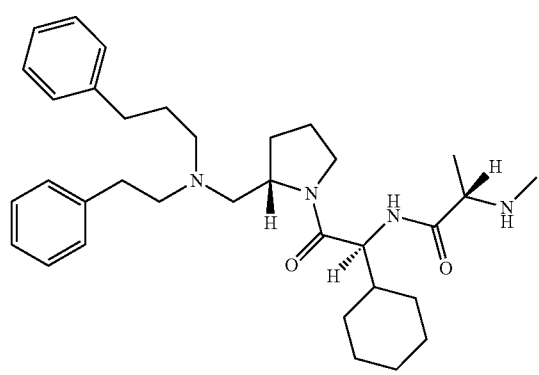 | Example 146<br>MS ESI 547 (M + H)+ |

TABLE 1-continued

| Compound Structure | Example Number |
|---|---|
| 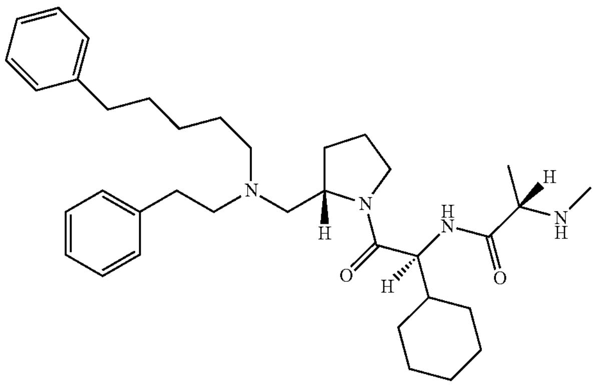 | Example 147<br>MS ESI 575 (M + H)+ |
| 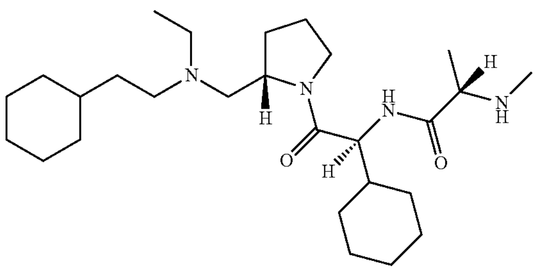 | Example 148<br>MS ESI 463 (M + H)+ |
| 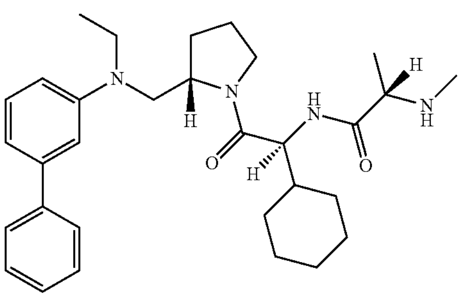 | Example 149<br>MS ESI 505 (M + H)+ |
| 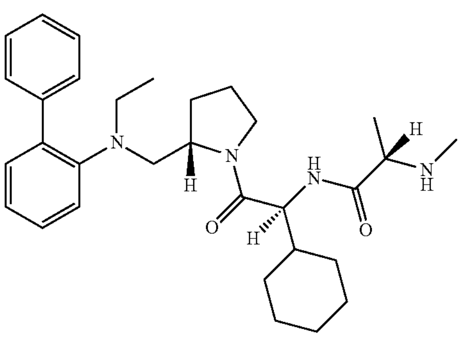 | Example 150<br>MS ESI 505 (M + H)+ |
| 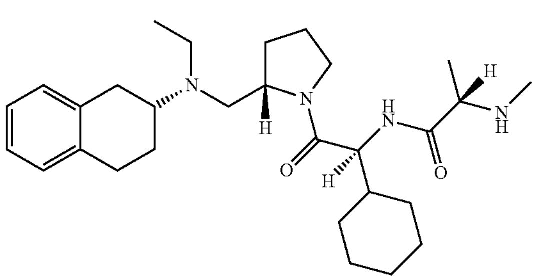 | Example 151<br>MS ESI 483 (M + H)+ |

TABLE 1-continued
| Compound Structure | Example Number |
|---|---|
| 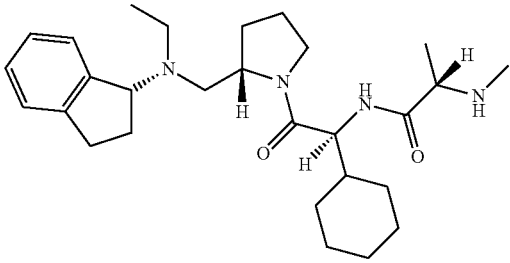 | Example 152<br>MS ESI 469 (M + H)+ |
| 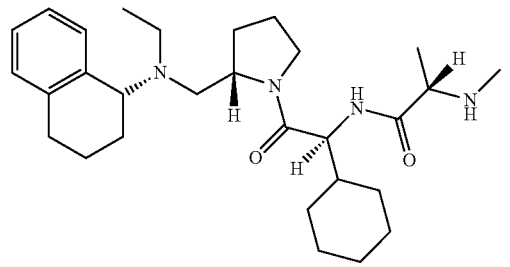 | Example 153<br>MS ESI 483 (M + H)+ |
| 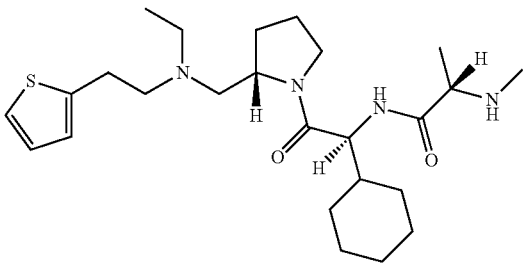 | Example 154<br>MS ESI 463 (M + H)+ |
| 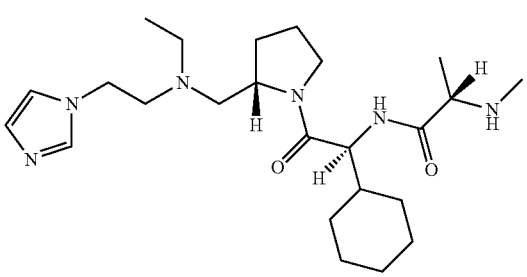 | Example 155<br>MS ESI 447 (M + H)+ |
| 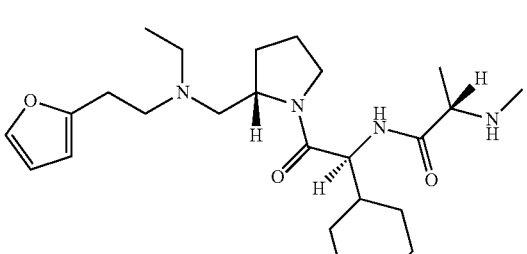 | Example 156<br>MS ESI 447 (M + H)+ |

TABLE 1-continued

| Compound Structure | Example Number |
|---|---|
| 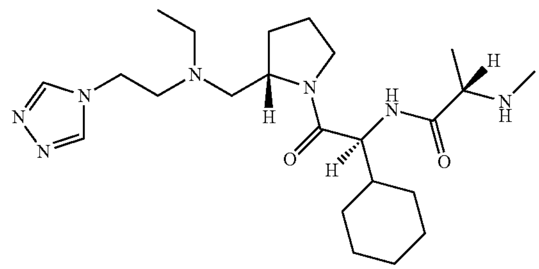 | Example 157<br>MS ESI 448 (M + H)+ |
| 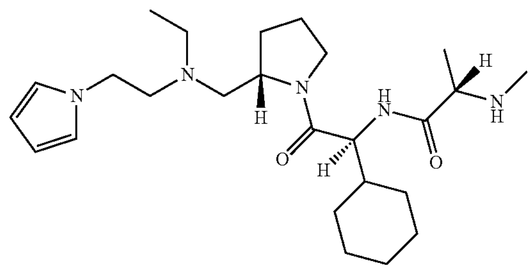 | Example 158<br>MS ESI 446 (M + H)+ |
| 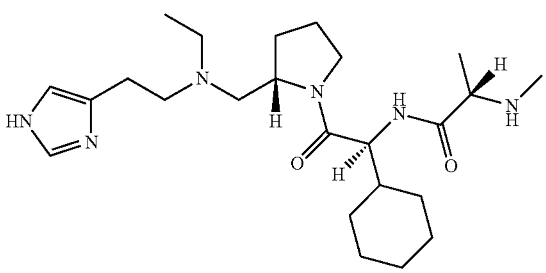 | Example 159<br>MS ESI 447 (M + H)+ |
| 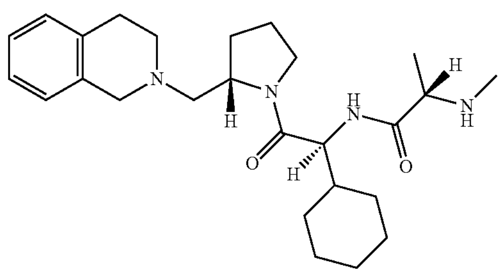 | Example 160<br>MS ESI 441 (M + H)+ |
| 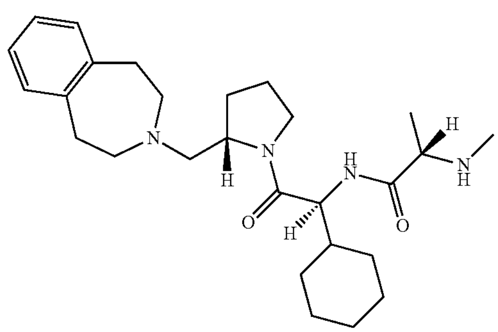 | Example 161<br>MS ESI 455 (M + H)+ |

TABLE 1-continued
| Compound Structure | Example Number |
|---|---|
| 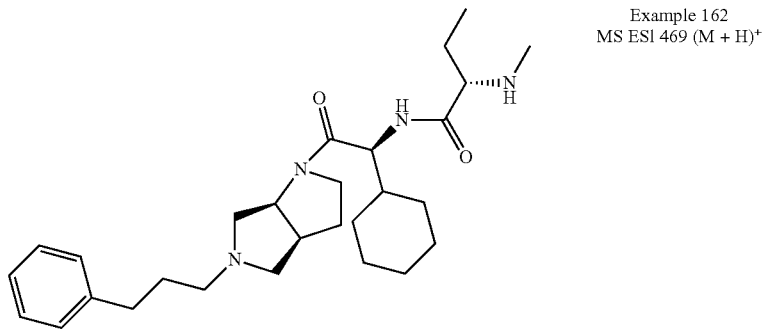 | Example 162<br>MS ESI 469 (M + H)+ |
| 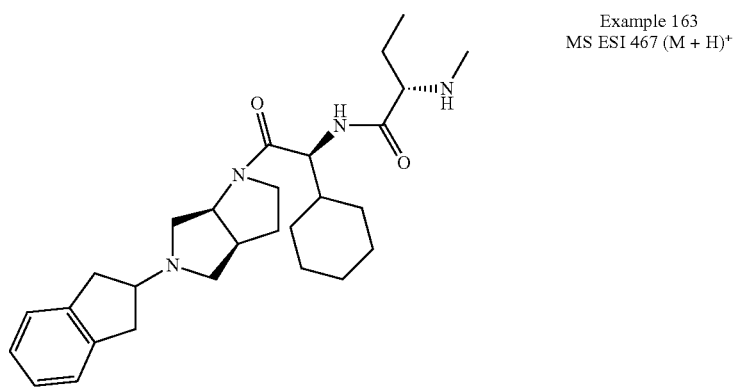 | Example 163<br>MS ESI 467 (M + H)+ |
| 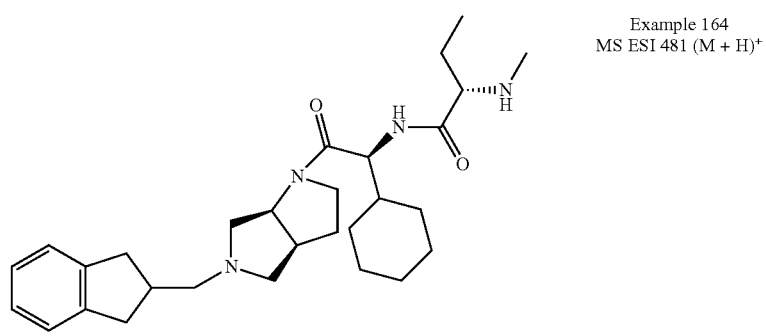 | Example 164<br>MS ESI 481 (M + H)+ |
| 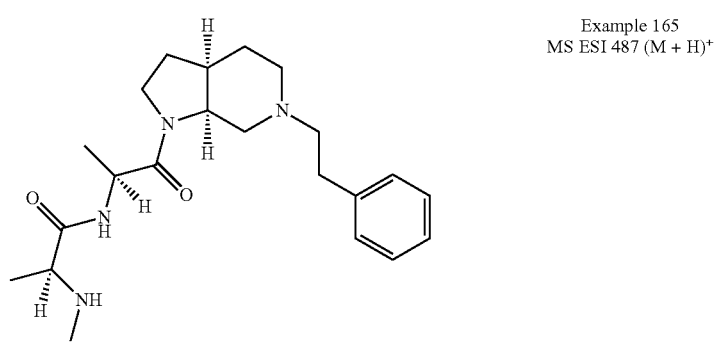 | Example 165<br>MS ESI 487 (M + H)+ |

TABLE 1-continued

| Compound Structure | Example Number |
| --- | --- |
| 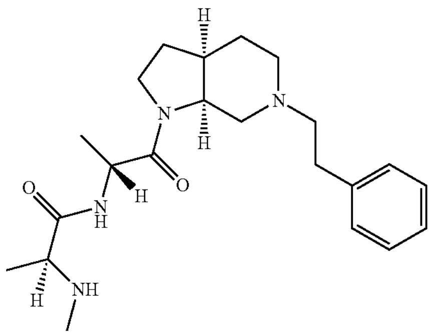 | Example 166<br>MS ESI 387 (M + H)+ |
| 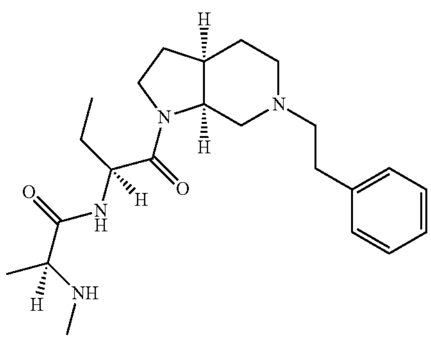 | Example 167<br>MS ESI 401 (M + H)+ |
| 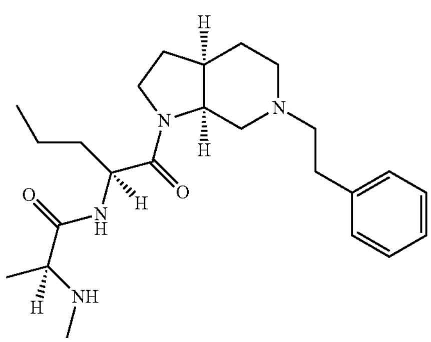 | Example 168<br>MS ESI 415 (M + H)+ |
| 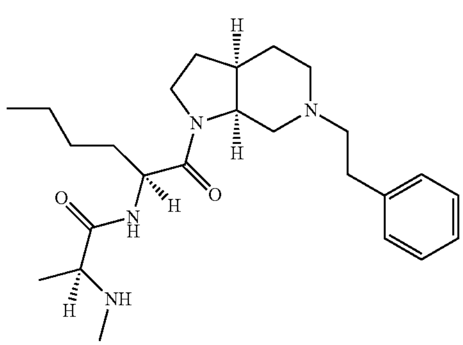 | Example 169<br>MS ESI 429 (M + H)+ |

TABLE 1-continued
| Compound Structure | Example Number |
|---|---|
| 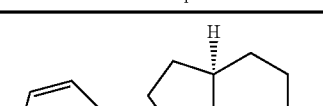 | Example 170<br>MS ESI 449 (M + H)+ |
| 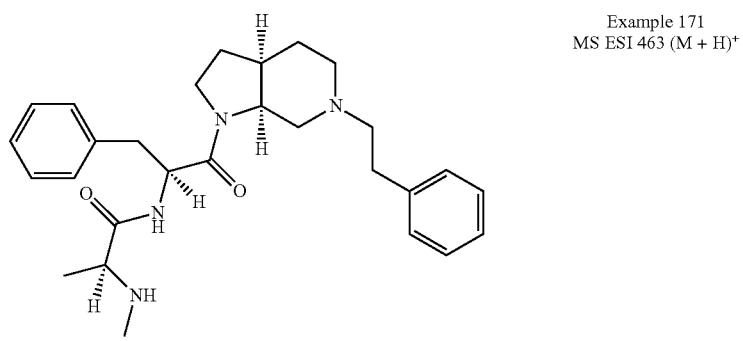 | Example 171<br>MS ESI 463 (M + H)+ |
| 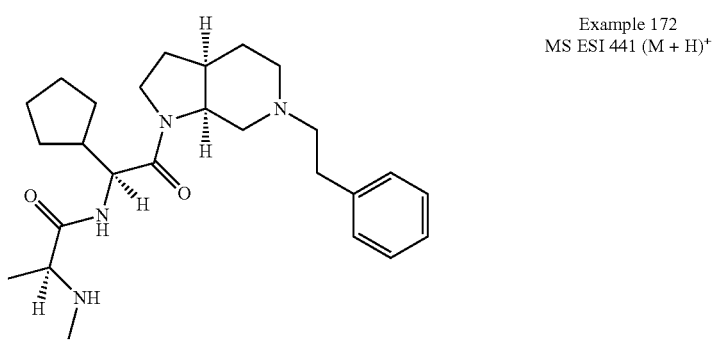 | Example 172<br>MS ESI 441 (M + H)+ |
| 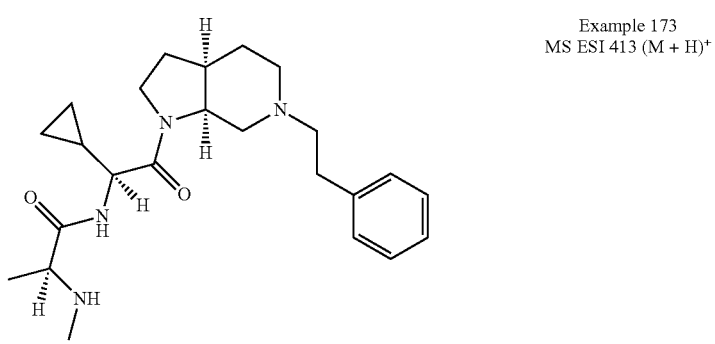 | Example 173<br>MS ESI 413 (M + H)+ |

TABLE 1-continued
| Compound Structure | Example Number |
|---|---|
| 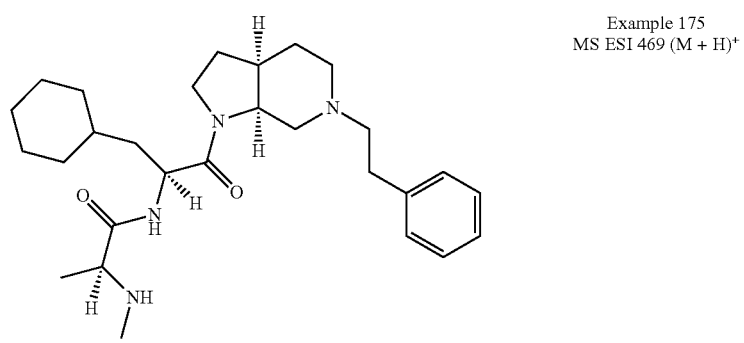 | Example 174<br>MS ESI 455 (M + H)+ |
| 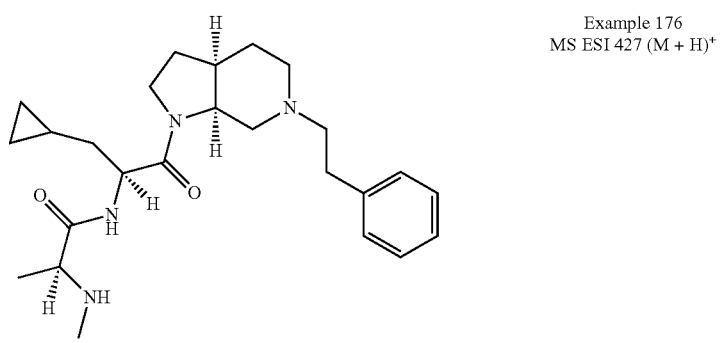 | Example 175<br>MS ESI 469 (M + H)+ |
| 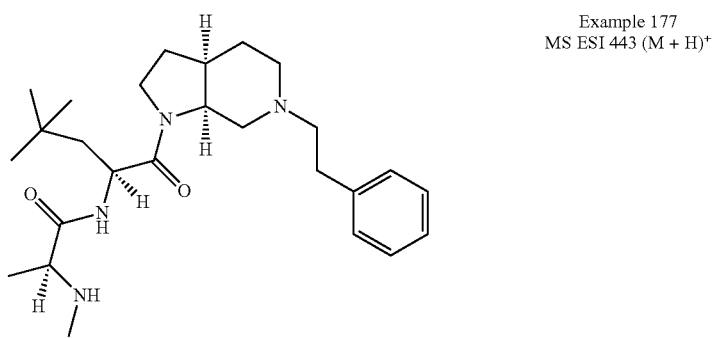 | Example 176<br>MS ESI 427 (M + H)+ |
| 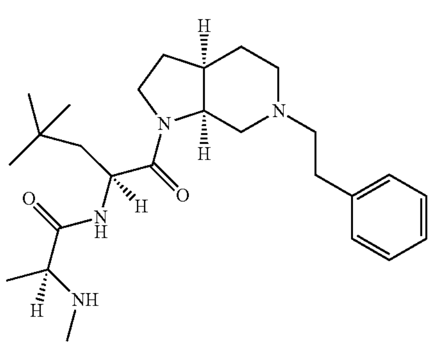 | Example 177<br>MS ESI 443 (M + H)+ |

TABLE 1-continued
| Compound Structure | Example Number |
|---|---|
| 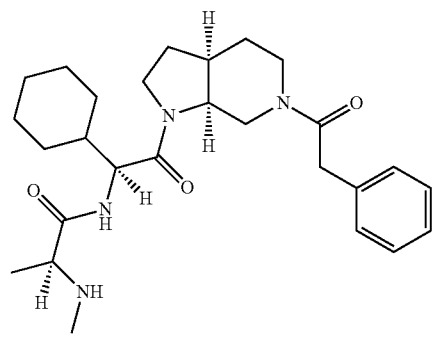 | Example 178<br>MS ESI 469 (M + H)+ |
| 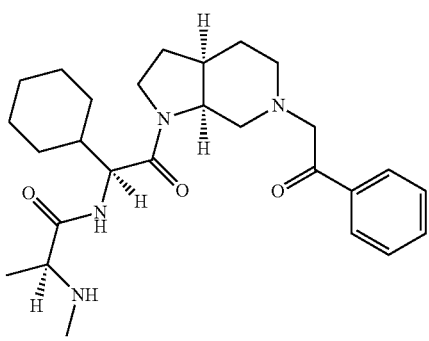 | Example 179<br>MS ESI 469 (M + H)+ |
| 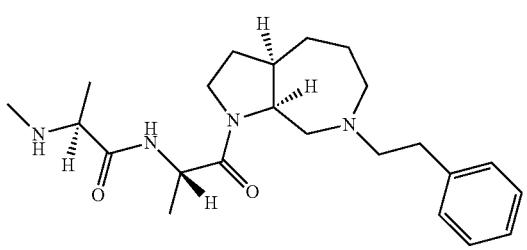 | Example 180<br>MS ESI 401 (M + H)+ |
| 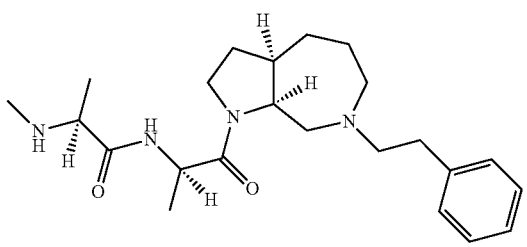 | Example 181<br>MS ESI 401 (M + H)+ |
| 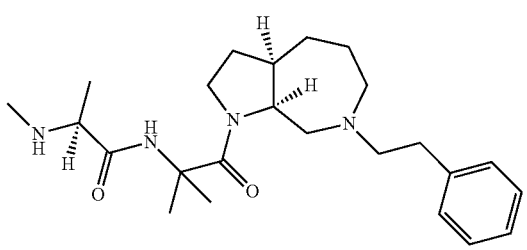 | Example 182<br>MS ESI 415 (M + H)+ |

TABLE 1-continued

| Compound Structure | Example Number |
|---|---|
| 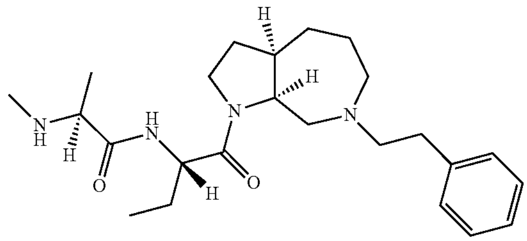 | Example 183<br>MS ESI 415 (M + H)+ |
| 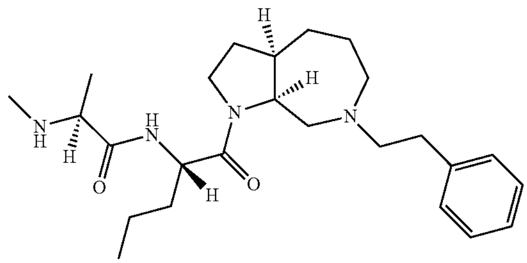 | Example 184<br>MS ESI 429 (M + H)+ |
| 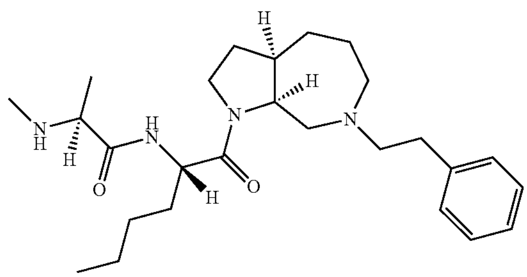 | Example 185<br>MS ESI 443 (M + H)+ |
| 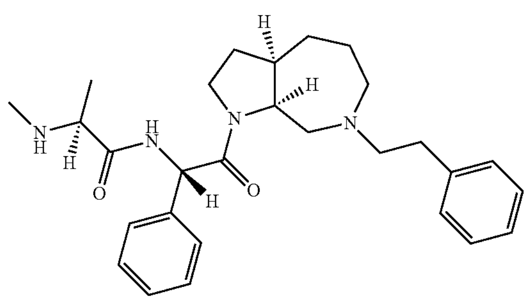 | Example 186<br>MS ESI 463 (M + H)+ |
| 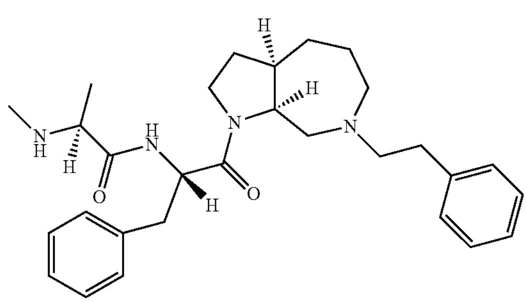 | Example 187<br>MS ESI 477 (M + H)+ |

TABLE 1-continued
| Compound Structure | Example Number |
|---|---|
| 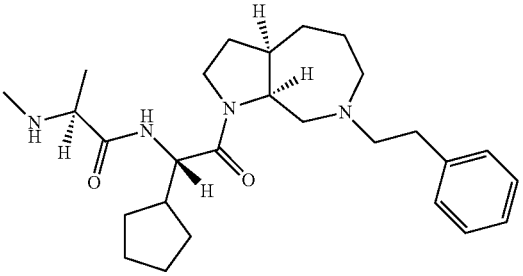 | Example 188<br>MS ESI 455 (M + H)+ |
| 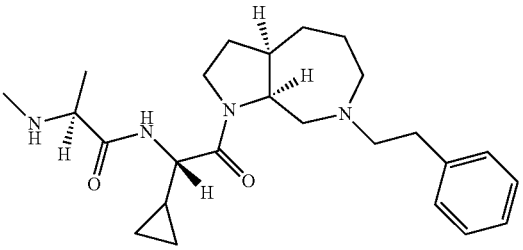 | Example 189<br>MS ESI 427 (M + H)+ |
| 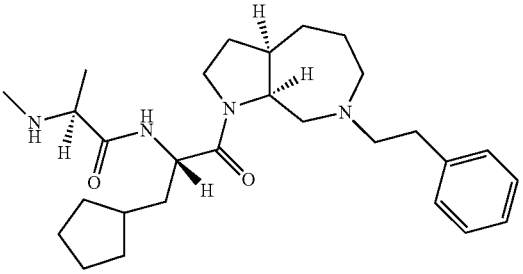 | Example 190<br>MS ESI 469 (M + H)+ |
| 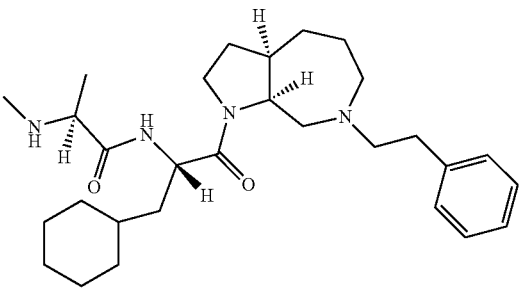 | Example 191<br>MS ESI 483 (M + H)+ |
| 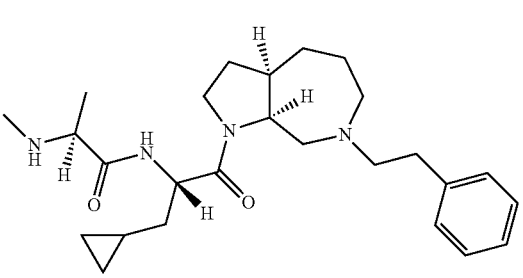 | Example 192<br>MS ESI 441 (M + H)+ |

TABLE 1-continued
| Compound Structure | Example Number |
|---|---|
| 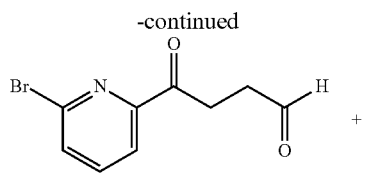 | Example 193<br>MS ESI 457 (M + H)+ |
| 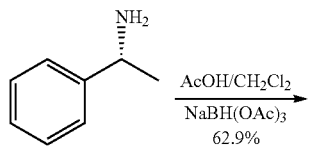 | Example 194<br>MS ESI 415 (M + H)+ |
Example 195
(S)—N—[(S)-1-Cyclohexyl-2-((R)-2-{6-[(2-fluoro-phenyl)-methyl-amino]-pyridin-2-yl}-pyrrolidin-1-yl)-2-oxo-ethyl]-2-methylamino-propionamide (78)
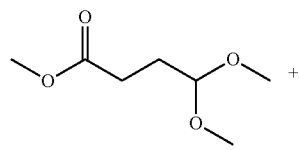
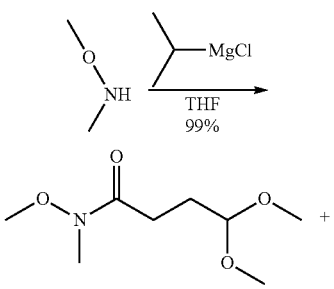
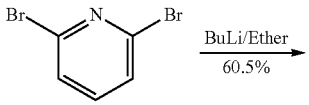
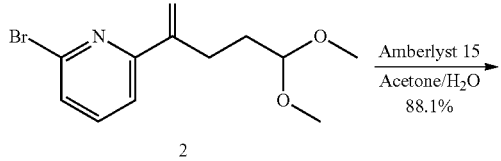
-continued
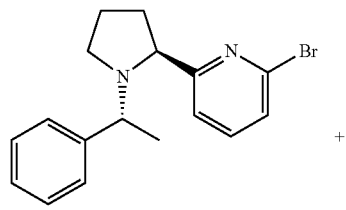
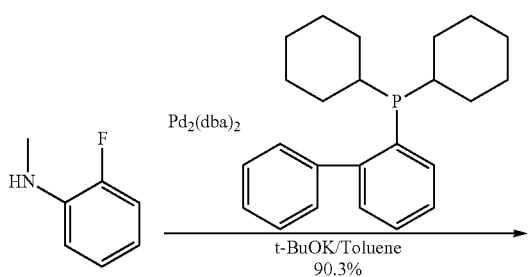

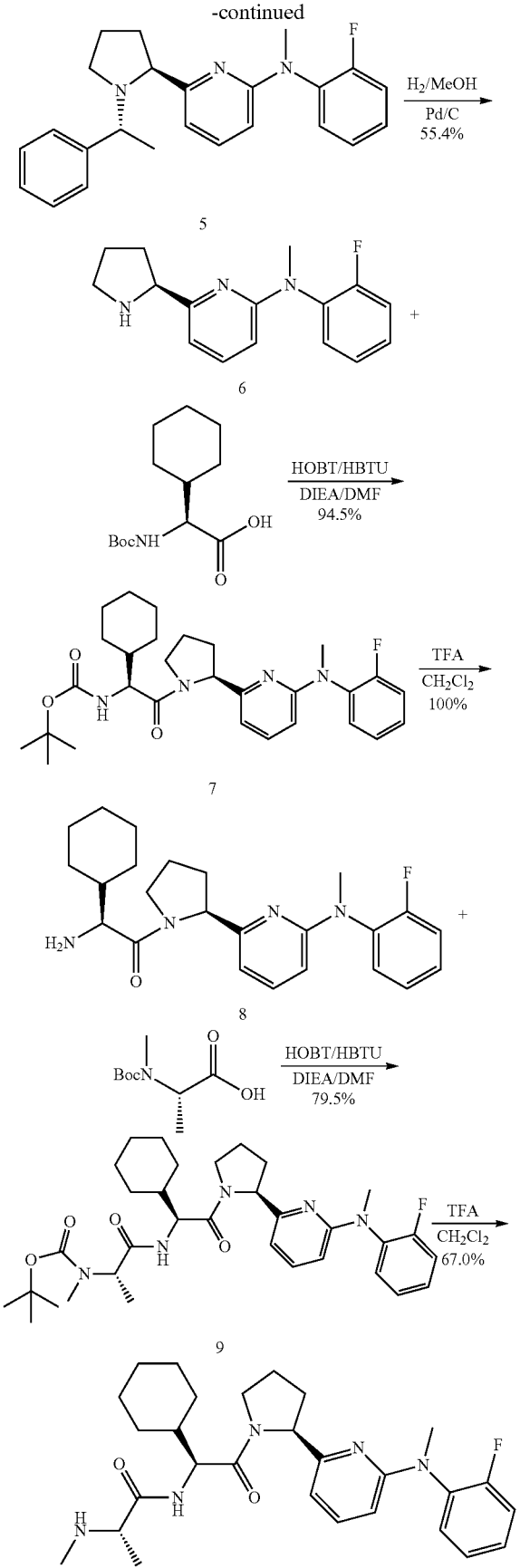

4,4,N-Trimethoxy-N-methyl-butyramide (1)

To a solution of methyl 4,4-dimethoxy-butyrate (4.99 g, 30.8 mmol) and N, O-dimethylhydroxylamine HCl (4.65 g, 47.68 mmol) in 60 mL of THF at −20° C., is added isopropylmagnesiumchloride (46 mL, 92.28 mmol, 2.0M in THF) maintaining the temperature below −20° C. After stirring at −10° C. for 30 min, the reaction mixture is quenched with 50 mL of water and extracted with 3×80 mL of EtOAc. The combined organic layers is dried over $Na_2SO_4$ and filtered through a short silica gel pluge. The solution is concentrated to give 4,4,N-Trimethoxy-N-methyl-butyramide (5.9 g, 99%) as pale liquid. M/Z=191.0

N-[1-Eth-(Z)-ylidene-5,5-dimethoxy-2-oxo-pentyl]-acrylimidoyl bromide (2)

To a suspension of 2,6-dibromopyridine (8.1 g, 34.03 mmol) in 80 mL of ether at −70° C., is added BuLi (12.3 mL, 26.17 mmol, 2.5 M in Hexane) in on portion. After stirring at −70° C. for 5 min, 4,4,N-Trimethoxy-N-methyl-butyramide (5.0 g, 26.17 mmol) is added to the solution dropwise. After stirring at −70° C. for 1.5 hr, the reaction mixture is quenched with 120 mL of water and extracted with 3×130 mL of EtOAc. The combined organic layers is concentrated and purified by chromatography (Hexane/EtOAc:70/30) to give N-[1-Eth-(Z)-ylidene-5,5-dimethoxy-2-oxo-pentyl]-acrylimidoyl bromide (5.96 g, 60.5%) as light yellow liquid. M/Z=288.0

N-[1-Eth-(Z)-ylidene-2,5-dioxo-pentyl]-acrylimidoyl bromide (3)

To a solution of N-[1-Eth-(Z)-ylidene-5,5-dimethoxy-2-oxo-pentyl]acrylimidoyl bromide (7.0 g, 28.9 mmol) in a solution of acetone (30 mL) and water (1.5 mL) at room temperature, is added Amberlyse-15 (20 g). After mechanical shacking for 3 hr at room temperature, the reaction mixture is filtered. The resin beads were washed with acetone (contain 10% of $Et_3N$). The combined organic layers were concentrated and purified by chromatography (Hexane/EtOAc: 70/30) to yield N-[1-Eth-(Z)-ylidene-2,5-dioxo-pentyl]-acrylimidoyl bromide (5.18 g, 88.1%) as light yellow liquid. M/Z=421, 243.9 [M+1]

2-Bromo-6-[(S)-1-((R)-1-phenyl-ethyl)-pyrrolidin-2-yl]-pyridine (4)

To a solution of N-[1-Eth-(Z)-ylidene-2,5-dioxo-pentyl]-acrylimidoyl bromide (1.0 g, 4.1 mmol) and R(+)-α-methyl-benzylamine (0.5 g, 4.1 mmol) in 17 mL of $CH_2Cl_2$ at −70° C., is added acetic acid (0.6 mL) and sodium triacetoxyborohydride (1.74 g, 8.2 mmol). After stirring at −70° C. for 40 min, the dry ice bath is removed, and the reaction solution is warmed to room temperature. After stirring at room temperature overnight, the reaction mixture is quenched with 20 mL of water and extracted with 3×30 mL of $CH_2Cl_2$. The combined organic layers were concentrated and purified by chromatography (Hexane/EtOAc: 70/30) to yield 2-Bromo-6-[(S)-1-((R)-1-phenyl-ethyl)-pyrrolidin-2-yl]-pyridine (0.86 g, 62.9%) as light yellow liquid. M/Z=332.7 [M+1]

(Z)—N-(2-Fluoro-phenyl)-N-methyl-N'-[1-[(S)-1-((R)-1-phenyl-ethyl)-pyrrolidin-2-yl]-prop-2-en-(E)-ylidene]-propenamidine (5)

To a solution of 2-Bromo-6-[(S)-1-((R)-1-phenyl-ethyl)-pyrrolidin-2-yl]-pyridine (86.5 mg, 2.57 mmol), 2-fluoromethyaniline (64.7 mg, 5.14 mmol) and 2-(di-cyclohexylphosphino)-biphenyl (38.5 mg, 0.13 mmol) in 20 mL of toluene at room temperature, were added Pd$_2$(dba)$_3$ (117.6 mg, 0.13 mmol). The reaction mixture is stirred at 80° C. for 2 hrs, and then cooled to room temperature. The reaction mixture is filtered through celite, and the filtrate is diluted with 50 mL of EtOAc and washed with 2×50 mL of water. The combined organic layers were concentrated and purified by chromatography (CH$_2$Cl$_2$/MeOH: 97/3) to give (Z)—N-(2-Fluoro-phenyl)-N-methyl-N'-[1-[(S)-1-((R)-1-phenyl-ethyl)-pyrrolidin-2-yl]-prop-2-en-(E)-ylidene]-propenamidine (870 mg, 90.3%) as pale solid. M/Z=376.0 [M+1]

(Z)—N-(2-Fluoro-phenyl)-N-methyl-N'-[1-[(S)-1-((R)-1-phenyl-ethyl)-pyrrolidin-2-yl]-prop-2-en-(E)-ylidene]-propenamidine (6)

(Z)—N-(2-Fluoro-phenyl)-N-methyl-N'-[1-[(S)-1-((R)-1-phenyl-ethyl)-pyrrolidin-2-yl]-prop-2-en-(E)-ylidene]-propenamidine (500 mg, 1.33 mmol) is dissolved in 10 mL of MeOH in a 500 mL round bottle flask with 300 mg of Pd/C. The reaction mixture is stirred under H$_2$ gas (1 atm) from a balloon for 24 hours. After degassing under vacuum, the reaction mixture is filtered to remove catalyst. The crude product is purified by reverse phase HPLC to give (Z)—N-(2-Fluoro-phenyl)-N-methyl-N'-[1-[(S)-1-((R)-1-phenyl-ethyl)-pyrrolidin-2-yl]-prop-2-en-(E)-ylidene]-propenamidine (200 mg, 55.4%) as yellow oil. M/Z=272.07 [M+1]

[(S)-1-Cyclohexyl-2-((S)-2-{1-[(E)-(Z)—N-(2-fluoro-phenyl)-N-methyl-1-imioxo-propenylimino]-allyl}-pyrrolidin-1-yl)-2-oxo-ethyl]-carbamic acid tert-butyl ester (7)

To a solution of Boc-L-a-cyclohexyglycine (204 mg, 0.79 mmol) in 5 mL of DMF at room temperature, is added diisopropylethylamine (0.58 mL, 3.3 mmol) slowly. After stirring at room temperature for 20 minutes, a solution of HOBT (116 mg, 0.86 mmol) and HBTU (325 mg, 0.86 mmol) in DMF (5 mL) is added to the reaction mixture, and the solution is transferred to another flask contained (Z)—N-(2-Fluoro-phenyl)-N-methyl-N'-[(S)-1-pyrrolidin-2-yl-prop-2-en-(E)-ylidene]-propenamidine (180 mg, 0.66 mmol). After stirring for 1 hr, the reaction solution is diluted with EtOAc (50 mL), and washed with water (3×20 mL). The combined organic layers is concentrated. The crude product is diluted with CH$_2$Cl$_2$ (10 mL) and dried over Na$_2$SO$_4$, and purified by chromatography (CH$_2$Cl$_2$/MeOH: 97/3) to give [(S)-1-Cyclohexyl-2-((S)-2-{1-[(E)-(Z)—N-(2-fluoro-phenyl)-N-methyl-1-imioxo-propenylimino]-allyl}-pyrrolidin-1-yl)-2-oxo-ethyl]-carbamic acid tert-butyl ester (320 mg, 94.5%) as pale gum. M/Z=511.14[M+1]

(Z)—N'-[1-[(S)-1-((S)-2-Amino-2-cyclohexyl-acetyl)-pyrrolidin-2-yl]-prop-2-en-(E)-ylidene]-N-(2-fluoro-phenyl)-N-methyl-propenamidine (8)

To a solution of [(S)-1-Cyclohexyl-2-((S)-2-{1-[(E)-(Z)—N-(2-fluoro-phenyl)-N-methyl-1-imioxo-propenylimino]-allyl}-pyrrolidin-1-yl)-2-oxo-ethyl]-carbamic acid tert-butyl ester (320 mg, 0.63 mmol) in CH$_2$Cl$_2$ (3 mL) at −20° C. is added TFA (5 ML, pre-cooled to −20° C.) slowly. After stirring at 0° C. for 30 min, the reaction mixture is concentrated to remove most of TFA. The residue is dissolved in 20 mL of CH$_2$Cl$_2$, and neutralized with 10% NH$_4$OH to PH=8. The solution is dried over Na$_2$SO$_4$ and concentrated to give (Z)—N'-[1-[(S)-1-((S)-2-Amino-2-cyclohexyl-acetyl)-pyrrolidin-2-yl]-prop-2-en-(E)-ylidene]-N-(2-fluoro-phenyl)-N-methyl-propenamidine (260 mg, quantitative) as pale gum without further purification for next step reaction. M/Z=411.2 [M+1]

{(S)-1-[(S)-1-Cyclohexyl-2-((S)-2-{6-[(2-fluoro-phenyl)-methyl-amino]-pyridin-2-yl}-pyrrolidin-1-yl)-2-oxo-ethylcarbamoyl]-ethyl}-methyl-carbamic acid tert-butyl este (9)

To a solution of Boc-N-methyl-L-a-alanine (155 mg, 0.76 mmol) in 5 mL of DMF at room temperature, is added diisopropylethylamine (0.58 mL, 3.3 mmol) slowly. After stirring at room temperature for 20 minutes, a solution of HOBT (111 mg, 0.82 mmol) and HBTU (311 mg, 0.82 mmol) in DMF (5 mL) is added to the reaction mixture, and the solution is transferred to another flask contained (Z)—N'-[1-[(S)-1-((S)-2-Amino-2-cyclohexyl-acetyl)-pyrrolidin-2-yl]-prop-2-en-(E)-ylidene]-N-(2-fluoro-phenyl)-N-methyl-propenamidine (260 mg, 0.63 mmol). After stirring for 1 hr, the reaction solution is diluted with EtOAc (50 mL), and washed with water (3×20 mL). The combined organic layers is concentrated. The crude product is diluted with CH$_2$Cl$_2$ (10 mL) and dried over Na$_2$SO$_4$, and purified by chromatography (CH$_2$Cl$_2$/MeOH: 97/3) to give {(S)-1-[(S)-1-Cyclohexyl-2-((S)-2-{6-[(2-fluoro-phenyl)-methyl-amino]-pyridin-2-yl}-pyrrolidin-1-yl)-2-oxo-ethylcarbamoyl]-ethyl}-methyl-carbamic acid tert-butyl este (300 mg, 79.5%) as pale gum. M/Z=596.2[M+1]

(S)—N—[(S)-1-Cyclohexyl-2-((S)-2-{6-[(2-fluoro-phenyl)-methyl-amino]-pyridin-2-yl}-pyrrolidin-1-yl)-2-oxo-ethyl]-2-methylamino-propionamide (78)

To a solution of give {(S)-1-[(S)-1-Cyclohexyl-2-((S)-2-{6-[(2-fluoro-phenyl)-methyl-amino]-pyridin-2-yl}-pyrrolidin-1-yl)-2-oxo-ethylcarbamoyl]-ethyl}-methyl-carbamic acid tert-butyl este (300 mg, 0.50 mmol) in CH$_2$Cl$_2$ (1 mL) at −20° C. is added TFA (5 ML, pre-cooled to −20° C.) slowly. After stirring at 0° C. for 30 min, the reaction mixture is concentrated and purified by prep HPLC (Column: Waters Sunfire prep C18 30×100 mm; Mobile phase: isocratic condition, CH$_3$CN 28%/H$_2$O 72% with 0.1% TFA; Flow rate: 45 mL/min) to give (S)—N—[(S)-1-Cyclohexyl-2-((S)-2-{6-[(2-fluoro-phenyl)-methyl-amino]-pyridin-2-yl}-pyrrolidin-1-yl)-2-oxo-ethyl]-2-methylamino-propionamide (206 mg, 67.0%) as white solid TFA salt. (HR Mass M/Z=496.3069 [M+1]).

In order to measure the ability of the inventive compounds to bind the BIR3 peptide binding pocket an ELISA and a cell based assays are utilized.

Elisa

Compounds are incubated with GST-BIR3 fusion protein and biotinylated SMAC peptide (AVPFAQK) in streptavidin-coated 96 well plates. For XIAP BIR3Smac Elisa, a GST-BIR3 fusion containing amino acids 248-358 from XIAP is used. For CIAP1 BIR3Smac Elisa, a GST-BIR3 fusion containing amino acids 259-364 from CIAP1 is used. Following a 30 minute incubation, wells are extensively washed. The remaining GST-BIR3 fusion protein is monitored by ELISA assay involving first, incubation with goat anti-GST antibodies followed by washing and incubation with alkaline phosphatase conjugated anti-goat antibodies. Signal is amplified using Attophos (Promega) and read with Cytoflour Ex 450 nm/40 and Em 580 nm. IC$_{50}$s correspond to concentration of compound which displaces half of GST-BIR3 signal. The IC$_{50}$ for non-biotinylated Smac is 400 nM. The IC$_{50}$ values of compounds listed in Table 1 in the described ELISA assays ranged from 0.005-10 µM.

Cell Proliferation Assay

The ability of compounds to inhibit tumor cell growth in vitro is monitored using the CellTiter 96® AQ$_{ueous}$ Non-Radioactive Cell Proliferation Assay (Promega). This assay is composed of solutions of a novel tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS. MTS is bioreduced by cells into a formazan product, the absorbance of which is measured at 490 nm. The conversion of MTS into the aqueous soluble formazan product is accomplished by dehydrogenase enzymes found in metabolically active cells. The quantity of formazan product as measured by the amount of 490 nm absorbance is directly proportional to the number of living cells in culture. The IC$_{50}$ values of compounds listed in Table 1 in the described cell assays ranged from 0.005-50 µM.

Example 196

Tablets 1 Comprising Compounds of the Formula (I)

Tablets, comprising, as active ingredient, 50 mg of any one of the compounds of formula (I) mentioned in the preceding Examples 9-194 of the following composition are prepared using routine methods:

| Composition: | |
|---|---|
| Active Ingredient | 50 mg |
| Wheat starch | 60 mg |
| Lactose | 50 mg |
| Colloidal silica | 5 mg |
| Talcum | 9 mg |
| Magnesium stearate | 1 mg |
| Total | 175 mg |

Manufacture: The active ingredient is combined with part of the wheat starch, the lactose and the colloidal silica and the mixture pressed through a sieve. A further part of the wheat starch is mixed with the 5-fold amount of water on a water bath to form a paste and the mixture made first is kneaded with this paste until a weakly plastic mass is formed.

The dry granules are pressed through a sieve having a mesh size of 3 mm, mixed with a pre-sieved mixture (1 mm sieve) of the remaining corn starch, magnesium stearate and talcum and compressed to form slightly biconvex tablets.

Example 197

Tablets 2 Comprising Compounds of the Formula (I)

Tablets, comprising, as active ingredient, 100 mg of any one of the compounds of formula (I) of Examples 9-194 are prepared with the following composition, following standard procedures:

| Composition: | |
|---|---|
| Active Ingredient | 100 mg |
| Crystalline lactose | 240 mg |
| Avicel | 80 mg |
| PVPPXL | 20 mg |
| Aerosil | 2 mg |
| Magnesium stearate | 5 mg |
| Total | 447 mg |

Manufacture: The active ingredient is mixed with the carrier materials and compressed by means of a tabletting machine (Korsch EKO, Stempeldurchmesser 10 mm).

Example 198

Capsules

Capsules, comprising, as active ingredient, 100 mg of any one of the compounds of formula (I) given in Examples 9-194, of the following composition are prepared according to standard procedures:

| Composition: | |
|---|---|
| Active Ingredient | 100 mg |
| Avicel | 200 mg |
| PVPPXL | 15 mg |
| Aerosil | 2 mg |
| Magnesium stearate | 1.5 mg |
| Total | 318.5 mg |

Manufacturing is done by mixing the components and filling them into hard gelatine capsules, size 1.

We claim:

1. A compound of formula (IV)

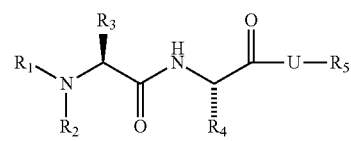

IV wherein
  $R_1$ and $R_3$ are each independently methyl or ethyl;
  $R_2$ is H, methyl, ethyl, chloromethyl, dichloromethyl or trifluoromethyl;
  $R_4$ is $C_1$-$C_4$alkyl or $C_3$-$C_7$ cycloalkyl;
  $R_5$ is H;
  U is a structure of formula (II)

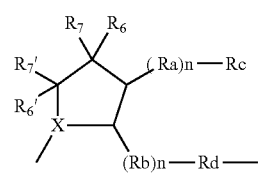

II where
  (a) X is N;
    $R_6$, $R_6'$, $R_7$ and $R_7'$ are H;
    Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$, where $Ar_1$ and $Ar_2$ are each independently a substituted or unsubstituted phenyl or het, and D is $C_1$ alkyl which is optionally substituted with halo, where the phenyl or the het of $Ar_1$ is attached to both (Rb)n and D, and the phenyl or the het of $Ar_2$ is attached to both D and $R^5$;

(b) X is N;

$R_6$, $R'_6$, $R_7$, and $R'_7$ are H; or $R_6$ is —C(O)—$C_1$-$C_4$alkyl-phenyl and $R'_6$, $R_7$, and $R'_7$ are H;

Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$, wherein $Ar_1$ and $Ar_2$ are each independently a substituted or unsubstituted phenyl or het, and D is N(Rh), where Rh is H, Me, —CHO, —$SO_2$, —C(O), —CHOH, —$CF_3$ or —$SO_2CH_3$, where the phenyl or the het of $Ar_1$ is attached to both (Rb)n and D, and the phenyl or the het of $Ar_2$ is attached to both D and $R^5$;

(c) X is N;

$R_6$, $R'_6$, $R_7$, and $R'_7$ are H;

Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$, where $Ar_1$ and $Ar_2$ are each independently a substituted or unsubstituted phenyl or het, and D is —O—, where the phenyl or the het of $Ar_1$ is attached to both (Rb)n and D, and the phenyl or the het of $Ar_2$ is attached to both D and $R^5$; or (d) X is N;

$R_6$, $R'_6$, $R_7$, and $R'_7$ are H;

Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$, where $Ar_1$ and $Ar_2$ are each independently a substituted or unsubstituted phenyl or het, and D is S, S(O), or $S(O)_2$, where the phenyl or the het of $Ar_1$ is attached to both (Rb)n and D, and the phenyl or the het of $Ar_2$ is attached to both D and $R^5$;

(e) X is N;

$R_6$, $R'_6$, $R_7$, and $R'_7$ are H;

Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$;

$Ar_1$ and $Ar_2$ are each independently a substituted or unsubstituted phenyl or het, and D is C(O), where the phenyl or the het of $Ar_1$ is attached to both (Rb)n and D, and the phenyl or the het of $Ar_2$ is attached to both D and $R^5$;

or a pharmaceutically acceptable salt thereof.

2. The compound of claim 1 wherein U has a structure of formula V

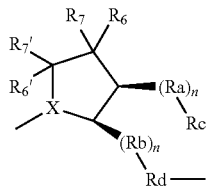

or a pharmaceutically acceptable salt thereof.

3. The compound of claim 2 wherein (a) X is N;

$R_6$, $R_6'$, $R_7$ and $R_7'$ are H;

Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$, where $Ar_1$ and $Ar_2$ are each independently a substituted or unsubstituted phenyl or het, where the het is selected from the group consisting of tetrazolyl, 1,2,3-triazole, pyrazole, oxazole, pyrrolyl, triazine, pyrimidine, imidazole, and oxadiazole, and D is $C_1$ alkyl which is optionally substituted with halo, wherein the phenyl or the het of $Ar_1$ is attached to both (Rb)n and D, and the phenyl or the het of $Ar_2$ is attached to both D and $R^5$;

or a pharmaceutically acceptable salt thereof.

4. The compound of claim 3 selected from the group consisting of

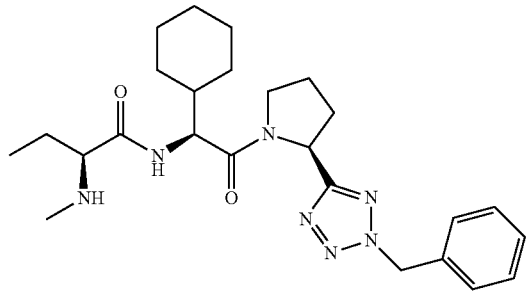

N-[(1S)-1-cyclohexyl-2-oxo-2-[(2S)-2-[2-(phenylmethyl)-2H-tetrazol-5-yl]-1-pyrrolidinyl]ethyl]-2-(methylamino)-(2S)-butanamide;

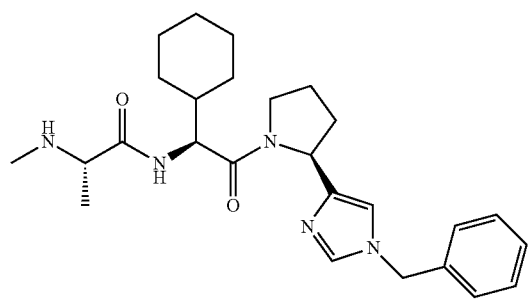

N-[(1S)-1-cyclohexyl-2-oxo-2-[(2S)-2-[1-(phenylmethyl)-1H-imidazol-4-yl]-1-pyrrolidinyl]ethyl]-2-(methylamino)-(2S)-propanamide;

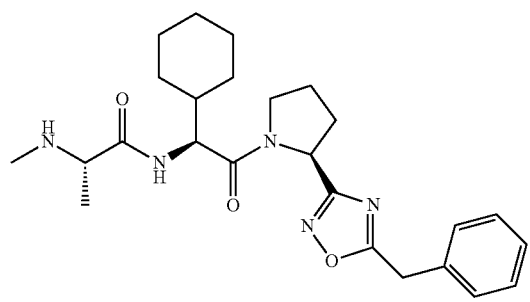

N-[(1S)-1-cyclohexyl-2-oxo-2-[(2S)-2-[5-(phenylmethyl)-1,2,4-oxadiazol-3-yl]-1-pyrrolidinyl]ethyl]-2-(methylamino)-(2S)-propanamide;

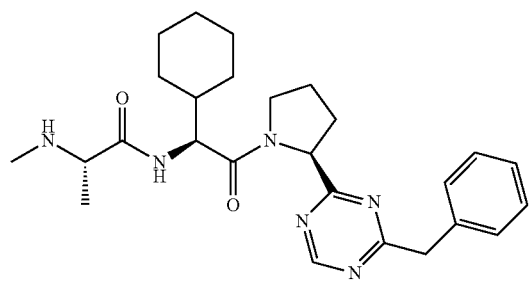

N-[(1S)-1-cyclohexyl-2-oxo-2-[(2S)-2-[4-(phenylmethyl)-1,3,5-triazin-2-yl]-1-pyrrolidinyl]ethyl]-2-(methylamino)-(2S)-propanamide;

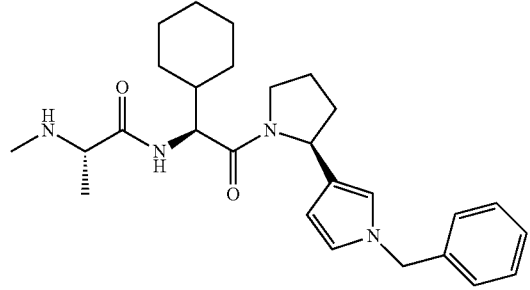

N-[(1S)-1-cyclohexyl-2-oxo-2-[(2S)-2-[1-(phenylmethyl)-1H-pyrrol-3-yl]-1-pyrrolidinyl]ethyl]-2-(methylamino)-(2S)-propanamide;

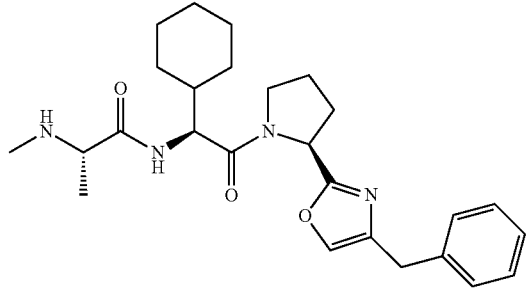

N-[(1S)-1-cyclohexyl-2-oxo-2-[(2S)-2-[4-(phenylmethyl)-2-oxazolyl]-1-pyrrolidinyl]ethyl]-2-(methylamino)-(2S)-propanamide;

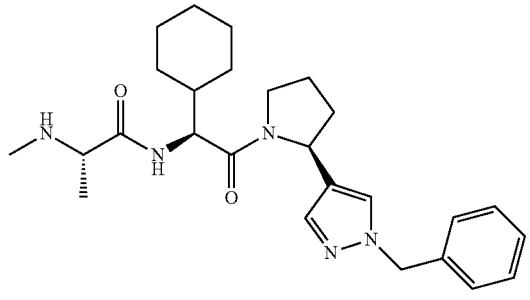

N-[(1S)-1-cyclohexyl-2-oxo-2-[(2S)-2-[1-(phenylmethyl)-1H-pyrazol-4-yl]-1-pyrrolidinyl]ethyl]-2-(methylamino)-(2S)-propanamide;

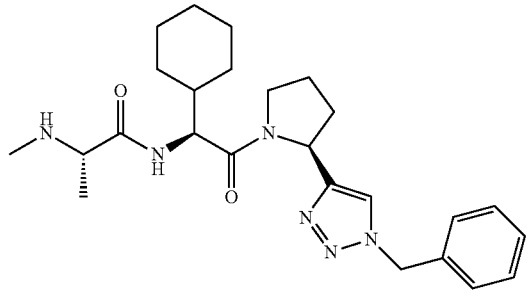

N-[(1S)-1-cyclohexyl-2-oxo-2-[(2S)-2-[1-(phenylmethyl)-1H-1,2,3-triazol-4-yl]-1-pyrrolidinyl]ethyl]-2-(methylamino)-(2S)-propanamide;

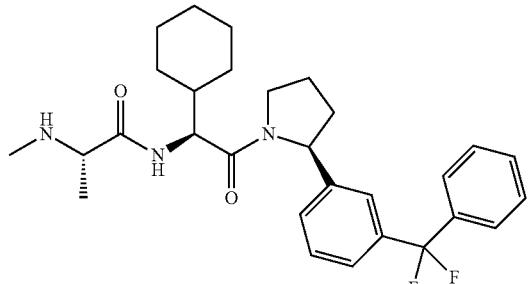

N-[(1S)-1-cyclohexyl-2-[(2S)-2-[3-(difluorophenylmethyl)phenyl]-1-pyrrolidinyl]-2-oxoethyl]-2-(methylamino)-(2S)-propanamide;

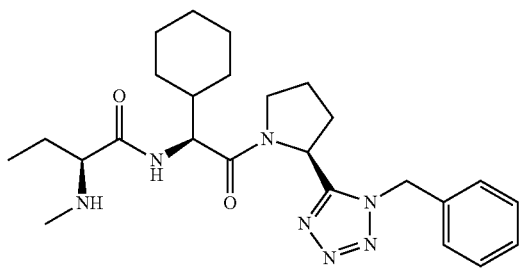

N-[(1S)-1-cyclohexyl-2-oxo-2-[(2S)-2-[1-(phenylmethyl)-1H-tetrazol-5-yl]-1-pyrrolidinyl]ethyl]-2-(methylamino)-(2S)-butanamide;

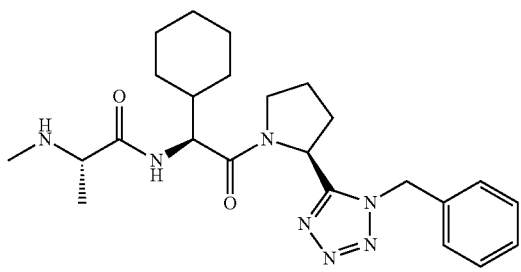

N-[(1S)-1-cyclohexyl-2-oxo-2-[(2S)-2-[1-(phenylmethyl)-1H-tetrazol-5-yl]-1-pyrrolidinyl]ethyl]-2-(methylamino)-(2S)-propanamide;

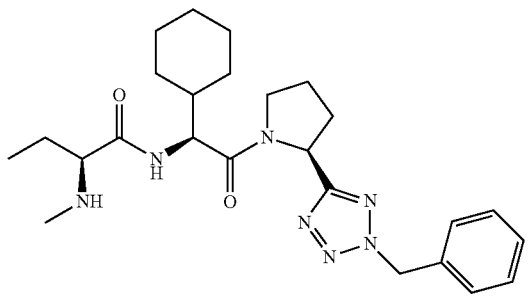

N-[(1S)-1-cyclohexyl-2-oxo-2-[(2S)-2-[2-(phenylmethyl)-2H-tetrazol-5-yl]-1-pyrrolidinyl]ethyl]-2-(methylamino)-(2S)-butanamide;

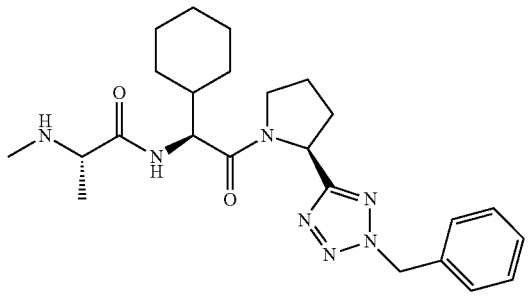

N-[(1S)-1-cyclohexyl-2-oxo-2-[(2S)-2-[2-(phenylmethyl)-2H-tetrazol-5-yl]-1-pyrrolidinyl]ethyl]-2-(methylamino)-(2S)-propanamide; and

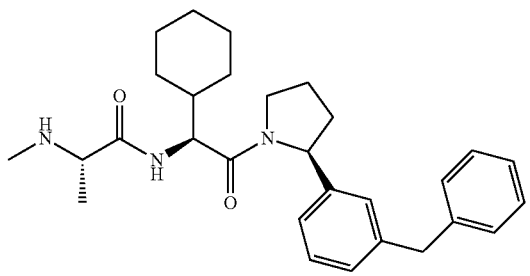

N-[(1S)-1-cyclohexyl-2-oxo-2-[(2S)-2-[3-(phenylmethyl)phenyl]-1-pyrrolidinyl]ethyl]-2-(methylamino)-(2S)-propanamide;

or a pharmaceutically acceptable salt thereof.

5. The compound of claim 2 wherein (b) X is N;

$R_6$, $R_6'$, $R_7$ and $R_7'$ are H; or $R_6$ is —C(O)—$C_1$-$C_4$alkyl-phenyl and $R_6'$, $R_7$ and $R_7'$ are H;

Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;

Rc is H;

Rd is $Ar_1$-D-$Ar_2$, wherein $Ar_1$ and $Ar_2$ are each independently a substituted or unsubstituted phenyl or het selected from the group consisting of triazine, pyrimidine, pyridine, and oxazole, and D is N(Rh), where Rh is H, Me, —CHO, —$SO_2$, —$CH_2OH$, —$CF_3$ or —$SO_2CH_3$, and where the phenyl or the het of $Ar_1$ is attached to both (Rb)n and D, and the phenyl or the het of $Ar_2$ is attached to both D and $R^5$;

or a pharmaceutically acceptable salt thereof.

6. The compound of claim 5 selected from the group consisting of

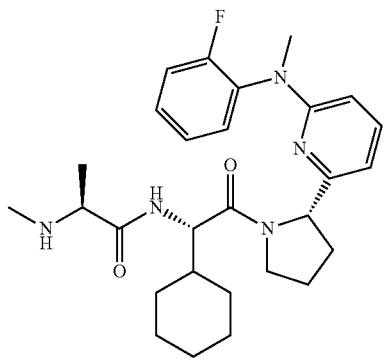

N-[(1S)-1-cyclohexyl-2-[(2S)-2-[6-[(2-fluorophenyl)methylamino]-2-pyridinyl]-1-pyrrolidinyl]-2-oxoethyl]-2-(methylamino)-(2S)-propanamide;

145

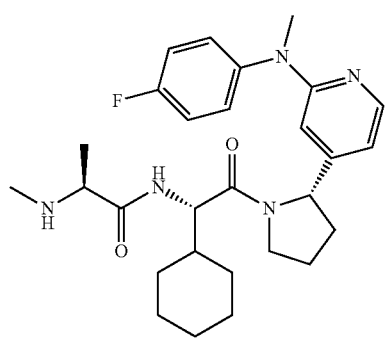

N-[(1S)-1-cyclohexyl-2-[(2S)-2-[2-[(4-fluorophenyl)methylamino]-4-pyridinyl]-1-pyrrolidinyl]-2-oxoethyl]-2-(methylamino)-(2S)-propanamide;

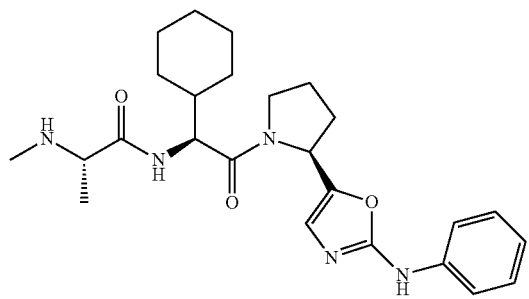

N-[(1S)-1-cyclohexyl-2-oxo-2-[(2S)-2-[2-(phenylamino)-5-oxazolyl]-1-pyrrolidinyl]ethyl]-2-(methylamino)-(2S)-propanamide;

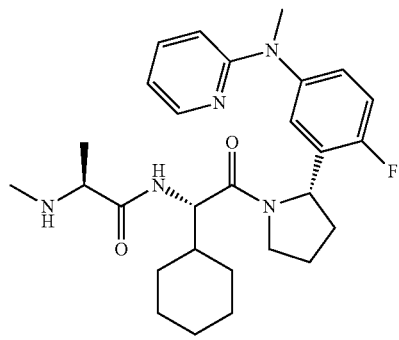

N-[(1S)-1-cyclohexyl-2-[(2S)-2-[2-fluoro-5-(methyl-2-pyridinylamino)phenyl]-1-pyrrolidinyl]-2-oxoethyl]-2-(methylamino)-(2S)-propanamide;

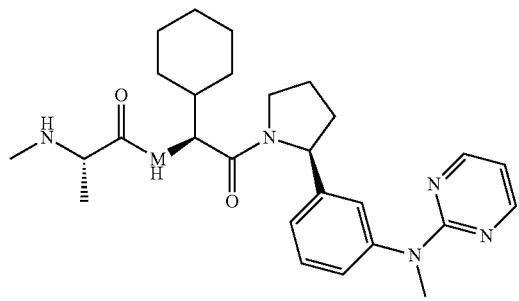

N-[(1S)-1-cyclohexyl-2-[(2S)-2-[3-(methyl-2-pyrimidinylamino)phenyl]-1-pyrrolidinyl]-2-oxoethyl]-2-(methylamino)-(2S)-propanamide;

146

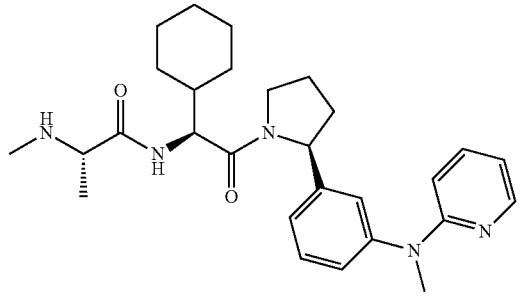

N-[(1S)-1-cyclohexyl-2-[(2S)-2-[3-(methyl-2-pyridinylamino)phenyl]-1-pyrrolidinyl]-2-oxoethyl]-2-(methylamino)-(2S)-propanamide;

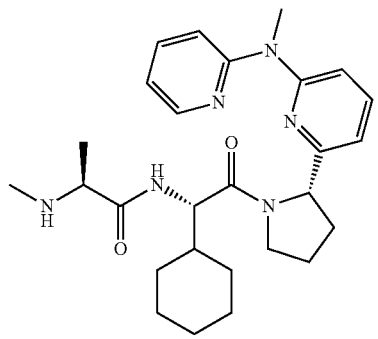

N-[(1S)-1-cyclohexyl-2-[(2S)-2-[6-(methyl-2-pyridinylamino)-2-pyridinyl]-1-pyrrolidinyl]-2-oxoethyl]-2-(methylamino)-(2S)-propanamide;

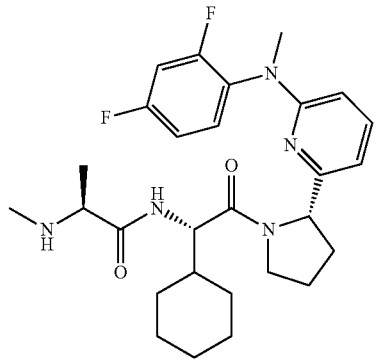

N-[(1S)-1-cyclohexyl-2-[(2S)-2-[6-[(2,4-difluorophenyl)methylamino]-2-pyridinyl]-1-pyrrolidinyl]-2-oxoethyl]-2-(methylamino)-(2S)-propanamide;

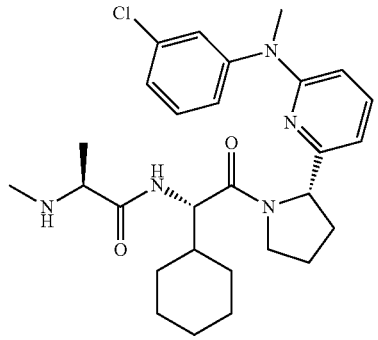

N-[(1S)-2-[(2S)-2-[6-[(3-chlorophenyl)methylamino]-2-pyridinyl]-1-pyrrolidinyl]-1-cyclohexyl-2-oxoethyl]-2-(methylamino)-(2S)-propanamide;

147

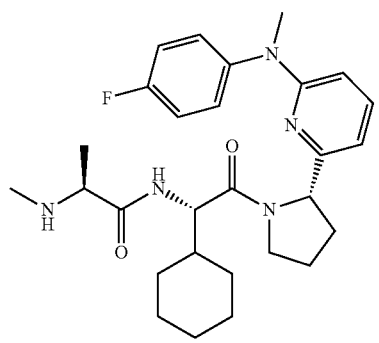

N-[(1S)-1-cyclohexyl-2-[(2S)-2-[6-[(4-fluorophenyl)methylamino]-2-pyridinyl]-1-pyrrolidinyl]-2-oxoethyl]-2-(methylamino)-(2S)-propanamide;

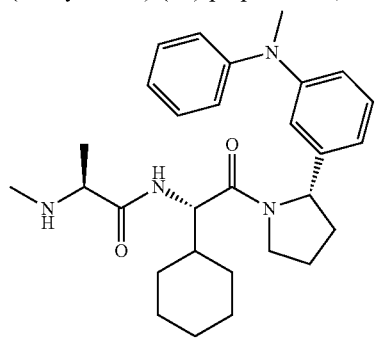

N-[(1S)-1-cyclohexyl-2-[(2S)-2-[6-(methylphenylamino)-2-pyridinyl]-1-pyrrolidinyl]-2 oxoethyl]-2-(methylamino)-(2S)-propanamide;

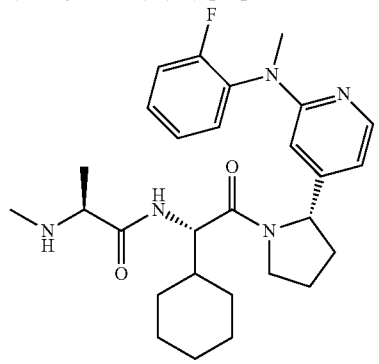

N-[(1S)-1-cyclohexyl-2-[(2S)-2-[2-[(2-fluorophenyl)methylamino]-4-pyridinyl]-1-pyrrolidinyl]-2-oxoethyl]-2-(methylamino)-(2S)-propanamide;

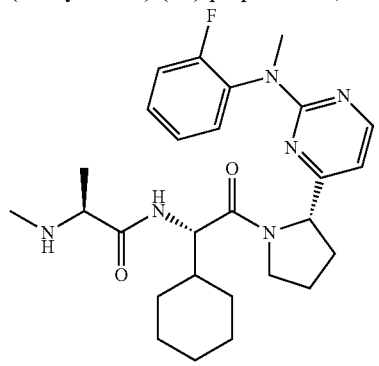

N-[(1S)-1-cyclohexyl-2-[(2S)-2-[2-[(2-fluorophenyl)methylamino]-4-pyrimidinyl]-1-pyrrolidinyl]-2-oxoethyl]-2-(methylamino) (2S)-propanamide;

148

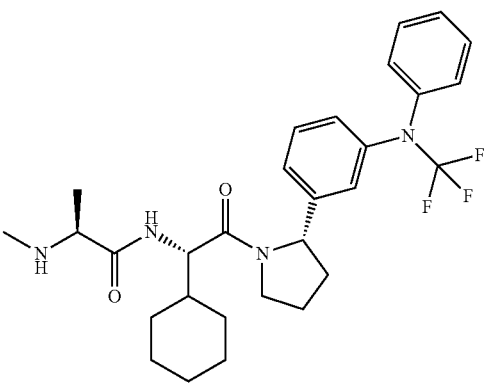

N-[(1S)-1-cyclohexyl-2-oxo-2-[(2S)-2-[3-[phenyl(trifluoromethyl)amino]phenyl]-1-pyrrolidinyl]ethyl]-2-(methylamino)-(2S)-propanamide;

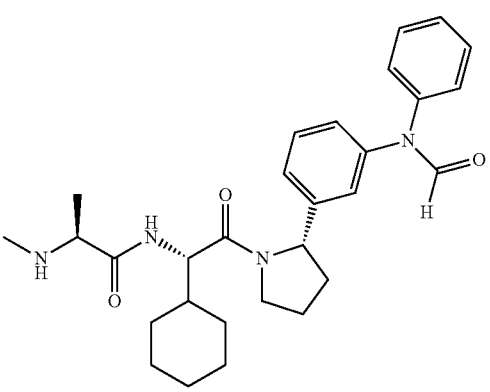

N-[(1S)-1-cyclohexyl-2-[(2S)-2-[3-(formylphenylamino)phenyl]-1-pyrrolidinyl]-2-oxoethyl]-2-(methylamino)-(2S)-propanamide;

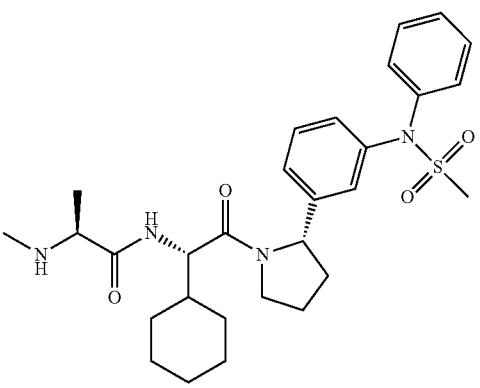

N-[(1S)-1-cyclohexyl-2-[(2S)-2-[3-[(methylsulfonyl)phenylamino]phenyl]-1-pyrrolidinyl]-2-oxoethyl]-2-(methylamino)-(2S)-propanamide;

149

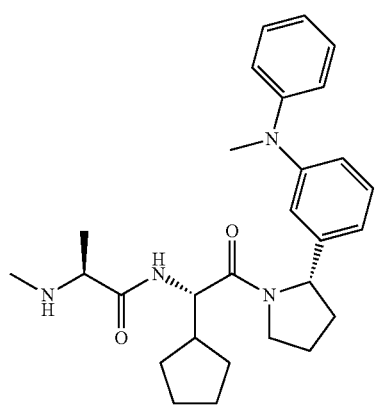

N-[(1S)-1-cyclopentyl-2-[(2S)-2-[3-(methylphenylamino)phenyl]-1-pyrrolidinyl]-2-oxoethyl]-2-(methylamino)-(2S)-propanamide;

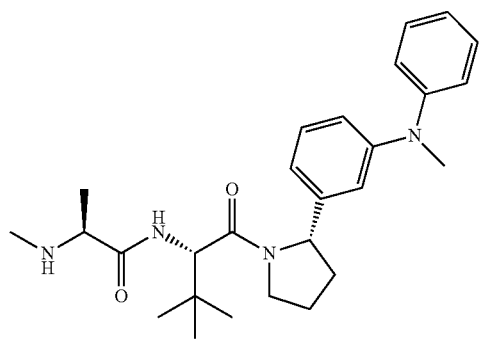

N-[(1S)-2,2-dimethyl-1-[[(2S)-2-[3-(methylphenylamino)phenyl]-1-pyrrolidinyl]carbonyl]propyl]-2-(methylamino)-(2S)-propanamide;

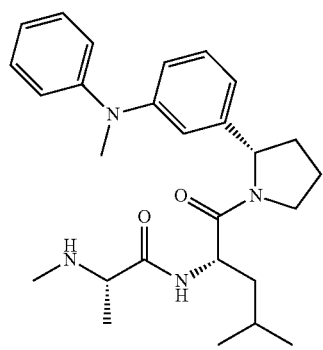

2-(methylamino)-N-[(1S)-3-methyl-1-[[(2S)-2-[3-(methylphenylamino)phenyl]-1-pyrrolidinyl]carbonyl]butyl]-(2S)-propanamide,

150

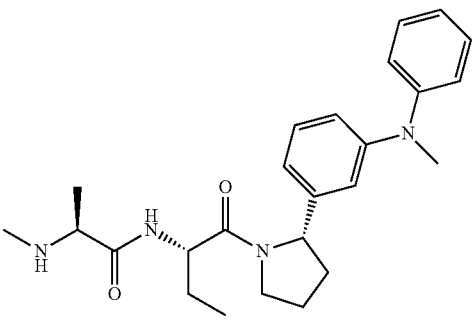

2-(methylamino)-N-[(1S)-1-[[(2S)-2-[3-(methylphenylamino)phenyl]-1-pyrrolidinyl]carbonyl]propyl]-(2S)-propanamide;

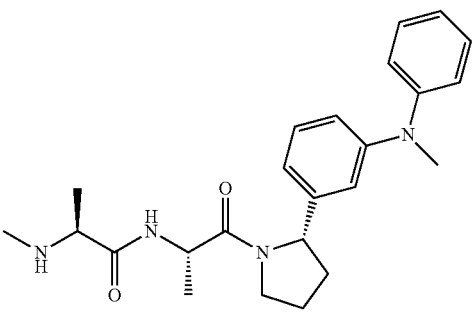

2-(methylamino)-N-[(1S)-1-methyl-2-[(2S)-2-[3-(methylphenylamino)phenyl]-1-pyrrolidinyl]-2-oxoethyl]-(2S)-propanamide;

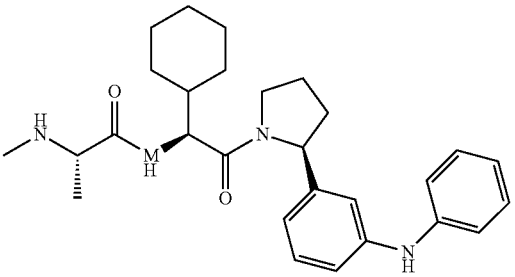

N-[(1S)-1-cyclohexyl-2-oxo-2-[(2S)-2-[3-(phenylamino)phenyl]-1-pyrrolidinyl]ethyl]-2-(methylamino)-(2S)-propanamide;

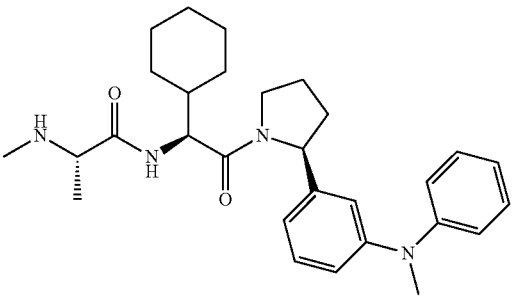

N-[(1S)-1-cyclohexyl-2-[(2S)-2-[3-(methylphenylamino)phenyl]-1-pyrrolidinyl]-2-oxoethyl]-2-(methylamino)-(2S)-propanamide; and

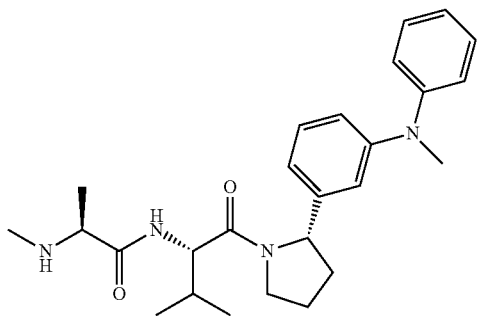

2-(methylamino)-N-[(1S)-2-methyl-1-[[(2S)-2-[3-(methylphenylamino)phenyl]-1-pyrrolidinyl]carbonyl]propyl]-(2S)-propanamide;

or a pharmaceutically acceptable salt thereof.

7. The compound of claim 2 wherein
(c) X is N;
$R_6$, $R_6'$, $R_7$ and $R_7'$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;
n is 0;
Rc is H;
Rd is $Ar_1$-D-$Ar_2$, where $Ar_1$ and $Ar_2$ are each independently a substituted or unsubstituted phenyl or het selected from the group consisting of pyrimidine, pyridine, oxazole, and 2-methyloxazole, and D is —O—, where the phenyl or the het of $Ar_1$ is attached to both (Rb)n and D, and the phenyl or the het of $Ar_2$ is attached to both D and $R^5$;

or a pharmaceutically acceptable salt thereof.

8. The compound of claim 7 selected from the group consisting of

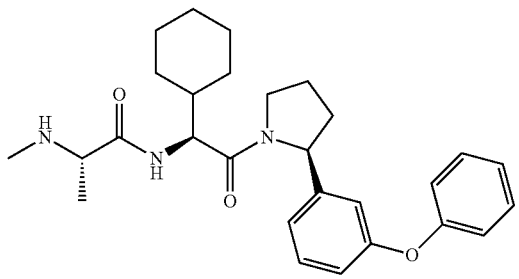

N-[(1S)-1-cyclohexyl-2-oxo-2-[(2S)-2-(3-phenoxyphenyl)-1-pyrrolidinyl]ethyl]-2-(methylamino)-(2S)-propanamide;

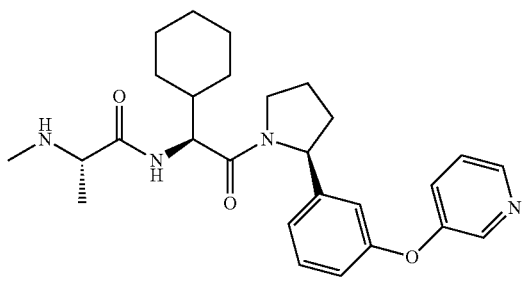

N-[(1S)-1-cyclohexyl-2-oxo-2-[(2S)-2-[3-(3-pyridinyloxy)phenyl]-1-pyrrolidinyl]ethyl]-2-(methylamino)-(2S)-propanamide;

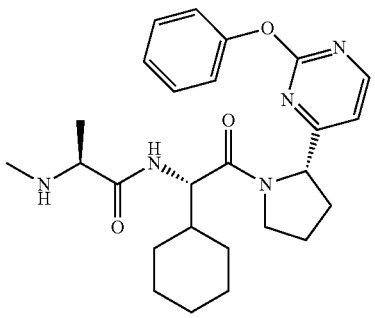

N-[(1S)-1-cyclohexyl-2-oxo-2-[(2S)-2-(2-phenoxy-4-pyrimidinyl)-1-pyrrolidinyl]ethyl]-2-(methylamino)-(2S)-propanamide;

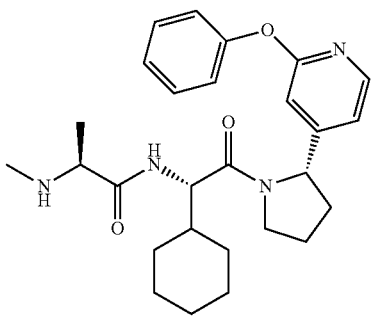

N-[(1S)-1-cyclohexyl-2-oxo-2-[(2S)-2-(2-phenoxy-4-pyridinyl)-1-pyrrolidinyl]ethyl]-2-(methylamino)-(2S)-propanamide;

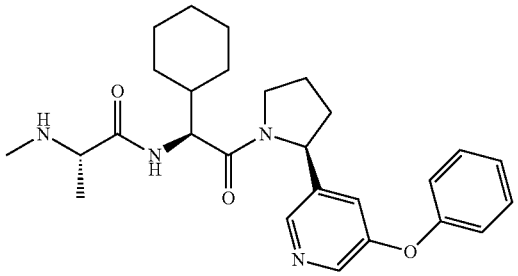

N-[(1S)-1-cyclohexyl-2-oxo-2-[(2S)-2-(5-phenoxy-3-pyridinyl)-1-pyrrolidinyl]ethyl]-2-(methylamino)-(2S)-propanamide;

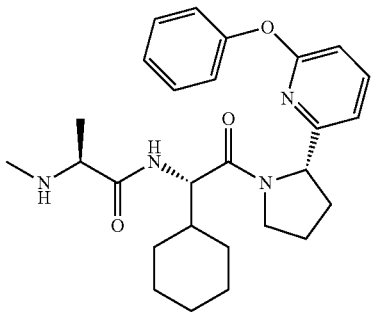

N-[(1S)-1-cyclohexyl-2-oxo-2-[(2S)-2-(6-phenoxy-2-pyridinyl)-1-pyrrolidinyl]ethyl]-2-(methylamino)-(2S)-propanamide;

153

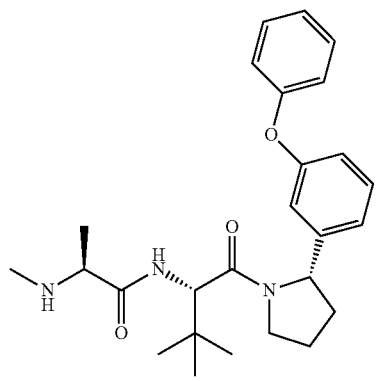

N-[(1S)-2,2-dimethyl-1-[[(2S)-2-(3-phenoxyphenyl)-1-pyrrolidinyl]carbonyl]propyl]-2-(methylamino)-(2S)-propanamide;

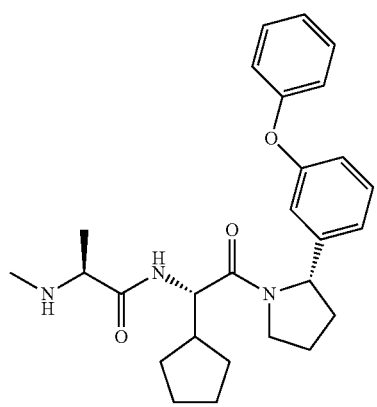

N-[(1S)-1-cyclopentyl-2-oxo-2-[(2S)-2-(3-phenoxyphenyl)-1-pyrrolidinyl]ethyl]-2-(methylamino)-(2S)-propanamide;

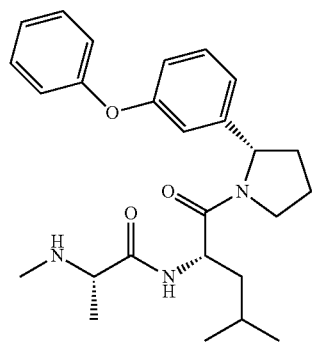

2-(methylamino)-N-[(1S)-3-methyl-1-[[(2S)-2-(3-phenoxyphenyl)-1-pyrrolidinyl]carbonyl]butyl]-(2S)-propanamide;

154

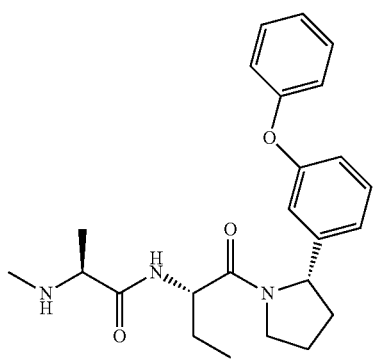

2-(methylamino)-N-[(1S)-1-[[(2S)-2-(3-phenoxyphenyl)-1-pyrrolidinyl]carbonyl]propyl]-(2S)-propanamide;

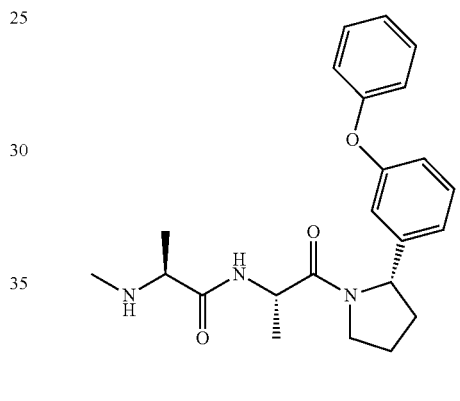

2-(methylamino)-N-[(1S)-1-methyl-2-oxo-2-[(2S)-2-(3-phenoxyphenyl)-1-pyrrolidinyl]ethyl]-(2S)-propanamide;

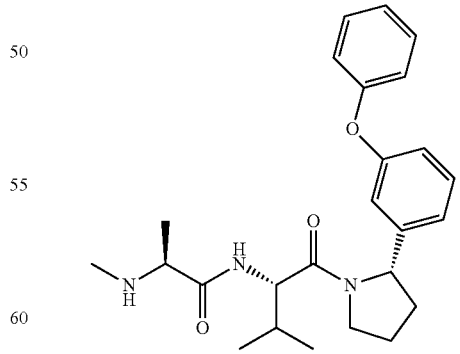

2-(methylamino)-N-[(1S)-2-methyl-1-[[(2S)-2-(3-phenoxyphenyl)-1-pyrrolidinyl]carbonyl]propyl]-(2S)-propanamide;

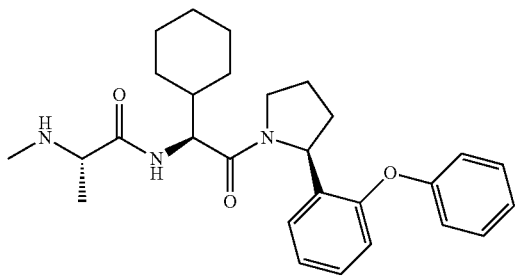

N-[(1S)-1-cyclohexyl-2-oxo-2-[(2S)-2-(2-phenoxyphenyl)-1-pyrrolidinyl]ethyl]-2-(methylamino)-(2S)-propanamide;

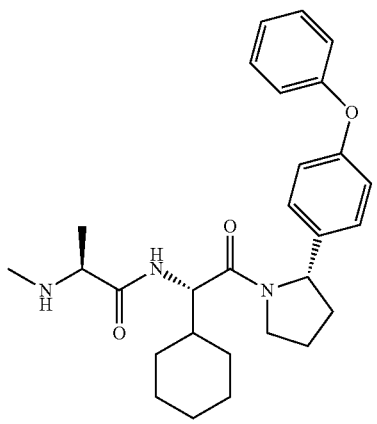

N-[(1S)-1-cyclohexyl-2-oxo-2-[(2S)-2-(4-phenoxyphenyl)-1-pyrrolidinyl]ethyl]-2-(methylamino)-(2S)-propanamide; and

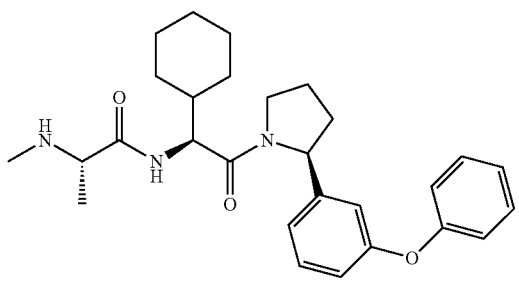

N-[(1S)-1-cyclohexyl-2-oxo-2-[(2S)-2-(3-phenoxyphenyl)-1-pyrrolidinyl]ethyl]-2-(methylamino)-(2S)-propanamide;

or a pharmaceutically acceptable salt thereof.

9. The compound of claim 2 wherein
(d) X is N;
$R_6$, $R_6'$, $R_7$ and $R_7'$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;
n is 0;
Rc is H;
Rd is $Ar_1$-D-$Ar_2$, where $Ar_1$ and $Ar_2$ are each independently a substituted or unsubstituted phenyl or het, and D is S, S(O), or S(O)$_2$, where the phenyl or the het of $Ar_1$ is attached to both (Rb)n and D, and the phenyl or the het of $Ar_2$ is attached to both D and $R^5$;
or a pharmaceutically acceptable salt thereof.

10. The compound of claim 9 selected from the group consisting of

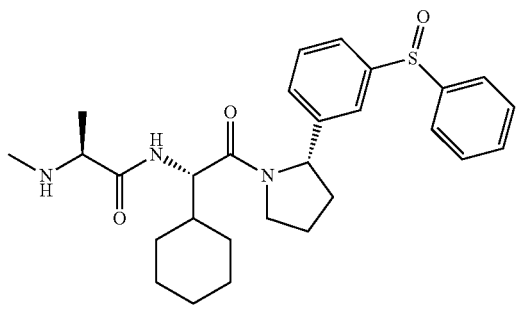

N-[(1S)-1-cyclohexyl-2-oxo-2-[(2S)-2-[3-(phenylsulfinyl)phenyl]-1-pyrrolidinyl]ethyl]-2-(methylamino)-(2S)-propanamide;

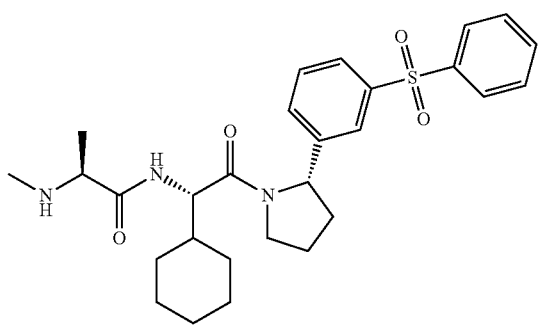

N-[(1S)-1-cyclohexyl-2-oxo-2-[(2S)-2-[3-(phenylsulfonyl)phenyl]-1-pyrrolidinyl]ethyl]-2-(methylamino)-(2S)-propanamide; and

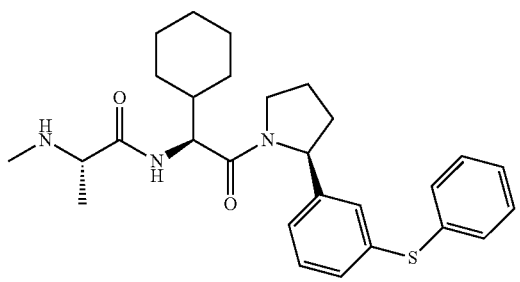

N-[(1S)-1-cyclohexyl-2-oxo-2-[(2S)-2-[3-(phenylthio)phenyl]-1-pyrrolidinyl]ethyl]-2-(methylamino)-(2S)-propanamide;

or a pharmaceutically acceptable salt thereof.

11. The compound of claim 2 wherein
(e) X is N;
$R_6$, $R_6'$, $R_7$ and $R_7'$ are H;
Ra and Rb are independently an O, S, or N atom or $C_{0-8}$ alkyl wherein one or more of the carbon atoms in the alkyl chain may be replaced by a heteroatom selected from O, S or N, and where the alkyl is unsubstituted or substituted;

n is 0;
Rc is H;
Rd is Ar$_1$-D-Ar$_2$;
Ar$_1$ and Ar$_2$ are each independently a substituted or unsubstituted phenyl or het selected from the group consisting of oxazole, thiazole and oxadiazole, and D is C(O), where the phenyl or the het of Ar$_1$ is attached to both (Rb)n and D, and the phenyl or the het of Ar$_2$ is attached to both D and R$^5$;
or a pharmaceutically acceptable salt thereof.

12. The compound of claim 11 selected from the group consisting of

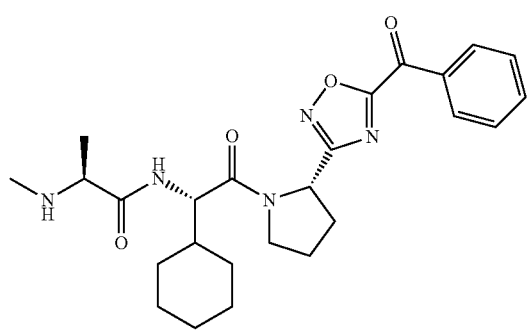

N-[(1S)-2-[(2S)-2-(5-benzoyl-1,2,4-oxadiazol-3-yl)-1-pyrrolidinyl]-1-cyclohexyl-2-oxoethyl]-2-(methylamino)-(2S)-propanamide;

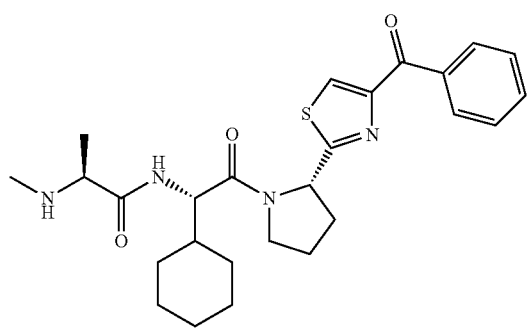

N-[(1S)-2-[(2S)-2-(4-benzoyl-2-thiazolyl)-1-pyrrolidinyl]-1-cyclohexyl-2-oxoethyl]-2-(methylamino)-(2S)-propanamide;

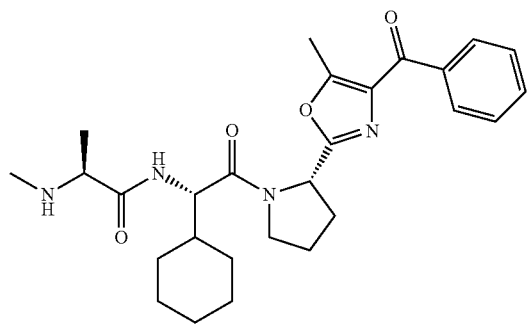

N-[(1S)-2-[(2S)-2-(4-benzoyl-5-methyl-2-oxazolyl)-1-pyrrolidinyl]-1-cyclohexyl-2-oxoethyl]-2-(methylamino)-(2S)-propanamide;

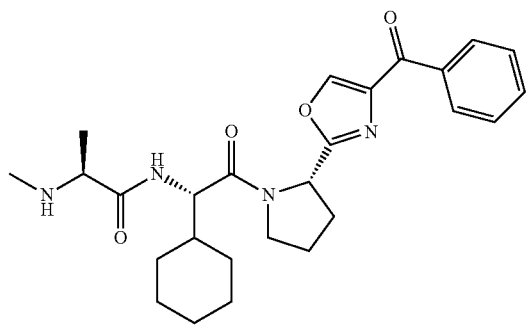

N-[(1S)-2-[(2S)-2-(4-benzoyl-2-oxazolyl)-1-pyrrolidinyl]-1-cyclohexyl-2-oxoethyl]-2-(methylamino)-(2S)-propanamide; and

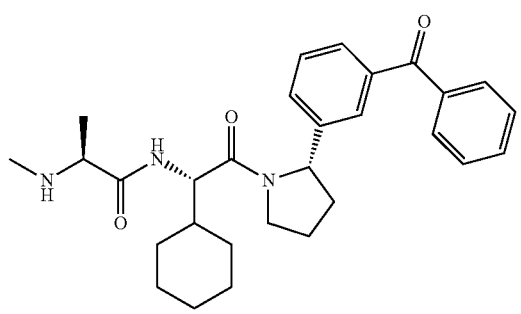

N-[(1S)-2-[(2S)-2-(3-benzoylphenyl)-1-pyrrolidinyl]-1-cyclohexyl-2-oxoethyl]-2-(methylamino)-(2S)-propanamide;

or a pharmaceutically acceptable salt thereof.

13. A pharmaceutical composition which comprises a pharmaceutically acceptable carrier and a therapeutically effective amount of a compound of formula IV according to claim 1.

14. A compound selected from the group consisting of

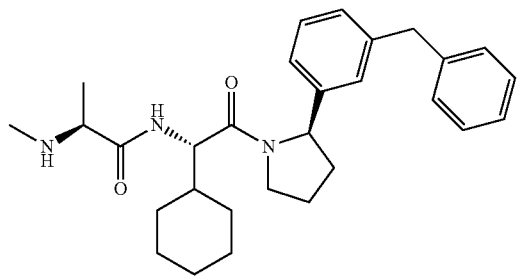

(S)—N-{(S)-2-[(R)-2-(3-Benzyl-phenyl)-pyrrolidin-1-yl]-1-cyclohexyl-2-oxo-ethyl}-2-methylamino-propionamide;

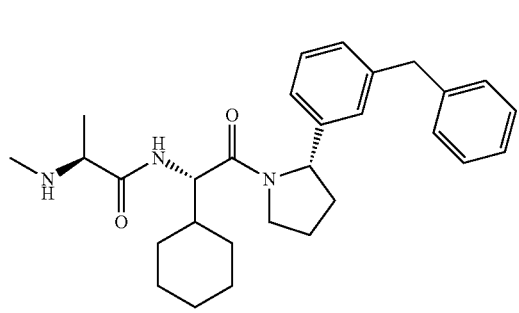

(S)—N-{(S)-2-[(S)-2-(3-Benzyl-phenyl)-pyrrolidin-1-yl]-1-cyclohexyl-2-oxo-ethyl}-2-methylamino-propionamide;

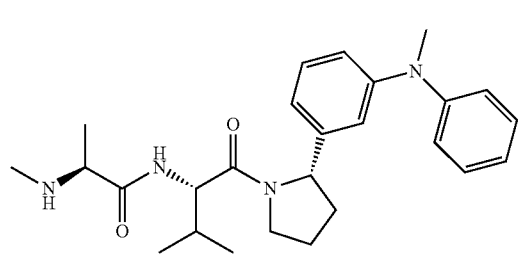

(S)-2-Methylamino-N((S)-2-methyl-1-{(S)-2-[3-(methyl-phenyl-amino)-phenyl]pyrrolidine-1-carbonyl}-propyl)-propionamide;

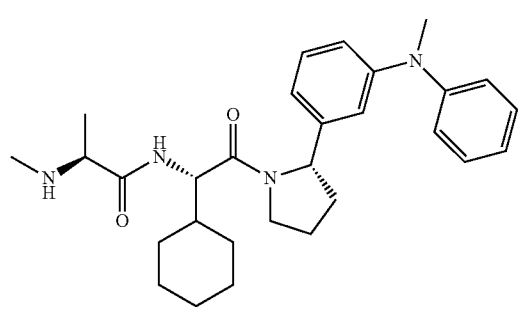

(S)—N—((S)-1-Cyclohexyl-2-{(S)-2-[3-(methyl-phenyl-amino)-phenyly]-pyrrolidin-1-yl}-2-oxo-ethyl)-2-methylamino-propionamide;

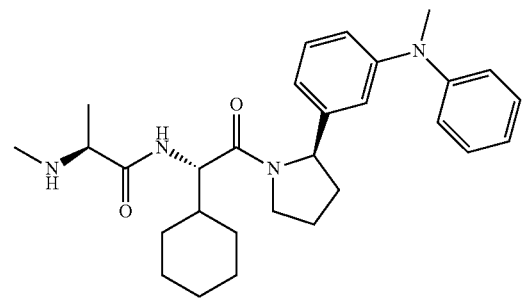

(S)—N—((S)-1-Cyclohexyl-2-{(R)-2-[3-(methyl-phenyl-amino)-phenyl]-pyrrolidin-1-yl}-2-oxo-ethyl)-2-methylamino-propionamide;

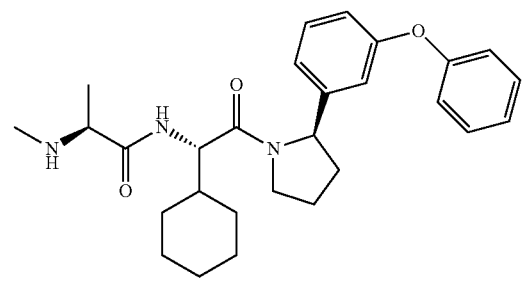

(S)—N-{(S)-1-Cyclohexyl-2-oxo-2-[(R)-2-(3-phenoxy-phenyl)-pyrrolidin-1-yl]-ethyl}-2-methylamino-propionamide;

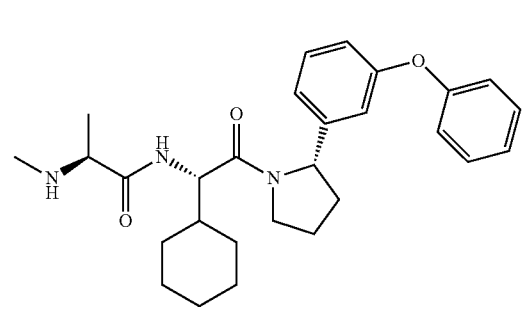

(S)—N-{(S)-1-Cyclohexyl-2-oxo-2-[(S)-2-(3-phenoxy-phenyl)-pyrrolidin-1-yl]-ethyl}-2-methylamino-propionamide;

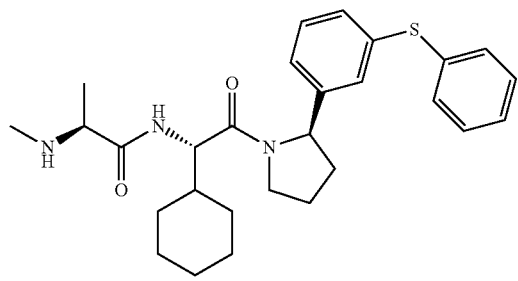

(S)—N-{(S)-1-Cyclohexyl-2-oxo-2-[(R)-2-(3-phenylsul-fanyl-phenyl)-pyrrolidin-1-yl]ethyl}-2-methylamino-propionamide;

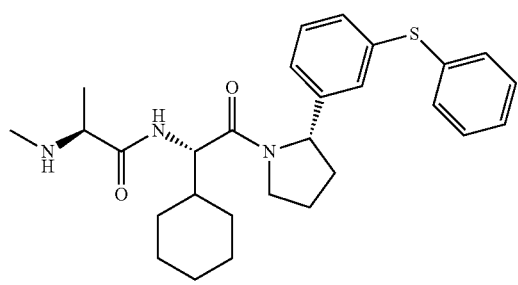

(S)—N-{(S)-1-Cyclohexyl-2-oxo-2-[(S)-2-(3-phenylsul-fanyl-phenyl)-pyrrolidin-1-yl]ethyl}-2-methylamino-propionamide;

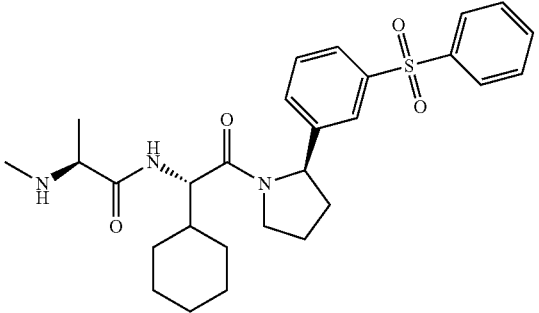

(S)—N-{(S)-2-[(R)-2-(3-Benzenesulfonyl-phenyl)-pyr-rolidin-1-yl]-1-cyclohexyl-2-oxoethyl}-2-methy-lamino-propionamide;

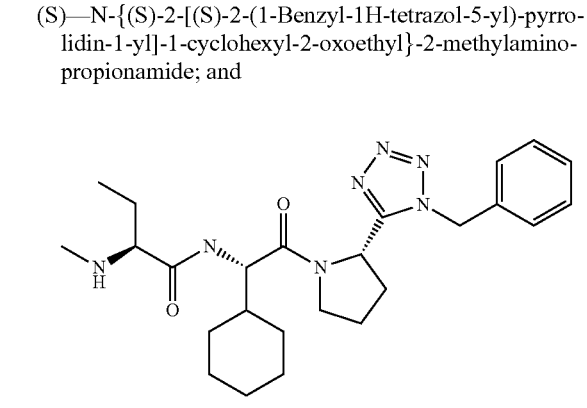

(S)—N-{(S)-2-[(S)-2-(2-Benzyl-2H-tetrazol-5-yl)-pyrro-lidin-1-yl]-1-cyclohexyl-2-oxo-ethyl}-2-methylamino-propionamide;

(S)—N-{(S)-2-[(S)-2-(2-Benzyl-2H-tetrazol-5-yl)-pyrro-lidin-1-yl]-1-cyclohexyl-2-oxoethyl}-2-methylamino-butyramide;

(S)—N-{(S)-2-[(S)-2-(1-Benzyl-1H-tetrazol-5-yl)-pyrro-lidin-1-yl]-1-cyclohexyl-2-oxoethyl}-2-methylamino-propionamide; and (S)—N-{(S)-2-[(S)-2-(1-Benzyl-1H-tetrazol-5-yl)-pyrro-lidin-1-yl]-1-cyclohexyl-2-oxoethyl}-2-methylamino-butyramide;

or a pharmaceutically acceptable salt thereof.

15. A compound selected from the group consisting of

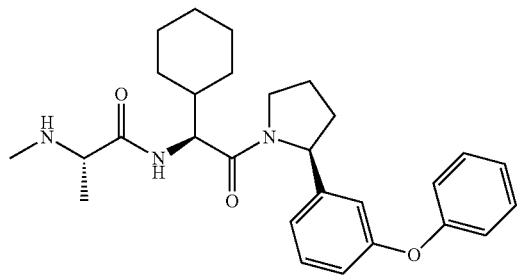

(S)—N-{(S)-1-Cyclohexyl-2-oxo-2-[(S)-2-(3-phenoxy-phenyl)-pyrrolidin-1-yl]-ethyl}-2-methylamino-propionamide;

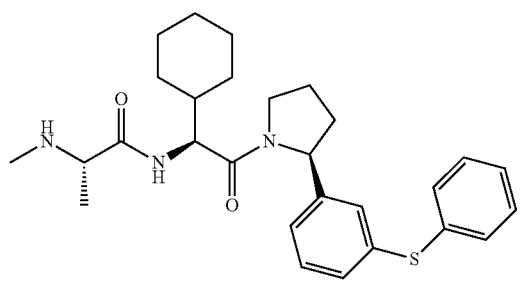

(S)—N-{(S)-1-Cyclohexyl-2-oxo-2-[(S)-2-(3-phenylsulfanyl-phenyl)-pyrrolidin-1-yl]ethyl}-2-methylaminopropionamide;

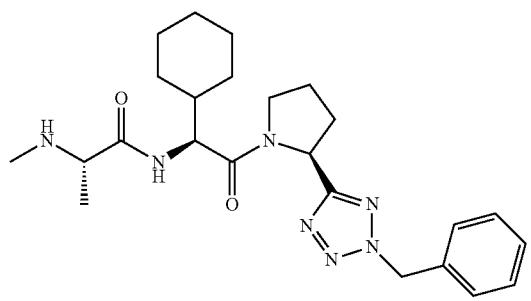

(S)—N-{(S)-2-[(S)-2-(2-Benzyl-2H-tetrazol-5-yl)-pyrrolidin-1-yl]-1-cyclohexyl-2-oxoethyl}-2-methylaminopropionamide;

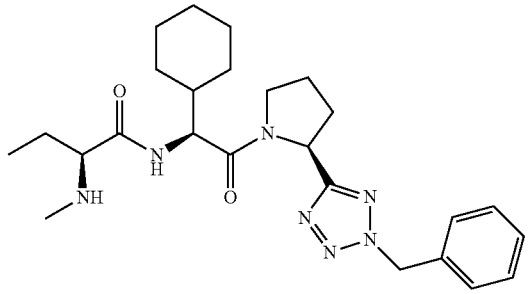

(S)—N-{(S)-2-[(S)-2-(2-Benzyl-2H-tetrazol-5-yl)-pyrrolidin-1-yl]-1-cyclohexyl-2-oxoethyl}-2-methylaminobutyramide;

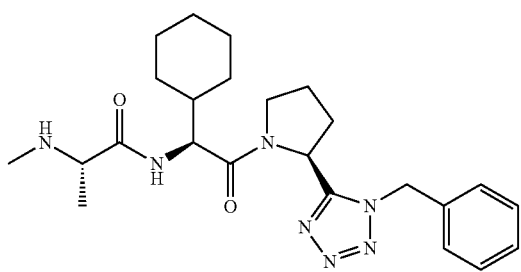

(S)—N-{(S)-2-[(S)-2-(1-Benzyl-1H-tetrazol-5-yl)-pyrrolidin-1-yl]-1-cyclohexyl-2-oxoethyl}-2-methylaminopropionamide; and

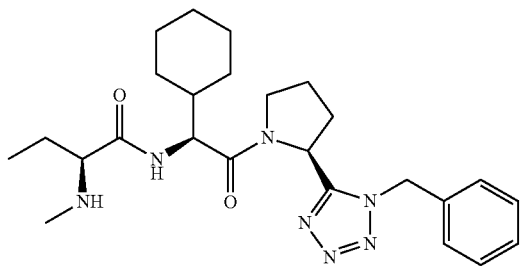

(S)—N-{(S)-2-[(S)-2-(1-Benzyl-1H-tetrazol-5-yl)-pyrrolidin-1-yl]-1-cyclohexyl-2-oxoethyl}-2-methylaminobutyramide;

or a pharmaceutically acceptable salt thereof.

* * * * *